United States Patent
Smith et al.

(10) Patent No.: US 9,598,457 B2
(45) Date of Patent: Mar. 21, 2017

(54) SUBSTITUTED NUCLEOSIDES, NUCLEOTIDES AND ANALOGS THEREOF

(71) Applicant: Alios BioPharma, Inc., South San Francisco, CA (US)

(72) Inventors: David Bernard Smith, San Mateo, CA (US); Leonid Beigelman, San Mateo, CA (US); Guangyi Wang, Carlsbad, CA (US); Michael Hunter Welch, Mountain View, CA (US)

(73) Assignee: Alios BioPharma, Inc., South San Francisco, CA (US)

( * ) Notice: Subject to any disclaimer, the term of this patent is extended or adjusted under 35 U.S.C. 154(b) by 0 days.

(21) Appl. No.: 14/654,360

(22) PCT Filed: Dec. 19, 2013

(86) PCT No.: PCT/US2013/076727
§ 371 (c)(1),
(2) Date: Jun. 19, 2015

(87) PCT Pub. No.: WO2014/100498
PCT Pub. Date: Jun. 26, 2014

(65) Prior Publication Data
US 2016/0039861 A1  Feb. 11, 2016

Related U.S. Application Data

(60) Provisional application No. 61/745,471, filed on Dec. 21, 2012.

(51) Int. Cl.
| | | |
|---|---|---|
| *C07H 19/22* | (2006.01) | |
| *C07H 19/207* | (2006.01) | |
| *C07H 19/167* | (2006.01) | |
| *C07H 19/20* | (2006.01) | |
| *A61K 45/06* | (2006.01) | |
| *C07H 19/16* | (2006.01) | |

(52) U.S. Cl.
CPC ............ *C07H 19/207* (2013.01); *A61K 45/06* (2013.01); *C07H 19/16* (2013.01); *C07H 19/167* (2013.01); *C07H 19/20* (2013.01)

(58) Field of Classification Search
None
See application file for complete search history.

(56) References Cited

U.S. PATENT DOCUMENTS

| | | | |
|---|---|---|---|
| 5,432,272 A | 7/1995 | Benner et al. | |
| 7,125,855 B2 * | 10/2006 | Bhat | A61K 31/7056 514/43 |
| 2012/0070411 A1 | 3/2012 | Beigelman et al. | |
| 2012/0070415 A1 | 3/2012 | Beigelman et al. | |
| 2012/0071434 A1 | 3/2012 | Smith et al. | |
| 2012/0165286 A1 | 6/2012 | Beigelman et al. | |
| 2013/0164261 A1 | 6/2013 | Wang et al. | |
| 2013/0165400 A1 | 6/2013 | Beigelman et al. | |
| 2013/0252920 A1 | 9/2013 | Blatt et al. | |
| 2013/0253181 A1 | 9/2013 | Serebryany et al. | |
| 2013/0281687 A1 | 10/2013 | Serebryany et al. | |
| 2014/0179627 A1 | 6/2014 | Beigelman et al. | |
| 2014/0179910 A1 | 6/2014 | Beigelman et al. | |
| 2014/0286903 A1 * | 9/2014 | Chamberlain | A61K 31/52 424/85.7 |
| 2014/0303108 A1 | 10/2014 | Beigelman et al. | |
| 2014/0303113 A1 | 10/2014 | Krop et al. | |
| 2015/0011497 A1 | 1/2015 | Beigelman et al. | |
| 2015/0038451 A1 | 2/2015 | Smith et al. | |
| 2015/0051167 A1 | 2/2015 | Wang et al. | |
| 2015/0105341 A1 | 4/2015 | Beigelman et al. | |
| 2015/0141363 A1 | 5/2015 | Wang et al. | |
| 2015/0175647 A1 | 6/2015 | Kuldipkumar et al. | |
| 2015/0183819 A1 | 7/2015 | Beigelman et al. | |
| 2015/0315228 A1 | 11/2015 | Beigelman et al. | |
| 2015/0366887 A1 | 12/2015 | Blatt et al. | |
| 2015/0366888 A1 | 12/2015 | Blatt et al. | |
| 2015/0368286 A1 | 12/2015 | Serebryany et al. | |
| 2016/0016987 A1 | 1/2016 | Beigelman et al. | |
| 2016/0022724 A1 | 1/2016 | Chanda et al. | |
| 2016/0024136 A1 | 1/2016 | Beigelman et al. | |
| 2016/0039858 A1 | 2/2016 | Beigelman et al. | |
| 2016/0115190 A1 | 4/2016 | Serebryany et al. | |
| 2016/0176910 A1 | 6/2016 | Wang et al. | |
| 2016/0176911 A1 | 6/2016 | Beigelman et al. | |

FOREIGN PATENT DOCUMENTS

| | | |
|---|---|---|
| WO | WO 02/32920 | 4/2002 |
| WO | WO 02/057425 | 7/2002 |
| WO | WO 2005/020885 | 3/2005 |
| WO | WO 2010/108140 | 9/2010 |

(Continued)

OTHER PUBLICATIONS

Arnold et al. "Sensitivity of Mitochondrial Transcription and Resistance of RNA Polymerase II Dependent Nuclear Transcription to Antiviral Ribonucleosides" PLoS Pathog (2012) 8(11): e1003030. doi:10.1371/journal.ppat.1003030.

Eldrup et al., "Structure-Activity Relationship of Purine Ribonucleosides for Inhibition of Hepatitis C Virus RNA-Dependent RNA Polymerase" J. Med. Chem. (2004) 47(9):2283-2295.

Greene, et al., Protective Groups in Organic Synthesis, 3. Ed., John Wiley & Sons, (1999) Cover & Contents pages.

"IUPAC-IUB Commission on Biochemical Nomenclature Abbreviated Nomenclature of Synthetic Polypeptides (Polymerized Amino Acids) Revised Recommendations (1971)" *Biochemistry.* (1972) 11(5) :942-944.

(Continued)

*Primary Examiner* — Patrick Lewis
(74) *Attorney, Agent, or Firm* — Knobbe, Martens, Olson & Bear, LLP

(57) ABSTRACT

Disclosed herein are nucleotide analogs, methods of synthesizing nucleotide analogs and methods of treating diseases and/or conditions such as a HCV infection with one or more nucleotide analogs.

20 Claims, 39 Drawing Sheets

(56) References Cited

FOREIGN PATENT DOCUMENTS

| WO | WO 2012/040127 | 3/2012 | | |
|---|---|---|---|---|
| WO | WO 2012/142085 | 10/2012 | | |
| WO | WO 2013/070887 | 5/2013 | | |
| WO | WO 2013/070887 A1 * | 5/2013 | ............. | A61K 31/52 |
| WO | WO 2013/092481 | 6/2013 | | |
| WO | WO 2013/142124 | 9/2013 | | |
| WO | WO 2013/142159 | 9/2013 | | |
| WO | WO 2013/142525 | 9/2013 | | |
| WO | WO 2014/134251 | 9/2014 | | |
| WO | WO 2014/164533 | 10/2014 | | |
| WO | WO 2014/209983 | 12/2014 | | |
| WO | WO 2016/022464 | 2/2016 | | |

OTHER PUBLICATIONS

McOmie, J. F. W., Protective Groups in Organic Chemistry, Plenum Press, 1973. Cover & Contents pages only.

McGuigan et al., "The application of the phosphoramidate ProTide approach confers micromolar potency against Hepatitis C virus on inactive agent 4'-azidoinosine: Kinase bypass on a dual base/sugar modified nucleoside" Bioorganic & Medicinal Chemistry Letters (2009) 19(11):3122-3124.

Extended European Search Report dated Jul. 4, 2016 for EP Application No. 13865366.2, filed Dec. 19, 2013.

International Search Report and Written Opinion dated Feb. 28, 2014 for PCT Application No. PCT/US2013/076727 filed Dec. 19, 2013.

International Preliminary Report on Patentability dated Jun. 23, 2015 for PCT Application No. PCT/US2013/076727 filed Dec. 19, 2013.

* cited by examiner

Figure 1: HCV Protease Inhibitors

| # | Name | Structure |
|---|---|---|
| 1001 | Telaprevir VX-950 | 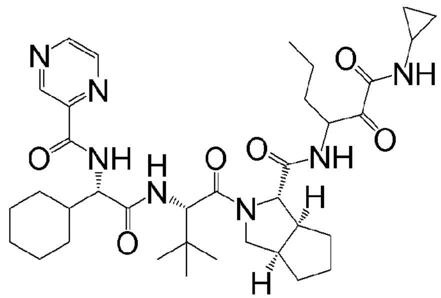 |
| 1002 | MK-5172 | 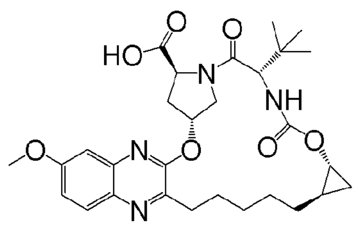 |
| 1003 | ABT-450 | |
| 1004 | BILN-2061 | |
| 1005 | BI-201335 BI335 | |

Figure 1 (cont.): HCV Protease Inhibitors

| # | Name | Structure |
|---|---|---|
| 1006 | BMS-650032 BM032 Asunaprevir | 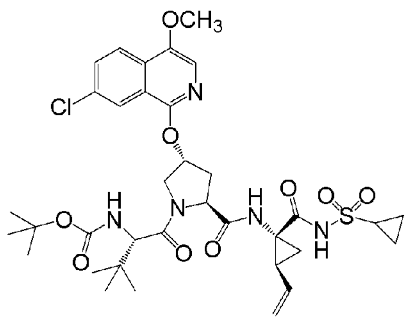 |
| 1007 | Boceprevir SCH 503034 | 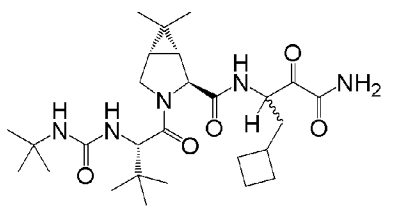 |
| 1008 | GS-9256 | |
| 1009 | GS-9451 | |
| 1010 | IDX-320 | |
| 1011 | ACH-1625 | |
| 1012 | ACH-2684 | |

| # | Name | Structure |
|---|---|---|
| 1013 | TMC-435 TMC-435350 | 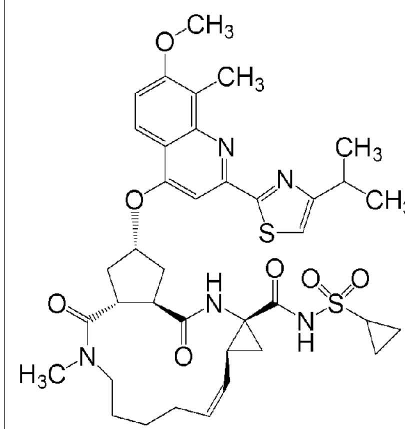 |
| 1014 | Danoprevir ITMN-191 RG7227 RO5190591 | 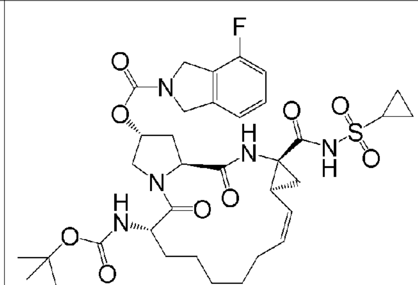 |

Figure 1 (cont.): HCV Protease Inhibitors
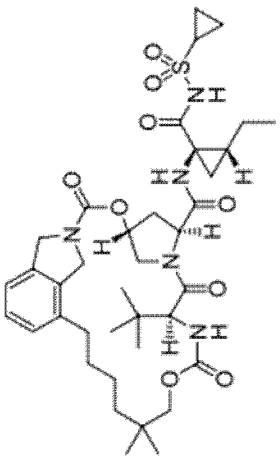
| # | Name | Structure |
|---|------|-----------|
| 1015 | MK-7009 Vaniprevir | 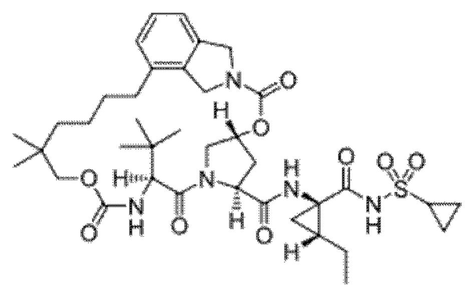 |
| 1016 | PHX1766 | |

Figure 2: HCV Polymerase Inhibitors – Nucleosides, Nucleotides and Analogs Thereof
| # | Name | Structure |
|---|---|---|
| 2001 | RG7128 Mericitabine | 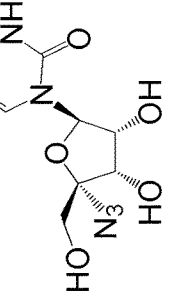 |
| 2002 | PSI-7851 | 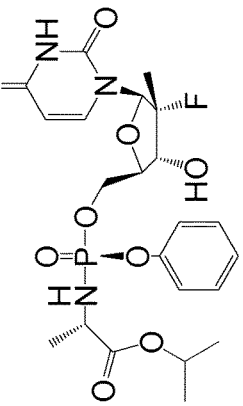 |
| 2003 | PSI-7977 GS-7977, Sofosbuvir | 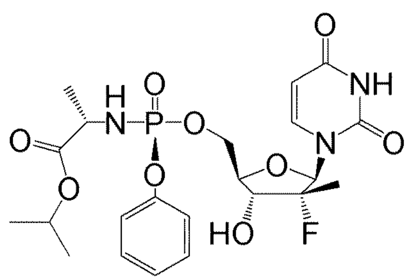 |
| 2004 | PSI-352938 GS-938 | 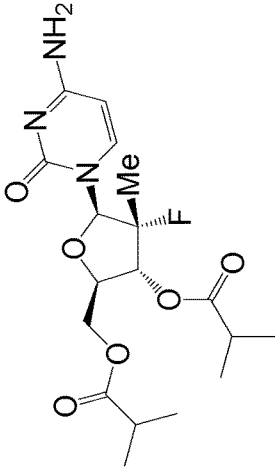 |
| 2005 | 4'-azidouridine and its prodrugs | 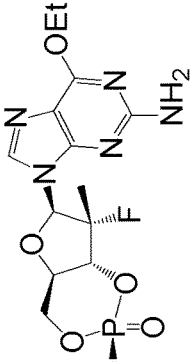 |
| 2006 | PSI-661 | |
| 2007 | GS-6620 | |
| 2008 | TMC649128 | |

Figure 2 (cont.): HCV Polymerase Inhibitors – Nucleosides, Nucleotides and Analogs Thereof

| # | Name | Structure |
|---|---|---|
| 2009 | NM283 | ![structure with NH2, cytosine base, sugar with Me, OH, ValO, HO] |
| 2010 | BCX5191 | |
| 2011 | IDX19368 | |
| 2012 | IDX19370 | |

Figure 3: HCV Polymerase Inhibitors – Non-Nucleosides

| # | Name | Structure |
|---|---|---|
| 3001 | ABT-333 | |
| 3002 | ANA-598 Setrobuvir | 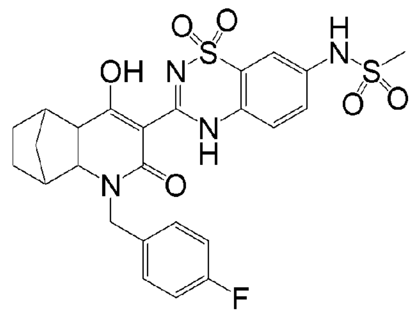 |
| 3003 | VX-222 S1480 VCH-222 | 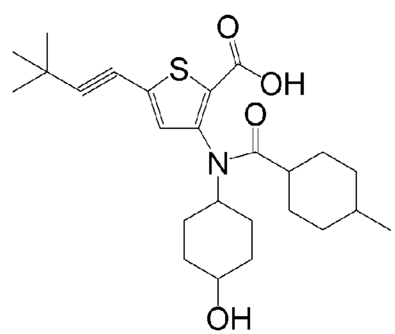 |
| 3004 | HCV-796 | 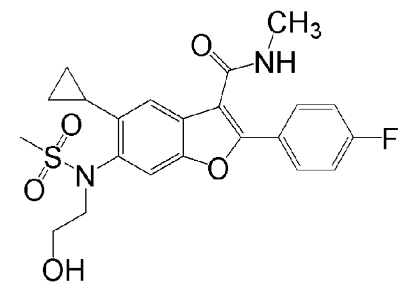 |
| 3005 | BI-207127 | |
| 3006 | GS-9190 | 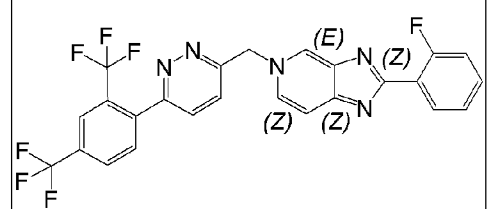 |
| 3007 | Filibuvir PF-00868554 | 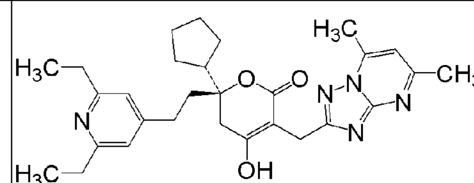 |

Figure 3 (cont.): HCV Polymerase Inhibitors – Non-Nucleosides
| # | Name | Structure |
|---|------|-----------|
| 3008 | VX-497 | 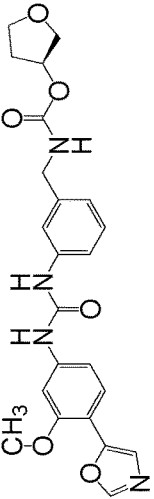 |
| 3009 | ABT-072 | |
| 3010 | MK-3281 | |
| 3011 | TMC647055 | |
| 3012 | BMS-791325 | |
| 3013 | PPI-383 | |
| 3014 | GS9669 | |

Figure 4: NS5A Inhibitors

| # | Name | Structure |
|---|---|---|
| 4001 | BMS-790052 BMS052 S1482 Daclatasvir | *(structure shown)* |
| 4002 | PPI-461 | |
| 4003 | ACH-2928 | |
| 4004 | GS-5885 | |
| 4005 | BMS-824393 | |
| 4006 | ABT 267 | |
| 4007 | ACH-3102 | |
| 4008 | AZD-7295 | |
| 4009 | IDX719 | |
| 4010 | PPI-668 | |
| 4011 | MK8742 | |
| 4012 | GSK805 | |

Figure 5: Other Antivirals and Ribavirin

| # | Name | Structure |
|---|---|---|
| 5001 | Debio-025 Alisporivir | |
| 5002 | MIR-122 | |
| 5003 | clemizole | |
| 5004 | ITX 5061 | |
| 5005 | BIT225 | |
| 5006 | NIM811 | |
| 5007 | SCY-635 | |
| 5008 | Nitazoxanide | (structure shown) |
| 5009 | Miravirsen | |

| # | Name | Structure |
|---|---|---|
| 5010 | Celgosivir | (structure shown) |
| 5011 | GS9620 | |
| 5012 | Ribavirin | (structure shown) |

Figure 6: Compounds of Formula (CC) and alpha-thiotriphosphates thereof

Figure 6 (cont.): Compounds of Formula (CC) and alpha-thiotriphosphates thereof

| # | Structure |
|---|---|
| 6007 | 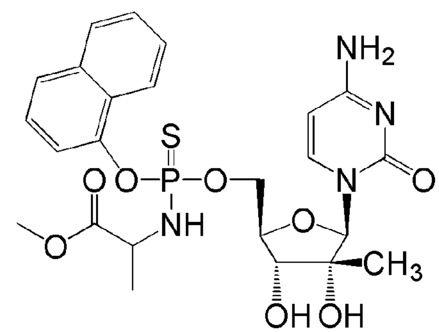 |
| 6008 | 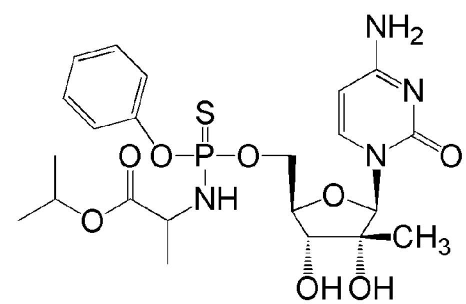 |

| # | Structure |
|---|---|
| 6005 | 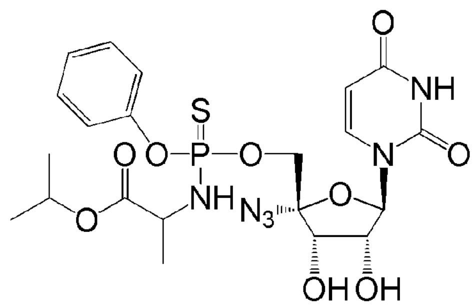 |
| 6006 | 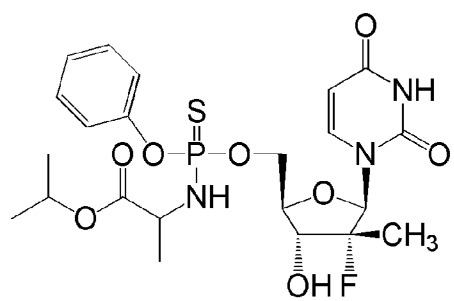 |

Figure 6 (cont.): Compounds of Formula (CC) and alpha-thiotriphosphates thereof

| # | Structure |
|---|---|
| 6009 | 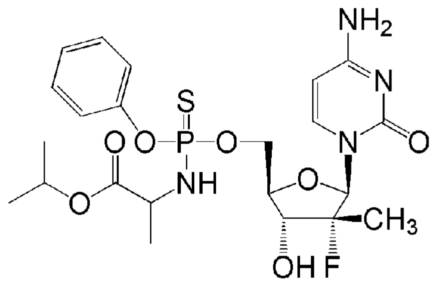 |
| 6010 | 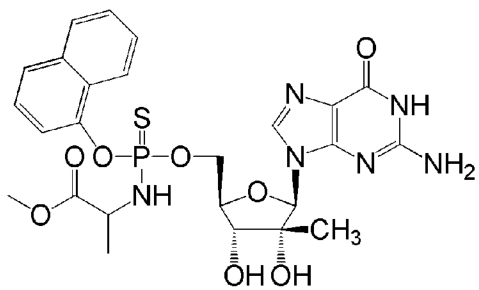 |

| # | Structure |
|---|---|
| 6011 | 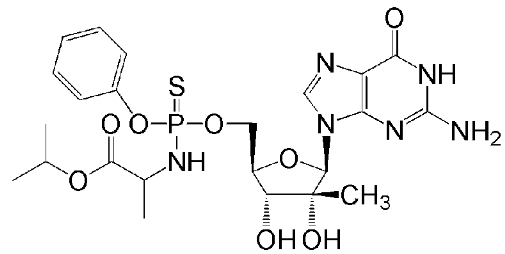 |
| 6012 | 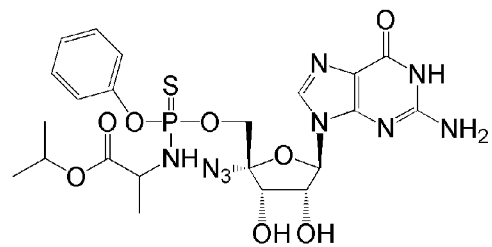 |
| 6013 | 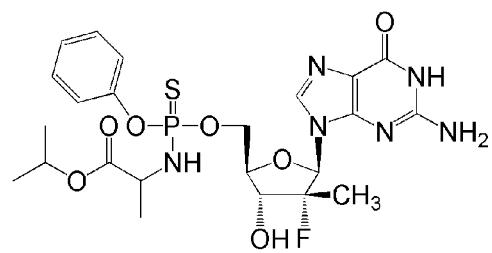 |

Figure 6 (cont.): Compounds of Formula (CC) and alpha-thiotriphosphates thereof

| # | Structure |
|---|---|
| 6016 | (structure) |
| 6017 | (structure) |
| 6014 | (structure) |
| 6015 | (structure) |

Figure 6 (cont.): Compounds of Formula (CC) and alpha-thiotriphosphates thereof

Figure 6 (cont.): Compounds of Formula (CC) and alpha-thiotriphosphates thereof
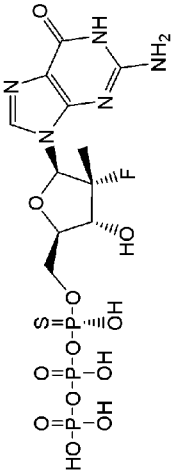

Figure 6 (cont.): Compounds of Formula (CC) and alpha-thiotriphosphates thereof

Figure 6 (cont.): Compounds of Formula (CC) and alpha-thiotriphosphates thereof

| # | Structure |
|---|---|
| 6040 | (structure) |
| 6041 | (structure) |
| 6042 | (structure) |

| # | Structure |
|---|---|
| 6037 | (structure) |
| 6038 | (structure) |
| 6039 | (structure) |

Figure 6 (cont.): Compounds of Formula (CC) and alpha-thiotriphosphates thereof

| # | Structure |
|---|---|
| 6043 | 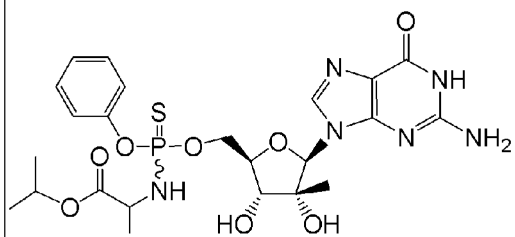 |
| 6044 | 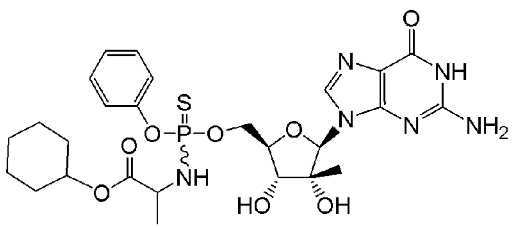 |
| 6045 | 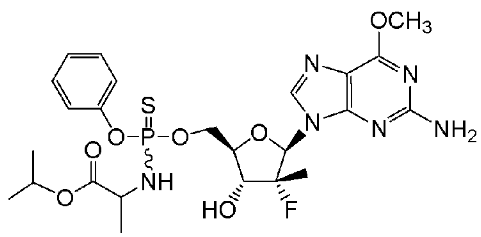 |
| 6046 | |
| 6047 | |
| 6048 | |

Figure 6 (cont.): Compounds of Formula (CC) and alpha-thiotriphosphates thereof

Figure 6 (cont.): Compounds of Formula (CC) and alpha-thiotriphosphates thereof

| # | Structure |
|---|---|
| 6055 | (adenine nucleoside with 2'-methyl, 2'-OH, 3'-OH; 5'-O-phenyl(neopentyloxy-alaninyl) thiophosphoramidate) |
| 6056 | (adenine nucleoside with 2'-methyl, 2'-OH, 3'-OH; 5'-O-(1-naphthyl)(isopropoxy-alaninyl) thiophosphoramidate) |
| 6057 | (uracil nucleoside with 4'-azido, 3'-OH, 2'-OH; 5'-O-phenyl(isopropoxy-alaninyl) thiophosphoramidate) |

| # | Structure |
|---|---|
| 6053 | (N6-allyl-2-amino purine nucleoside with 2'-methyl, 2'-OH, 3'-OH; 5'-O-phenyl(isopropoxy-alaninyl) thiophosphoramidate) |
| 6054 | (6-chloro-2-amino purine nucleoside with 2'-methyl, 2'-OH, 3'-OH; 5'-O-phenyl(isopropoxy-alaninyl) thiophosphoramidate) |

Figure 6 (cont.): Compounds of Formula (CC) and alpha-thiotriphosphates thereof

| # | Structure |
|---|---|
| 6060 | (structure) |
| 6061 | (structure) |
| 6062 | (structure) |

| # | Structure |
|---|---|
| 6058 | (structure) |
| 6059 | (structure) |

Figure 6 (cont.): Compounds of Formula (CC) and alpha-thiotriphosphates thereof

| # | Structure |
|---|---|
| 6066 | (structure) |
| 6067 | (structure) |
| 6068 | (structure) |

| # | Structure |
|---|---|
| 6063 | (structure) |
| 6064 | (structure) |
| 6065 | (structure) |

Figure 6 (cont.): Compounds of Formula (CC) and alpha-thiotriphosphates thereof

| # | Structure |
|---|---|
| 6072 | (structure) |
| 6073 | (structure) |
| 6074 | (structure) |

| # | Structure |
|---|---|
| 6069 | (structure) |
| 6070 | (structure) |
| 6071 | (structure) |

Figure 6 (cont.): Compounds of Formula (CC) and alpha-thiotriphosphates thereof

| # | Structure |
|---|---|
| 6075 | 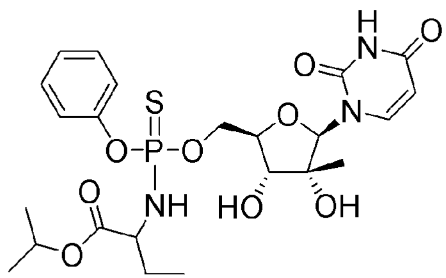 |
| 6076 | 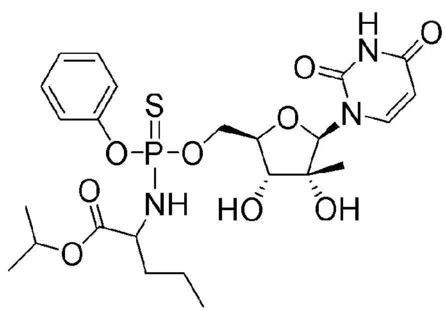 |
| 6077 | |
| 6078 | |

Figure 7: Compounds of Formula (AA)

| # | Structure |
|---|---|
| 7000 | *(structure with B¹ᴬᴬ, R¹ᴬᴬ, R²ᴬᴬ, R³ᴬᴬ, R⁴ᴬᴬ, R⁵ᴬᴬ substituents)* |
| 7001 | *(uridine analog with C≡CH and OH at 2'-position, 3'-OH, 5'-O-phosphoramidate bearing S, phenoxy, and NH-CH(CH₃)-C(O)-O-isopropyl (alanine isopropyl ester))* |

| # | Structure |
|---|---|
| 7002 | *(uridine analog with CH=CH₂ and OH at 2'-position, 3'-OH, 5'-O-phosphoramidate bearing S, phenoxy, and NH-CH(CH₃)-C(O)-O-isopropyl)* |
| 7003 | *(uridine analog with CH₂CH₃ (ethyl) and OH at 2'-position, 3'-OH, 5'-O-phosphoramidate bearing S, phenoxy, and NH-CH(CH₃)-C(O)-O-isopropyl)* |

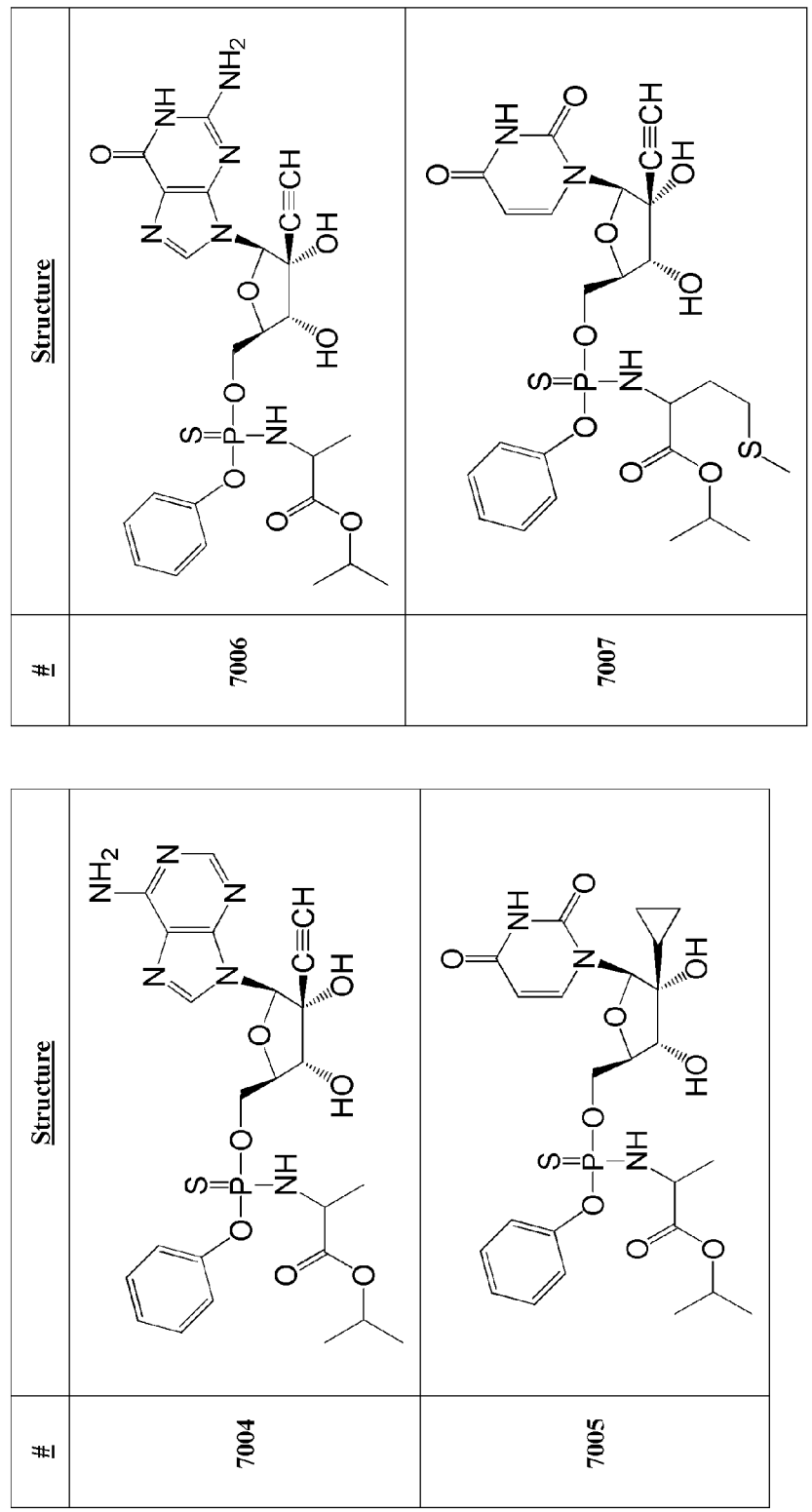
Figure 7 (cont.): Compounds of Formula (AA)

Figure 7 (cont.): Compounds of Formula (AA)

| # | Structure |
|---|---|
| 7010 | (4-fluorophenyl phosphorothioate, isopropyl alaninate ester of 2'-C-ethynyl uridine) |
| 7011 | (4-chlorophenyl phosphorothioate, isopropyl alaninate ester of 2'-C-ethynyl uridine) |
| 7008 | (phenyl phosphorothioate, isopropyl valinate ester of 2'-C-ethynyl uridine) |
| 7009 | (phenyl phosphorothioate, isopropyl leucinate ester of 2'-C-ethynyl uridine) |

Figure 7 (cont.): Compounds of Formula (AA)

| # | Structure |
|---|---|
| 7014 | (structure: uridine with 2'-C≡C-CH₃, 3'-OH, 5'-O-phosphorothioate bearing phenoxy and alanine isopropyl ester) |
| 7015 | (structure: uridine with 2'-C≡C-I, 3'-OH, 5'-O-phosphorothioate bearing phenoxy and alanine isopropyl ester) |
| 7012 | (structure: uridine with 2'-C≡CH, 3'-OH, 5'-O-phosphorothioate bearing 3-chloro-4-fluorophenoxy and alanine isopropyl ester) |
| 7013 | (structure: uridine with 2'-C≡CH, 3'-OH, 5'-O-phosphorothioate bearing 1-naphthyloxy and alanine isopropyl ester) |

Figure 7 (cont.): Compounds of Formula (AA)

| # | Structure |
|---|---|
| 7018 | 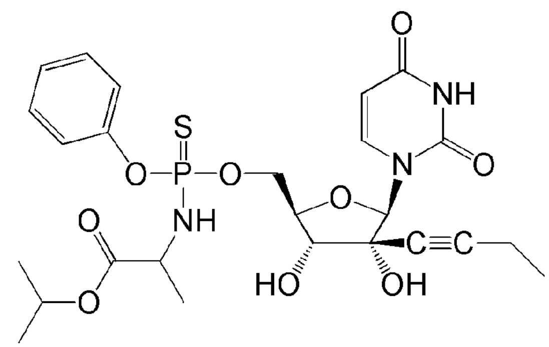 |
| 7019 | 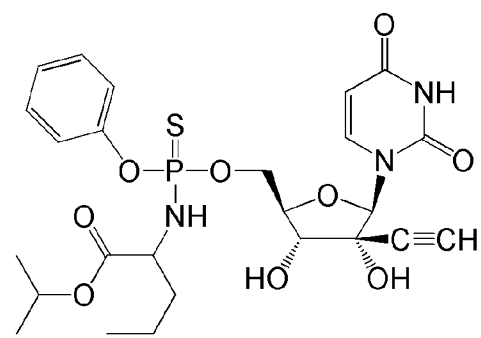 |

| # | Structure |
|---|---|
| 7016 | 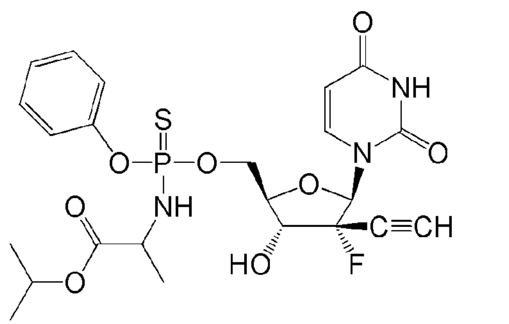 |
| 7017 | 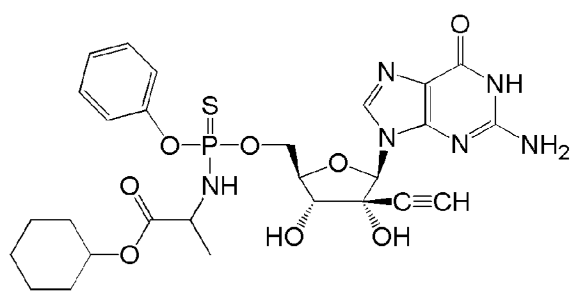 |

Figure 7 (cont.): Compounds of Formula (AA)

| # | Structure |
|---|---|
| 7020 | 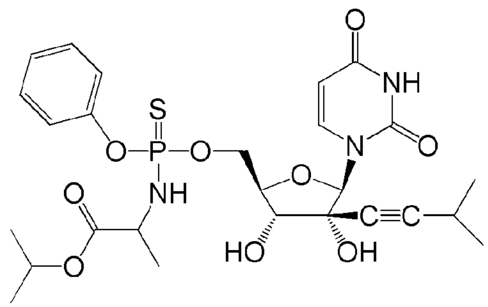 |
| 7021 | 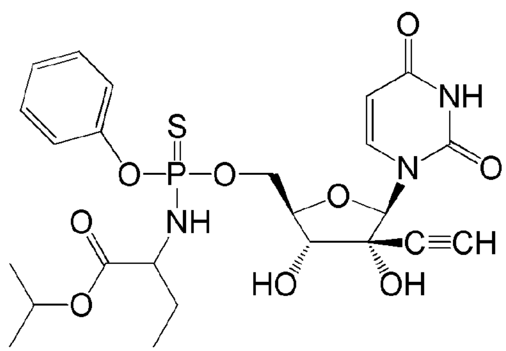 |
| 7022 | |
| 7023 | |

Figure 7 (cont.): Compounds of Formula (AA)

| # | Structure |
|---|---|
| 7026 | 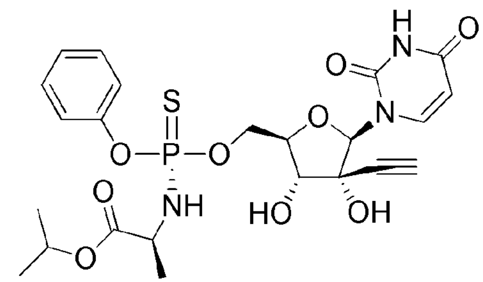 |
| 7027 | 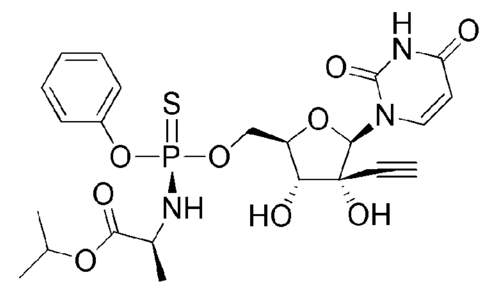 |

| # | Structure |
|---|---|
| 7024 | 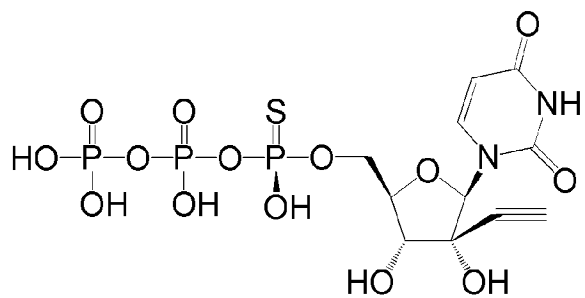 |
| 7025 | 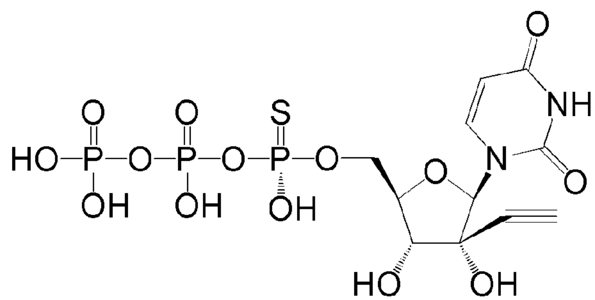 |

Figure 8: Compounds of Formula (BB)
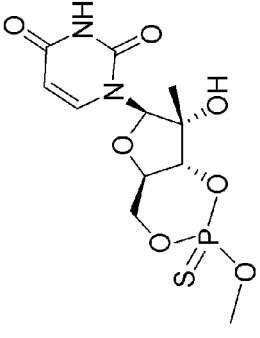

Figure 8 (cont.): Compounds of Formula (BB)

| # | Structure |
|---|---|
| 8006 | (structure) |
| 8007 | (structure) |
| 8008 | (structure) |

| # | Structure |
|---|---|
| 8009 | (structure) |
| 80010 | (structure) |
| 8011 | (structure) |

Figure 8 (cont.): Compounds of Formula (BB)
| # | Structure |
|---|---|
| 8015 | 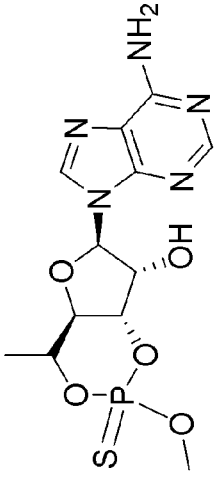 |
| 8016 | 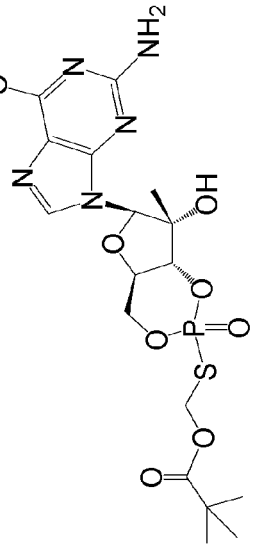 |
| # | Structure |
|---|---|
| 8012 | 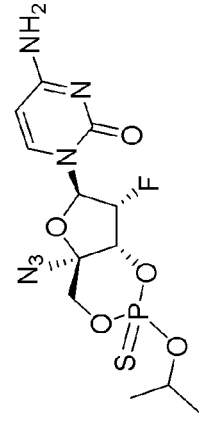 |
| 8013 | 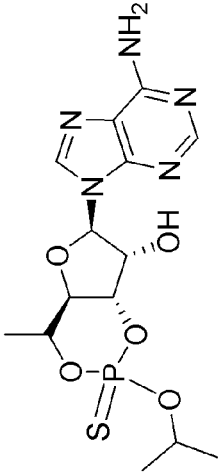 |
| 8014 | 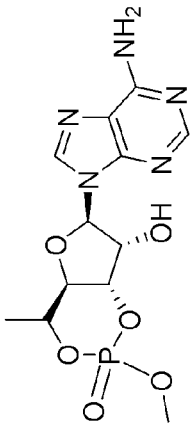 |

Figure 9: Compounds of Formula (I)

Figure 9 (cont.): Compounds of Formula (I)

| # | Structure |
|---|---|
| 9011 | 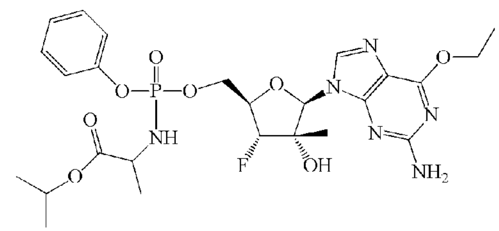 |
| 9012 | 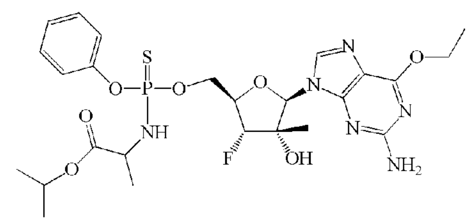 |
| 9013 | 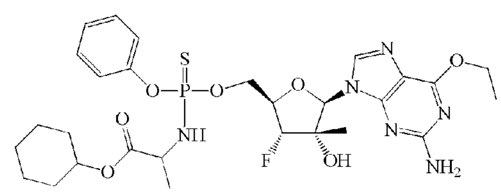 |

| # | Structure |
|---|---|
| 9007 | 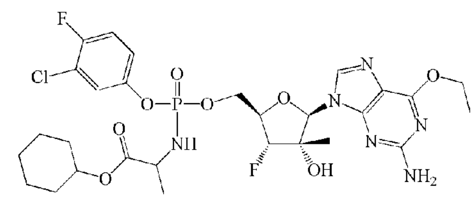 |
| 9008 | 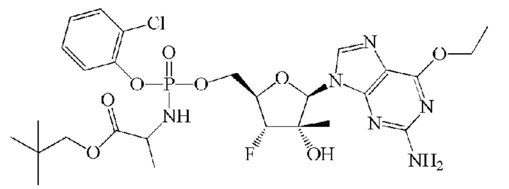 |
| 9009 | 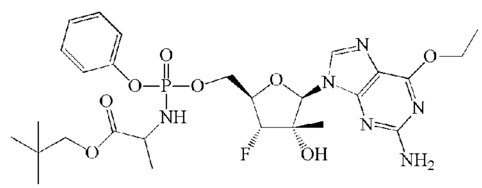 |
| 9010 | 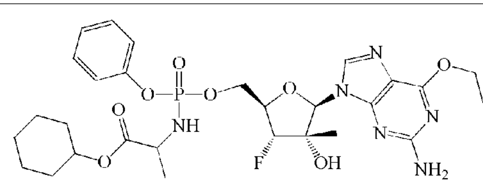 |

Figure 9 (cont.): Compounds of Formula (I)
| # | Structure |
|---|---|
| 9014 | 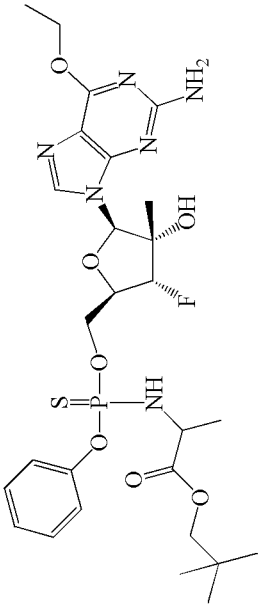 |
| 9015 | 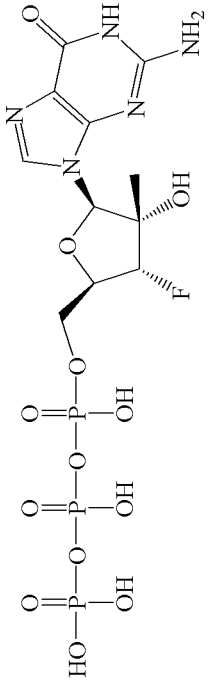 |

GTP = guanosine-5'-triphosphate

ATP = adenosine 5'-triphosphate

Figure 11
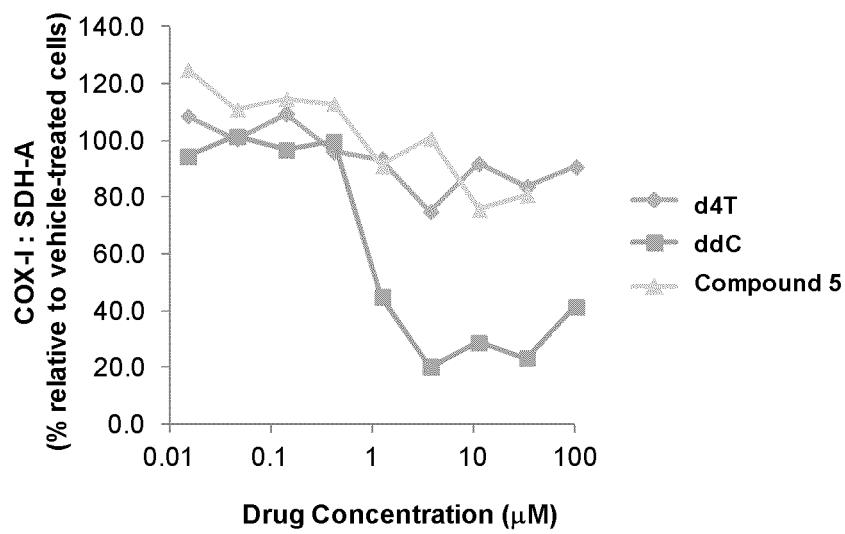
A
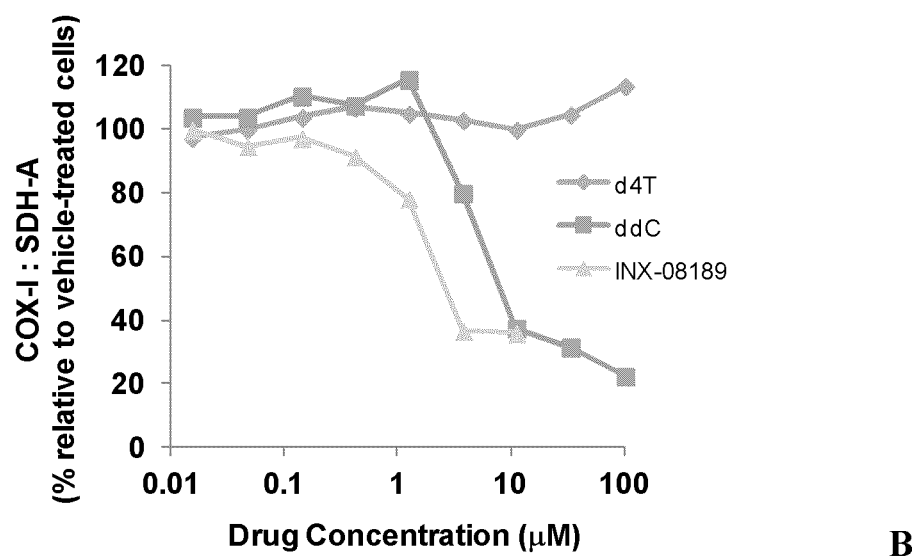
B

SUBSTITUTED NUCLEOSIDES, NUCLEOTIDES AND ANALOGS THEREOF

INCORPORATION BY REFERENCE TO ANY PRIORITY APPLICATIONS

Any and all applications for which a foreign or domestic priority claim is identified in the Application Data Sheet as filed with the present application, are hereby incorporated by reference under 37 CFR 1.57.

REFERENCE TO SEQUENCE LISTING

The present application is being filed along with a Sequence Listing in electronic format. The Sequence Listing is provided as a file entitled SEQLISTING_067.TXT, created Dec. 19, 2013, which is 728 bytes in size. The information in the electronic format of the Sequence Listing is incorporated herein by reference in its entirety.

BACKGROUND

Field

The present application relates to the fields of chemistry, biochemistry and medicine. More particularly, disclosed herein are nucleotide analogs, pharmaceutical compositions that include one or more nucleotide analogs and methods of synthesizing the same. Also disclosed herein are methods of treating diseases and/or conditions with a nucleotide analog, alone or in combination therapy with one or more other agents.

Description

Nucleoside analogs are a class of compounds that have been shown to exert antiviral and anticancer activity both in vitro and in vivo, and thus, have been the subject of widespread research for the treatment of viral infections. Nucleoside analogs are usually therapeutically inactive compounds that are converted by host or viral enzymes to their respective active anti-metabolites, which, in turn, may inhibit polymerases involved in viral or cell proliferation. The activation occurs by a variety of mechanisms, such as the addition of one or more phosphate groups and, or in combination with, other metabolic processes.

SUMMARY

Some embodiments disclosed herein relate to a compound of Formula (I) or a pharmaceutically acceptable salt thereof.

Some embodiments disclosed herein relate to a method of ameliorating and/or treating a hepatitis C viral (HCV) infection that can include administering to a subject identified as suffering from the HCV infection a therapeutically effective amount of one or more compounds of Formula (I), or a pharmaceutically acceptable salt thereof, or a pharmaceutical composition that includes one or more compounds of Formula (I), or a pharmaceutically acceptable salt thereof. Other embodiments described herein relate to using one or more compounds of Formula (I), or a pharmaceutically acceptable salt thereof, in the manufacture of a medicament for ameliorating and/or treating a HCV infection. Still other embodiments described herein relate to one or more compounds of Formula (I), or a pharmaceutically acceptable salt thereof, or a pharmaceutical composition that includes one or more compounds of Formula (I), or a pharmaceutically acceptable salt thereof, that can be used for ameliorating and/or treating a HCV infection.

Some embodiments disclosed herein relate to a method of ameliorating and/or treating a HCV infection that can include contacting a cell infected with the hepatitis C virus with an effective amount of one or more compounds described herein, or a pharmaceutically acceptable salt of one or more compounds described herein, or a pharmaceutical composition that includes one or more compounds described herein, or a pharmaceutically acceptable salt thereof. Other embodiments described herein relate to using one or more compounds described herein, or a pharmaceutically acceptable salt of one or more compounds described herein, in the manufacture of a medicament for ameliorating and/or treating a HCV infection that can include contacting a cell infected with the hepatitis C virus with an effective amount of said compound(s). Still other embodiments described herein relate to one or more compounds described herein, or a pharmaceutically acceptable salt of one or more compounds described herein, or a pharmaceutical composition that includes one or more compounds described herein, or a pharmaceutically acceptable salt thereof, that can be used for ameliorating and/or treating a HCV infection by contacting a cell infected with the hepatitis C virus with an effective amount of said compound(s).

Some embodiments disclosed herein relate to a method of inhibiting replication of a hepatitis C virus that can include contacting a cell infected with the hepatitis C virus with an effective amount of one or more compounds described herein, or a pharmaceutically acceptable salt of one or more compounds described herein, or a pharmaceutical composition that includes one or more compounds described herein, or a pharmaceutically acceptable salt thereof. Other embodiments described herein relate to using one or more compounds described herein, or a pharmaceutically acceptable salt of one or more compounds described herein, in the manufacture of a medicament for inhibiting replication of a hepatitis C virus that can include contacting a cell infected with the hepatitis C virus with an effective amount of said compound(s). Still other embodiments described herein relate to one or more compounds described herein, or a pharmaceutically acceptable salt of one or more compounds described herein, or a pharmaceutical composition that includes one or more compounds described herein, or a pharmaceutically acceptable salt thereof, that can be used for inhibiting replication of a hepatitis C virus by contacting a cell infected with the hepatitis C virus with an effective amount of said compound(s).

Some embodiments disclosed herein relate to a method of ameliorating and/or treating a HCV infection that can include administering to a subject identified as suffering from the HCV infection a therapeutically effective amount of a compound described herein or a pharmaceutically acceptable salt thereof (for example, one or more compounds of Formula (I), or a pharmaceutically acceptable salt thereof), or a pharmaceutical composition that includes a compound described herein, or a pharmaceutically acceptable salt thereof, in combination with an agent selected from an interferon, ribavirin, a HCV protease inhibitor, a HCV polymerase inhibitor, a NS5A inhibitor, an other antiviral compound, a compound of Formula (AA), a compound of Formula (BB) and a compound of Formula (CC), or a pharmaceutically acceptable salt of any of the foregoing. Some embodiments disclosed herein relate to a method of ameliorating and/or treating a HCV infection that can include contacting a cell infected with the HCV infection with a therapeutically effective amount of a compound described herein or a pharmaceutically acceptable salt thereof (for example, one or more compounds of Formula (I), or a pharmaceutically acceptable salt thereof), or a pharmaceutical composition that includes a compound described herein, in combination with an agent selected from an interferon, ribavirin, a HCV protease inhibitor, a HCV polymerase inhibitor, a NS5A inhibitor, an other antiviral compound, a compound of Formula (AA), a compound of Formula (BB) and a compound of Formula (CC), or a pharmaceutically acceptable salt of any of the foregoing. Some embodiments disclosed herein relate to a method of inhibiting replication of a hepatitis C virus that can include administering to a subject identified as suffering from a HCV infection a therapeutically effective amount of a compound described herein or a pharmaceutically acceptable salt thereof (for example, a compound of Formula (I), or a pharmaceutically acceptable salt thereof), or a pharmaceutical composition that includes a compound described herein, or a pharmaceutically acceptable salt thereof, in combination with an agent selected from an interferon, ribavirin, a HCV protease inhibitor, a HCV polymerase inhibitor, a NS5A inhibitor, an other antiviral compound, a compound of Formula (AA), a compound of Formula (BB) and a compound of Formula (CC), or a pharmaceutically acceptable salt of any of the foregoing. In some embodiments, the agent can be a compound, or a pharmaceutically acceptable salt thereof, selected from Compound 1001-1016, 2001-2012, 3001-3014, 4001-4012, 5001-5012, 6001-6078, 7000-7027 and 8000-8016, or a pharmaceutical composition that includes one or more of the aforementioned compounds, or a pharmaceutically acceptable salt of the foregoing. In some embodiments, the method can include administering a second agent selected from an interferon, ribavirin, a HCV protease inhibitor, a HCV polymerase inhibitor, a NS5A inhibitor, an other antiviral compound, a compound of Formula (AA), a compound of Formula (BB) and a compound of Formula (CC), or a pharmaceutically acceptable salt of any of the foregoing.

BRIEF DESCRIPTION OF THE DRAWINGS

FIG. 1 shows example HCV protease inhibitors.
FIG. 2 shows example nucleoside HCV polymerase inhibitors.
FIG. 3 shows example non-nucleoside HCV polymerase inhibitors.
FIG. 4 shows example NS5A inhibitors.
FIG. 5 shows example other antivirals.
FIG. 6 shows example compounds of Formula (CC) and alpha-thiotriphosphates thereof, wherein Formula (CC) and alpha-thiotriphosphates thereof are described herein.
FIG. 7 shows example compounds of Formula (AA), wherein Formula (AA) is described herein.
FIG. 8 shows example compounds of Formula (BB), wherein Formula (BB) is described herein.
FIG. 9 shows example compounds of Formula (I), wherein Formula (I) is described herein.
FIG. 11 shows the results of the inhibition of mitochondrial protein synthesis assays.

DETAILED DESCRIPTION

Definitions

Figure 10:
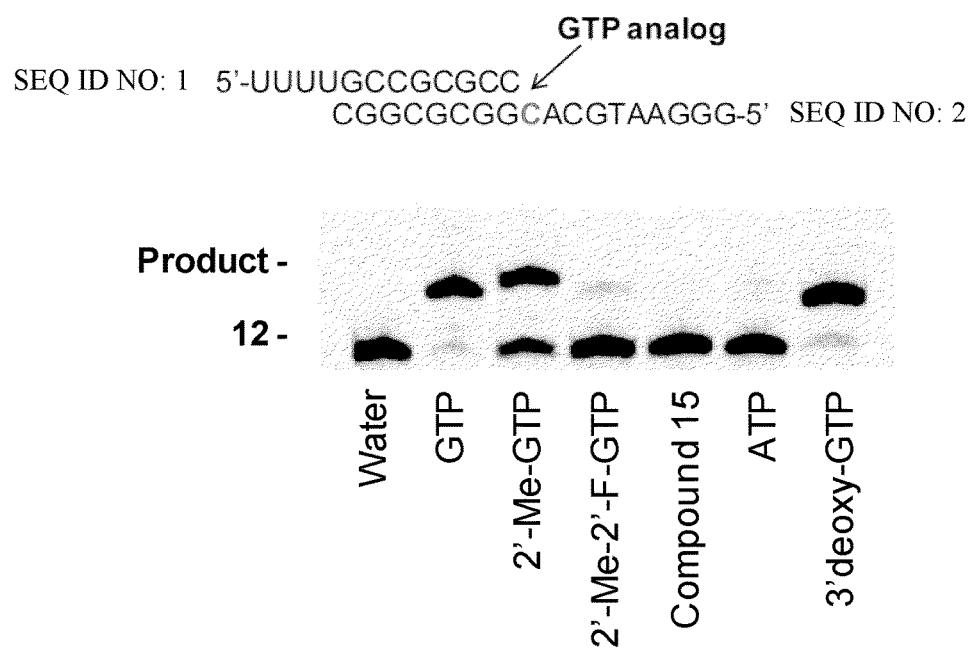
FIG. 10 shows the gels from the assessment of incorporation of several compounds with a guanine base by the human mitochondrial RNA polymerase.

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

As used herein, any "R" group(s) such as, without limitation, $R^1$, $R^2$, $R^3$, $R^{4A}$, $R^{4B}$, $R^5$, $R^6$, $R^7$, $R^8$, $R^{9A}$, $R^{9B}$, $R^{9C}$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{41}$, $R^{42}$, $R^{43}$ and $R^{44}$ represent substituents that can be attached to the indicated atom. An R group may be substituted or unsubstituted. If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

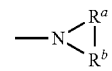

In addition, if two "R" groups are described as being "taken together" with the atom(s) to which they are attached to form a ring as an alternative, the R groups are not limited to the variables or substituents defined previously.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heteroalicyclyl, aralkyl, heteroaralkyl, (heteroalicyclyl)alkyl, hydroxy, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heteroalicyclyl group. That is, the alkyl, alkenyl, alkynyl, ring of the cycloalkyl, ring of the cycloalkenyl, ring of the aryl, ring of the heteroaryl or ring of the heteroalicyclyl can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated with regard to an alkyl, alkenyl, alkynyl, cycloalkyl cycloalkenyl, aryl, heteroaryl or heteroalicyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, "alkynyl" refers to an alkyl group that contains in the straight or branched hydrocarbon chain one or more triple bonds. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, imidazolylalkyl and their benzo-fused analogs.

A "(heteroalicyclyl)alkyl" and "(heterocyclyl)alkyl" refer to a heterocyclic or a heteroalicyclylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl)methyl, (piperidin-4-yl)ethyl, (piperidin-4-yl)propyl, (tetrahydro-2H-thiopyran-4-yl)methyl and (1,3-thiazinan-4-yl)methyl.

"Lower alkylene groups" are straight-chained —CH$_2$— tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heteroalicyclyl, aralkyl, (heteroaryl)alkyl or (heteroalicyclyl)alkyl is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, or aryl connected, as substituents, via a carbonyl group. Examples include formyl, acetyl, propanoyl, benzoyl and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an —O-alkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

As used herein, "arylthio" refers to RS—, in which R is an aryl, such as, but not limited to, phenyl. An arylthio may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl. A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl, as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "X$_3$CSO$_2$—" group wherein each X is a halogen.

A "trihalomethanesulfonamido" group refers to an "X$_3$CS(O)$_2$N(R$_A$)—" group wherein each X is a halogen, and R$_A$ is hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl.

The term "amino" as used herein refers to a —NH$_2$ group.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—SO$_2$N(R$_A$R$_B$)" group in which R$_A$ and R$_B$ can be independently hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl. An S-sulfonamido may be substituted or unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl. An N-sulfonamido may be substituted or unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl. An O-carbamyl may be substituted or unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl. An N-carbamyl may be substituted or unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl. An O-thiocarbamyl may be substituted or unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl. An N-thiocarbamyl may be substituted or unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl. A C-amido may be substituted or unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl. An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "nucleoside" is used herein in its ordinary sense as understood by those skilled in the art, and refers to a compound composed of an optionally substituted pentose moiety or modified pentose moiety attached to a heterocyclic base or tautomer thereof via a N-glycosidic bond, such as attached via the 9-position of a purine-base or the 1-position of a pyrimidine-base. Examples include, but are not limited to, a ribonucleoside comprising a ribose moiety and a deoxyribonucleoside comprising a deoxyribose moiety. A modified pentose moiety is a pentose moiety in which an oxygen atom has been replaced with a carbon and/or a carbon has been replaced with a sulfur or an oxygen atom. A "nucleoside" is a monomer that can have a substituted base and/or sugar moiety. Additionally, a nucleoside can be incorporated into larger DNA and/or RNA polymers and oligomers. In some instances, the nucleoside can be a nucleoside analog drug.

The term "nucleotide" is used herein in its ordinary sense as understood by those skilled in the art, and refers to a nucleoside having a phosphate ester bound to the pentose moiety, for example, at the 5'-position.

As used herein, the term "heterocyclic base" refers to an optionally substituted nitrogen-containing heterocyclyl that can be attached to an optionally substituted pentose moiety or modified pentose moiety. In some embodiments, the heterocyclic base can be selected from an optionally substituted purine-base, an optionally substituted pyrimidine-base and an optionally substituted triazole-base (for example, a 1,2,4-triazole). The term "purine-base" is used herein in its ordinary sense as understood by those skilled in the art, and includes its tautomers. Similarly, the term "pyrimidine-base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine-bases include, but are not limited to, cytosine, thymine, uracil, 5,6-dihydrouracil and 5-alkylcytosine (e.g., 5-methylcytosine). An example of an optionally substituted triazole-base is 1,2,4-triazole-3-carboxamide. Other non-limiting examples of heterocyclic bases include diaminopurine, 8-oxo-$N^6$-alkyladenine (e.g., 8-oxo-$N^6$-methyladenine), 7-deazaxanthine, 7-deazaguanine, 7-deazaadenine, $N^4$,$N^4$-ethanocytosin, $N^6$,$N^6$-ethano-2,6-diaminopurine, 5-halouracil (e.g., 5-fluorouracil and 5-bromouracil), pseudoisocytosine, isocytosine, isoguanine, and other heterocyclic bases described in U.S. Pat. Nos. 5,432,272 and 7,125,855, which are incorporated herein by reference for the limited purpose of disclosing additional heterocyclic bases. In some embodiments, a heterocyclic base can be optionally substituted with an amine or an enol protecting group(s).

The term "—N-linked amino acid" refers to an amino acid that is attached to the indicated moiety via a main-chain amino or mono-substituted amino group. When the amino acid is attached in an —N-linked amino acid, one of the hydrogens that is part of the main-chain amino or mono-substituted amino group is not present and the amino acid is attached via the nitrogen. N-linked amino acids can be substituted or unsubstituted.

The term "—N-linked amino acid ester derivative" refers to an amino acid in which a main-chain carboxylic acid group has been converted to an ester group. In some embodiments, the ester group has a formula selected from alkyl-O—C(=O)—, cycloalkyl-O—C(=O)—, aryl-O—C(=O)— and aryl(alkyl)-O—C(=O)—. A non-limiting list of ester groups include substituted and unsubstituted versions of the following: methyl-O—C(=O)—, ethyl-O—C(=O)—, n-propyl-O—C(=O)—, isopropyl-O—C(=O)—, n-butyl-O—C(=O)—, isobutyl-O—C(=O)—, tert-butyl-O—C(=O)—, neopentyl-O—C(=O)—, cyclopropyl-O—C(=O)—, cyclobutyl-O—C(=O)—, cyclopentyl-O—C(=O)—, cyclohexyl-O—C(=O)—, phenyl-O—C(=O)—, benzyl-O—C(=O)— and naphthyl-O—C(=O)—. N-linked amino acid ester derivatives can be substituted or unsubstituted.

The term "—O-linked amino acid" refers to an amino acid that is attached to the indicated moiety via the hydroxy from its main-chain carboxylic acid group. When the amino acid is attached in an —O-linked amino acid, the hydrogen that is part of the hydroxy from its main-chain carboxylic acid group is not present and the amino acid is attached via the oxygen. O-linked amino acids can be substituted or unsubstituted.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

The terms "phosphorothioate" and "phosphothioate" refer to a compound of the general formula

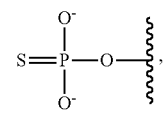

its protonated forms (for example,

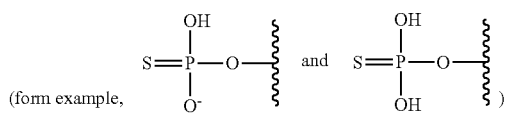 [SMILES: *OP([O-])(O)=S ; *OP(O)(O)=S]

and its tautomers (such as

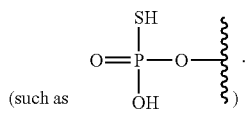 [SMILES: *OP(=O)(O)S]

As used herein, the term "phosphate" is used in its ordinary sense as understood by those skilled in the art, and includes its protonated forms (for example,

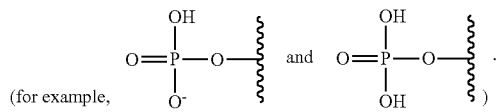

As used herein, the terms "monophosphate," "diphosphate," and "triphosphate" are used in their ordinary sense as understood by those skilled in the art, and include protonated forms.

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (BOC), acetyl, or isobutyryl); arylalkylcarbonyls and arylalkoxycarbonyls (e.g., benzyloxycarbonyl); substituted methyl ether (e.g. methoxymethyl ether); substituted ethyl ether; a substituted benzyl ether; tetrahydropyranyl ether; silyls (e.g., trimethylsilyl, triethylsilyl, triisopropylsilyl, t-butyldimethylsilyl, tri-iso-propylsilyloxymethyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g., dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4"-trimethoxytrityl (TMTr); and those described herein).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included. For example all tautomers of a phosphate and a phosphorothioate groups are intended to be included. Examples of tautomers of a phosphorothioate include the following:

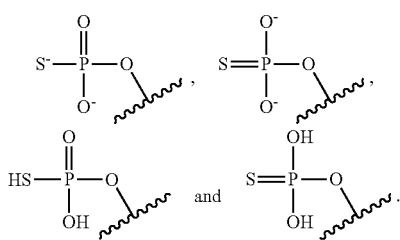

Furthermore, all tautomers of heterocyclic bases known in the art are intended to be included, including tautomers of natural and non-natural purine-bases and pyrimidine-bases.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Compounds

Some embodiments disclosed herein relate to a compound of Formula (I) or a pharmaceutically acceptable salt thereof:

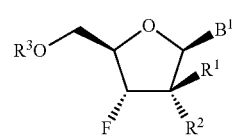

wherein: $B^1$ can be an optionally substituted

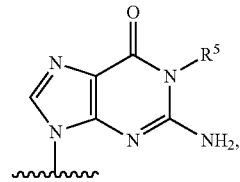

an optionally substituted

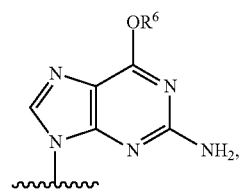

or an optionally substituted

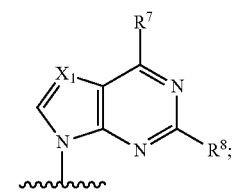

$R^1$ can be selected from an unsubstituted $C_{1-6}$ alkyl, an unsubstituted $C_{2-6}$ alkenyl, an unsubstituted $C_{2-6}$ alkynyl, an unsubstituted $C_{3-6}$ cycloalkyl and an unsubstituted $C_{1-6}$ haloalkyl; $R^2$ can be halo, —$OR^{9A}$ or —$N(R^{9B}R^{9C})$; $R^3$ can be hydrogen or

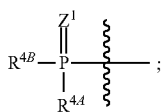

$R^{4A}$ can be selected from O—, OH, an optionally substituted N-linked amino acid and an optionally substituted N-linked amino acid ester derivative; $R^{4B}$ can be selected from O⁻, OH, an —O-optionally substituted aryl, an —O-optionally substituted heteroaryl, an —O-optionally substituted heterocyclyl, an optionally substituted N-linked amino acid, an optionally substituted N-linked amino acid ester derivative and

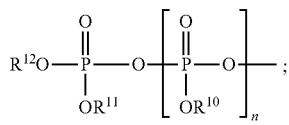

$R^5$ and $R^6$ can be independently selected from hydrogen, an unsubstituted $C_{1-6}$ alkyl, an unsubstituted $C_{3-6}$ alkenyl, an unsubstituted $C_{3-6}$ alkynyl and an unsubstituted $C_{3-6}$ cycloalkyl; $R^7$ can be $NHR^{13}$; $R^8$ can be $NHR^{14}$; $R^{9A}$ can be hydrogen or —C(=O)$R^{15}$; $R^{9B}$ and $R^{9C}$ can be independently hydrogen or an optionally substituted $C_{1-6}$ alkyl; $R^{10}$, $R^{11}$ and $R^{12}$ can be independently absent or hydrogen; $R^{13}$ can be selected from hydrogen, an optionally substituted $C_{1-6}$ alkyl, an optionally substituted $C_{3-6}$ alkenyl, an optionally substituted $C_{3-6}$ cycloalkyl, —C(=O)$R^{41}$ and —C(=O)O$R^{42}$; $R^{14}$ can be selected from hydrogen, an optionally substituted $C_{1-6}$ alkyl, an optionally substituted $C_{3-6}$ alkenyl, an optionally substituted $C_{3-6}$ cycloalkyl, —C(=O)$R^{43}$ and —C(=O)O$R^{44}$; $R^{15}$ can be an optionally substituted $C_{1-6}$ alkyl or an optionally substituted $C_{3-6}$ cycloalkyl; $X^1$ can be N or —C$R^{16}$; $R^{16}$ can be selected from hydrogen, halogen, an optionally substituted $C_{1-6}$ alkyl, an optionally substituted $C_{2-6}$ alkenyl and an optionally substituted $C_{2-6}$ alkynyl; $R^{41}$, $R^{42}$, $R^{43}$ and $R^{44}$ can be independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heteroalicyclyl, aryl($C_{1-6}$ alkyl), heteroaryl($C_{1-6}$ alkyl) and heteroalicyclyl($C_{1-6}$ alkyl); n can be 0 or 1; $Z^1$ can be O or S; and provided that when $R^3$ is

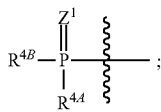

and $R^{4A}$ is O⁻ or OH, then $R^{4B}$ is O⁻, OH or

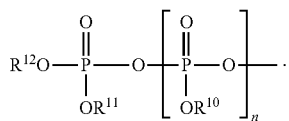

The substituents attached to the 2'-carbon can vary. In some embodiments, $R^2$ can be halo. For example, $R^2$ can be fluoro or chloro. In other embodiments, $R^2$ can be —OH. In still other embodiments, $R^2$ can be $OR^{9A}$, wherein $R^{9A}$ can be —C(=O)$R^{15}$, and $R^{15}$ can be an optionally substituted $C_{1-6}$ alkyl. Suitable alkyl groups include, but are not limited to optionally substituted variants of the following: methyl, ethyl, n-propyl, isopropyl, n-butyl, isobutyl, tert-butyl, pentyl (branched and straight-chained) and hexyl (branched and straight-chained). In yet still other embodiments, $R^2$ can be $OR^{9A}$, wherein $R^{9A}$ can be —C(=O)$R^{15}$, and $R^{15}$ can be an optionally substituted $C_{3-6}$ cycloalkyl. Suitable cycloalkyl groups include, but are not limited to optionally substituted variants of the following: cyclopropyl, cyclobutyl, cyclopentyl and cyclohexyl. In some embodiment, $R^2$ can be —N($R^{9B}R^{9C}$), wherein $R^{9B}$ and $R^{9C}$ can be independently hydrogen or an optionally substituted $C_{1-6}$ alkyl. In some embodiments, $R^{9B}$ and $R^{9C}$ can be both hydrogen. In other embodiments, at least one of $R^{9B}$ and $R^{9C}$ can be an optionally substituted $C_{1-6}$ alkyl. In some embodiments, $R^{9B}$ and $R^{9C}$ can be both an optionally substituted $C_{1-6}$ alkyl. In some embodiments, $R^{9B}$ and $R^{9C}$ can be the same. In other embodiments, $R^{9B}$ and $R^{9C}$ can be different.

In some embodiments, $R^1$ can be an unsubstituted $C_{1-6}$ alkyl. For example, $R^1$ can be unsubstituted methyl, unsubstituted ethyl, unsubstituted n-propyl, unsubstituted isopropyl, unsubstituted n-butyl, unsubstituted isobutyl, unsubstituted tert-butyl, unsubstituted pentyl (branched and straight-chained) or unsubstituted hexyl (branched and straight-chained). In some embodiments, $R^1$ can be an unsubstituted $C_{2-6}$ alkenyl. For example, $R^1$ can be ethenyl, n-propenyl, isopropenyl, n-butenyl, isobutenyl, tert-butenyl, pentenyl (branched and straight-chained), hexenyl (branched and straight-chained), vinyl or allenyl. In some embodiments, $R^1$ can be an unsubstituted alkynyl. Suitable alkynyl groups include, but are not limited to the following: ethenyl, propynyl, n-butynyl, isobutynyl-, tert-butynyl, pentynyl (branched and straight-chained) and hexynyl (branched and straight-chained). In still other embodiments, $R^1$ can be an unsubstituted $C_{3-6}$ cycloalkyl such as those described herein. In yet other embodiments, $R^1$ can be an unsubstituted haloalkyl. Examples of suitable haloalkyl include, but are not limited to, chloromethyl, fluoromethyl, difluoromethyl, trifluoromethyl, 1-chloro-2-fluoromethyl and 2-fluoroisobutyl.

In some embodiments, $R^3$ can be hydrogen. In other embodiments, $R^3$ can be

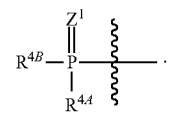

In some embodiments, the compound of Formula (I) can be a monophosphate. In other embodiments, the compound of Formula (I) can be a thiomonophosphate. In some embodiments, the compound of Formula (I) can be a diphosphate. In other embodiments, the compound of Formula (I) can be an alpha-thiodiphosphate. In some embodiments, the compound of Formula (I) can be a triphosphate. In other embodiments, the compound of Formula (I) can be an alpha-thiotriphosphate. In some embodiments, $R^{4A}$ can be O⁻ or OH; and $R^{4B}$ can be O⁻ or OH. In other embodiments, $R^{4A}$ can be O⁻ or OH; and $R^{4B}$ can be

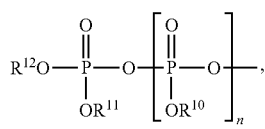

wherein $R^{10}$, $R^{11}$ and $R^{12}$ can be independently absent or hydrogen; and n can be 0. In still other embodiments, $R^{4A}$ can be $O^-$ or OH; and $R^{4B}$ can be

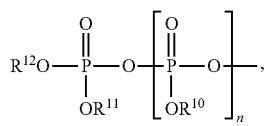

wherein $R^{10}$, $R^{11}$ and $R^{12}$ can be independently absent or hydrogen; and n can be 1. The substituents attached to the phosphorus can vary. In some embodiments, a compound of Formula (I) can be a phosphoramidate. In other embodiments, a compound of Formula (I) can be a thiophosphoramidate. In still other embodiments, a compound of Formula (I) can be a phosphorbisamidate. In yet still other embodiments, a compound of Formula (I) can be a thiophosphorbisamidate.

In some embodiments, $R^{4A}$ can be an optionally substituted N-linked amino acid. Various amino acids are suitable, including those described herein. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. In other embodiments, $R^{4A}$ can be an optionally substituted N-linked amino acid ester derivative. Examples of N-linked amino acid ester derivatives include, but are not limited to, ester derivatives of any of the following amino acids: alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of N-linked amino acid ester derivatives include, but are not limited to, an ester derivative of any of the following amino acids: alpha-ethyl-glycine, alpha-propyl-glycine and beta-alanine. In some embodiments, the N-linked amino acid ester derivative can be a $C_{1-6}$ alkyl ester derivative, for example, an isopropyl ester of alanine. In other embodiments, the N-linked amino acid ester derivative can be a $C_{3-6}$ cycloalkyl ester derivative, such as a cyclohexyl ester of alanine.

In some embodiments, $R^{4A}$ can have the structure

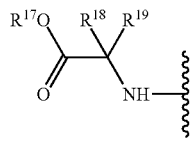

wherein $R^{17}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{18}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{19}$ can be hydrogen or an optionally substituted $C_{1-4}$-alkyl.

When $R^{18}$ is substituted, $R^{18}$ can be substituted with one or more substituents selected from N-amido, mercapto, alkylthio, an optionally substituted aryl, hydroxy, an optionally substituted heteroaryl, O-carboxy and amino. In some embodiments, $R^{18}$ can be hydrogen. In some embodiments, $R^{18}$ can be an unsubstituted $C_{1-6}$-alkyl, such as those described herein. In other embodiments, $R^{18}$ can be methyl. In some embodiments, $R^{17}$ can be an optionally substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained) and hexyl (branched and straight-chained). In some embodiments, $R^{17}$ can be methyl or isopropyl. In some embodiments, $R^{17}$ can be ethyl or neopentyl. In other embodiments, $R^{17}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl and cyclohexyl. In some embodiments, $R^{17}$ can be an optionally substituted cyclohexyl. In still other embodiments, $R^{17}$ can be an optionally substituted aryl, such as phenyl and naphthyl. In yet still other embodiments, $R^{17}$ can be an optionally substituted aryl($C_{1-6}$ alkyl). In some embodiments, $R^{17}$ can be an optionally substituted benzyl. In some embodiments, $R^{17}$ can be an optionally substituted $C_{1-6}$ haloalkyl, for example, $CF_3$. In some embodiments, $R^{19}$ can be hydrogen. In other embodiments, $R^{19}$ can be an optionally substituted $C_{1-4}$-alkyl, such as methyl, ethyl, n-propyl, isopropyl, n-butyl, isobutyl or tert-butyl. In some embodiments, $R^{19}$ can be methyl. Depending on the groups that are selected for $R^{18}$ and $R^{19}$, the carbon to which $R^{18}$ and $R^{19}$ are attached may be a chiral center. In some embodiment, the carbon to which $R^{18}$ and $R^{19}$ are attached may be a (R)-chiral center. In other embodiments, the carbon to which $R^{18}$ and $R^{19}$ are attached may be a (S)-chiral center.

Examples of suitable

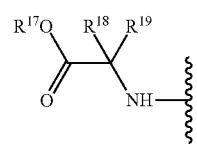

groups include the following:

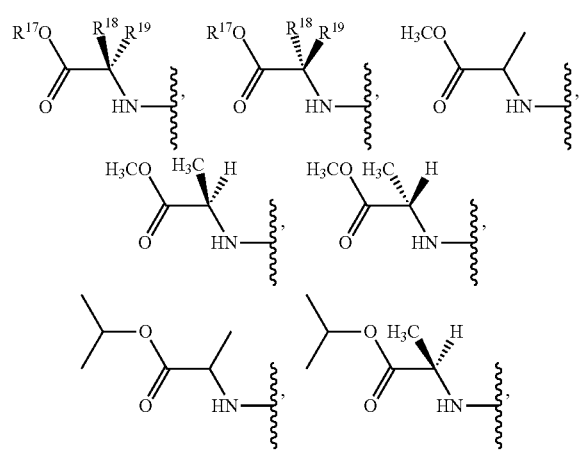

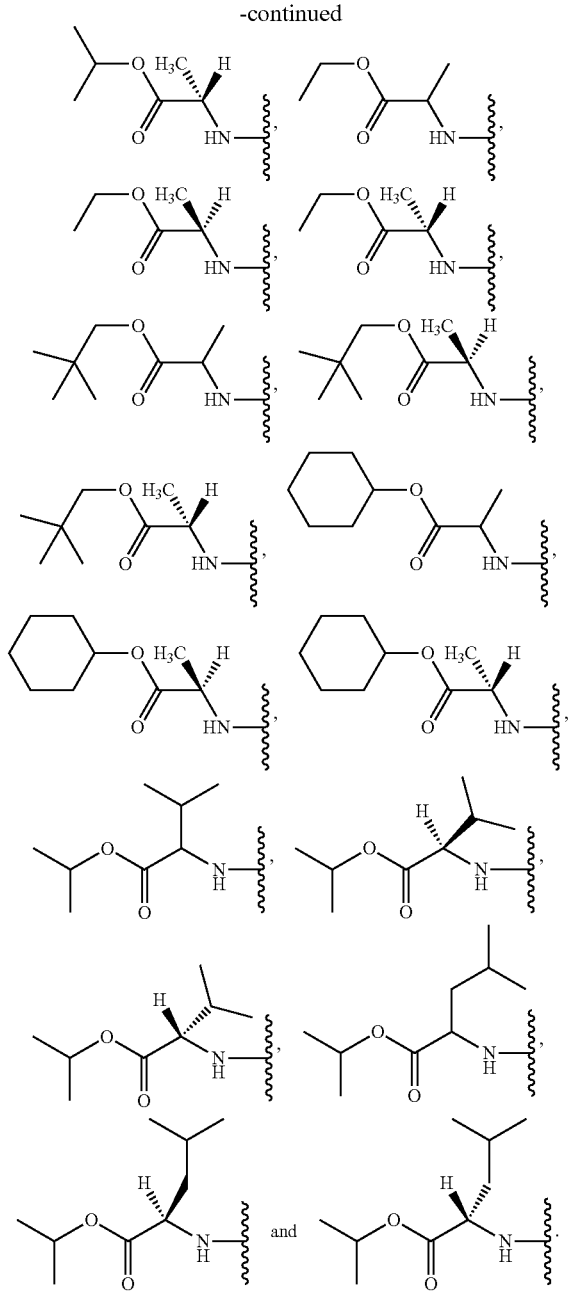

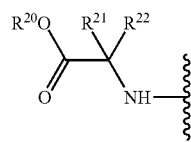

embodiments, $R^{4B}$ can have the structure wherein $R^{20}$ can be selected from hydrogen, an optionally substituted $C_{1-6}$-alkyl, an optionally substituted $C_{3-6}$ cycloalkyl, an optionally substituted aryl, an optionally substituted aryl($C_{1-6}$ alkyl) and an optionally substituted haloalkyl; $R^{21}$ can be selected from hydrogen, an optionally substituted $C_{1-6}$ alkyl, an optionally substituted $C_{1-6}$ haloalkyl, an optionally substituted $C_{3-6}$ cycloalkyl, an optionally substituted $C_6$ aryl, an optionally substituted $C_{10}$ aryl and an optionally substituted aryl($C_{1-6}$ alkyl); and $R^{22}$ can be hydrogen or an optionally substituted $C_{1-4}$-alkyl.

When $R^{21}$ is substituted, $R^{21}$ can be substituted with one or more substituents selected from N-amido, mercapto, alkylthio, an optionally substituted aryl, hydroxy, an optionally substituted heteroaryl, O-carboxy and amino. In some embodiments, $R^{21}$ can be an unsubstituted $C_{1-6}$-alkyl, such as those described herein. In some embodiments, $R^{21}$ can be hydrogen. In other embodiments, $R^{21}$ can be methyl. In some embodiments, $R^{20}$ can be an optionally substituted $C_{1-6}$ alkyl. Examples of optionally substituted $C_{1-6}$ alkyls include optionally substituted variants of the following: methyl, ethyl, n-propyl, isopropyl, n-butyl, isobutyl, tert-butyl, pentyl (branched and straight-chained) and hexyl (branched and straight-chained). In some embodiments, $R^{20}$ can be methyl or isopropyl. In some embodiments, $R^{20}$ can be ethyl or neopentyl. In other embodiments, $R^{20}$ can be an optionally substituted $C_{3-6}$ cycloalkyl. Examples of optionally substituted $C_{3-6}$ cycloalkyl include optionally substituted variants of the following: cyclopropyl, cyclobutyl, cyclopentyl and cyclohexyl. In an embodiment, $R^{20}$ can be an optionally substituted cyclohexyl. In still other embodiments, $R^{20}$ can be an optionally substituted aryl, such as phenyl and naphthyl. In yet still other embodiments, $R^{20}$ can be an optionally substituted aryl($C_{1-6}$ alkyl). In some embodiments, $R^{20}$ can be an optionally substituted benzyl. In some embodiments, $R^{20}$ can be an optionally substituted $C_{1-6}$ haloalkyl, for example, $CF_3$. In some embodiments, $R^{22}$ can be hydrogen. In other embodiments, $R^{22}$ can be an optionally substituted $C_{1-4}$-alkyl, such as methyl, ethyl, n-propyl, isopropyl, n-butyl, isobutyl or tert-butyl. In an embodiment, $R^{22}$ can be methyl. Depending on the groups that are selected for $R^{21}$ and $R^{22}$, the carbon to which $R^{21}$ and $R^{22}$ are attached may be a chiral center. In some embodiment, the carbon to which $R^{21}$ and $R^{22}$ are attached may be a (R)-chiral center. In other embodiments, the carbon to which $R^{21}$ and $R^{22}$ are attached may be a (S)-chiral center.

Examples of suitable

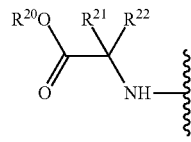

In some embodiments, $R^{4B}$ can be an —O-optionally substituted aryl. For example, $R^{4B}$ can be an —O-optionally substituted phenyl. When the phenyl is substituted, the ring can be substituted 1, 2, 3 or more than 3 times. Suitable mono-substituted phenyl groups include, ortho-substituted phenyl, meta-substituted phenyl and para-substituted phenyl. In some embodiments, $R^{4B}$ can be ortho-chlorophenyl. In some embodiments, $R^{4B}$ can be 3-chloro-4-fluorophenyl. Alternatively, $R^{4B}$ can be an —O-optionally substituted naphthyl. In other embodiments, $R^{4B}$ can be an —O-optionally substituted heteroaryl. In still other embodiments, $R^{4B}$ can be an —O-optionally substituted heterocyclyl.

In some embodiments, $R^{4B}$ can be an optionally substituted N-linked amino acid, such as those described for $R^{4A}$. In other embodiments, $R^{4B}$ can be an optionally substituted N-linked amino acid ester derivative, for example, those described herein. In some groups include the following:

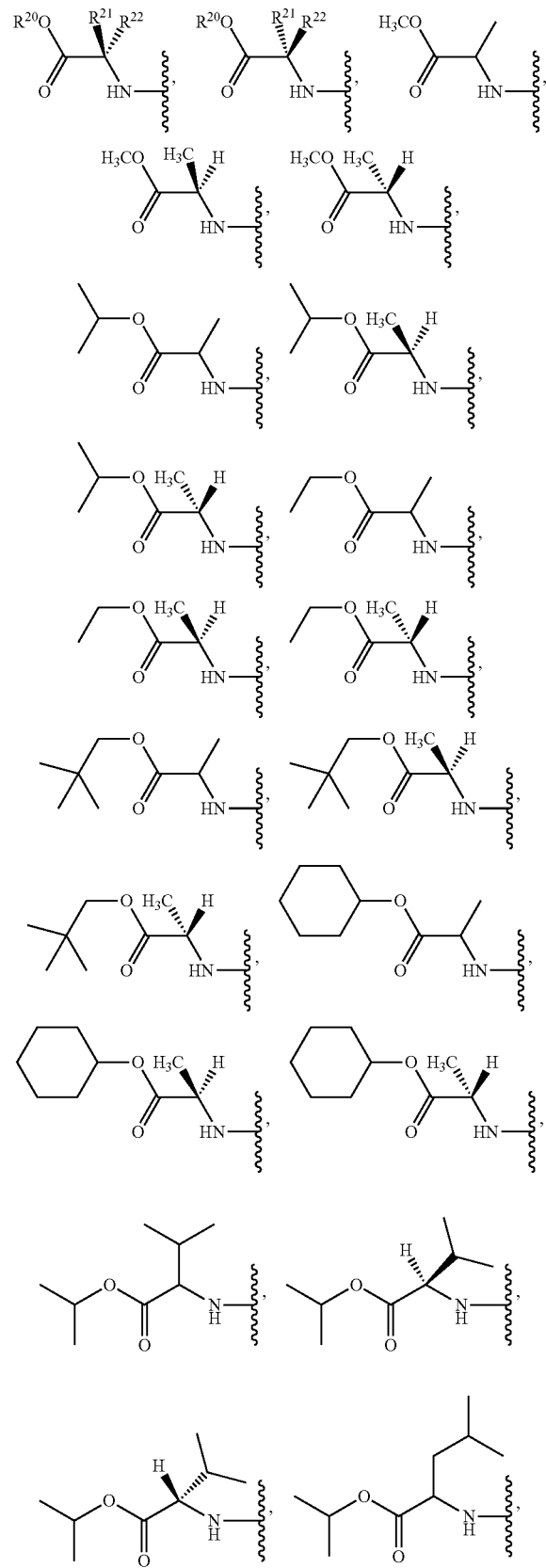

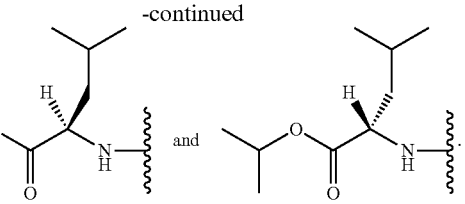

In some embodiments, $R^{4A}$ can be an optionally substituted N-linked amino acid or an optionally substituted N-linked amino acid ester derivative and $R^{4B}$ can be an —O-optionally substituted aryl. In other embodiments, $R^{4A}$ can be an optionally substituted N-linked amino acid or an optionally substituted N-linked amino acid ester derivative and $R^{4B}$ can be an —O-optionally substituted heteroaryl. In some embodiments, $R^{4A}$ can be an optionally substituted N-linked amino acid or an optionally substituted N-linked amino acid ester derivative and $R^{4B}$ can be an optionally substituted N-linked amino acid or an optionally substituted N-linked amino acid ester derivative. In some embodiments, $R^{4A}$ and $R^{4B}$ can be the same. In other embodiments, $R^{4A}$ and $R^{4B}$ can be different.

The nucleobase can vary. In some embodiments, $B^1$ can be guanine. In some embodiments, $B^1$ can be an optionally substituted

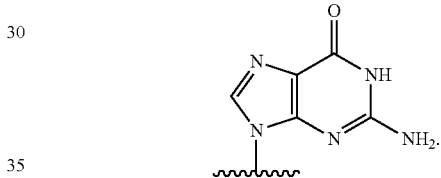

In other embodiments, $B^1$ can be an optionally substituted

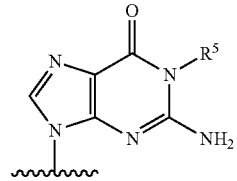

wherein $R^5$ can be selected from hydrogen, an unsubstituted $C_{1-6}$ alkyl, an unsubstituted $C_{3-6}$ alkenyl, an unsubstituted $C_{3-6}$ alkynyl and an unsubstituted $C_{3-6}$ cycloalkyl. In some embodiments, $B^1$ can be unsubstituted

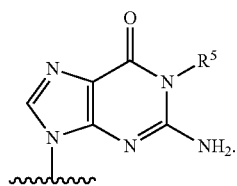

In some embodiments, $R^5$ can be an unsubstituted $C_{1-6}$ alkyl. For example, $R^5$ can be methyl, ethyl, n-propyl, isopropyl, n-butyl, isobutyl, tert-butyl, pentyl (branched and straight-chained) or hexyl (branched and straight-chained). In some embodiments, $R^5$ can be an unsubstituted $C_{3-6}$ alkenyl. In other embodiments, $R^5$ can be an unsubstituted $C_{3-6}$ alkynyl. In still other embodiments, $R^5$ can be an unsubstituted $C_{3-6}$ cycloalkyl, for example, cyclopropyl, cyclobutyl, cyclopentyl or cyclohexyl.

In some embodiments, $B^1$ can be an optionally substituted

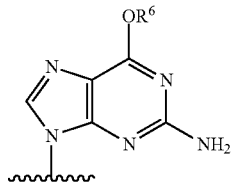

wherein $R^6$ can be selected from hydrogen, an unsubstituted $C_{1-6}$ alkyl, an unsubstituted $C_{3-6}$ alkenyl, an unsubstituted $C_{3-6}$ alkynyl and an unsubstituted $C_{3-6}$ cycloalkyl. In some embodiments, $B^1$ can be unsubstituted

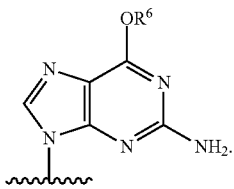

In some embodiments, $R^6$ can be hydrogen. In some embodiments, $R^6$ can be an unsubstituted $C_{1-6}$ alkyl. For example, $R^6$ can be methyl, ethyl, n-propyl, isopropyl, n-butyl, isobutyl, tert-butyl, pentyl (branched and straight-chained) or hexyl (branched and straight-chained). In some embodiments, $R^6$ can be an ethyl. In some embodiments, $R^6$ can be an unsubstituted $C_{3-6}$ alkenyl. In other embodiments, $R^6$ can be an unsubstituted $C_{3-6}$ alkynyl. In other embodiments, $R^6$ can be an unsubstituted $C_{3-6}$ cycloalkyl, for example, cyclopropyl, cyclobutyl, cyclopentyl or cyclohexyl.

In some embodiments, $B^1$ can be an optionally substituted

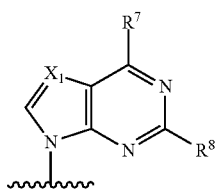

wherein $X^1$ can be N or —$CR^{16}$; $R^{16}$ can be selected from hydrogen, halogen, an optionally substituted $C_{1-6}$ alkyl, an optionally substituted $C_{2-6}$ alkenyl and an optionally substituted $C_{2-6}$ alkynyl; $R^7$ can be $NHR^{13}$; $R^8$ can be $NHR^{14}$; $R^{13}$ can be selected from hydrogen, an optionally substituted $C_{1-6}$ alkyl, an optionally substituted $C_{3-6}$ alkenyl, an optionally substituted $C_{3-6}$ cycloalkyl, —C(=O)$R^{41}$ and —C(=O)O$R^{42}$; $R^{14}$ can be selected from hydrogen, an optionally substituted $C_{1-6}$ alkyl, an optionally substituted $C_{3-6}$ alkenyl, an optionally substituted $C_{3-6}$ cycloalkyl, —C(=O)$R^{43}$ and —C(=O)O$R^{44}$; $R^{41}$, $R^{42}$, $R^{43}$ and $R^{44}$ can be independently selected from $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heteroalicyclyl, aryl($C_{1-6}$ alkyl), heteroaryl($C_{1-6}$ alkyl) and heteroalicyclyl($C_{1-6}$ alkyl). In other embodiments, $B^1$ can be an unsubstituted

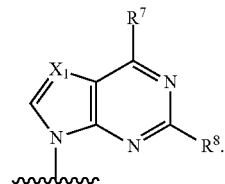

In some embodiments, $X^1$ can be N (nitrogen). In other embodiments, $X^1$ can be —$CR^{16}$, wherein $R^{16}$ can be selected from hydrogen, halogen, an optionally substituted $C_{1-6}$ alkyl, an optionally substituted $C_{2-6}$ alkenyl and an optionally substituted $C_{2-6}$ alkynyl. In some embodiments, $X^1$ can be CH. In some embodiments, $R^7$ and $R^8$ can be both $NH_2$. In other embodiments, at least one of $R^7$ and $R^8$ can be $NH_2$. In some embodiments, $R^7$ can be $NHR^{13}$, wherein $R^{13}$ can be an optionally substituted $C_{1-6}$ alkyl. In some embodiments, $R^8$ can be $NHR^{14}$, wherein $R^{14}$ can be an optionally substituted $C_{1-6}$ alkyl. In other embodiments, $R^7$ can be $NHR^{13}$, wherein $R^{13}$ can be selected from an optionally substituted $C_{3-6}$ alkenyl, an optionally substituted $C_{3-6}$ cycloalkyl, —C(=O)$R^{41}$ and —C(=O)O$R^{42}$. In other embodiments, $R^8$ can be $NHR^{14}$, wherein $R^{14}$ can be selected from an optionally substituted $C_{3-6}$ alkenyl, an optionally substituted $C_{3-6}$ cycloalkyl, —C(=O)$R^{43}$ and —C(=O)O$R^{44}$. In some embodiments, $R^7$ and $R^8$ can be the same. In other embodiments, $R^7$ and $R^8$ can be different. In some embodiments, $B^1$ can be 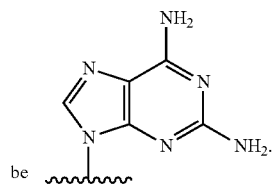 [SMILES: *n1cnc2c(N)nc(N)nc21]

In some embodiments, $Z^1$ can be O (oxygen). In other embodiments, $Z^1$ can be S (sulfur).

Some examples of compounds of Formula (I) include, but are not limited to the following:

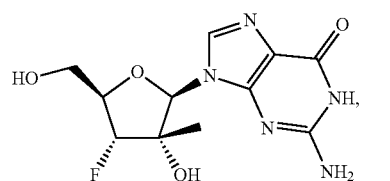

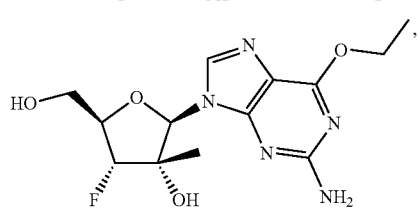

-continued

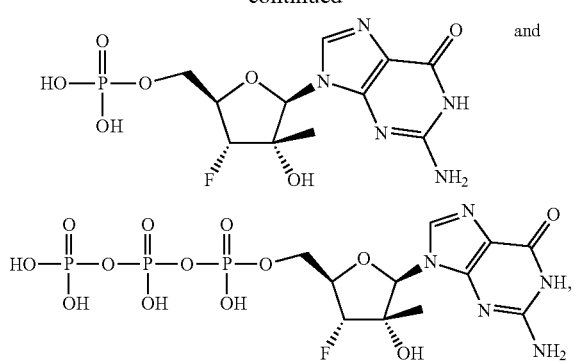

or a pharmaceutically acceptable salt of the foregoing.

Further examples of compounds of Formula (I) include, but are not limited to the following:

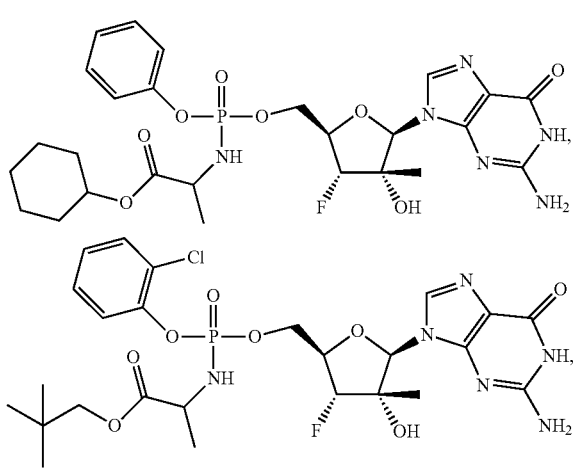

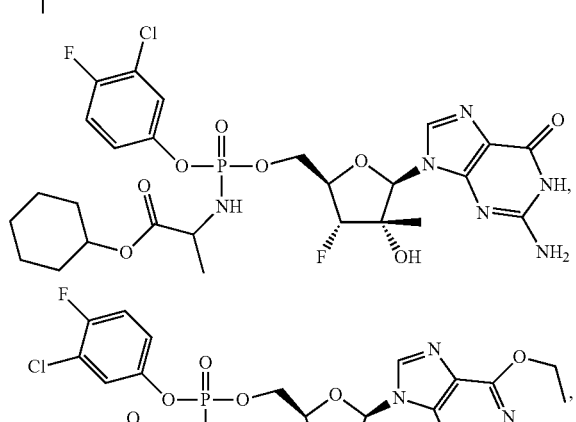

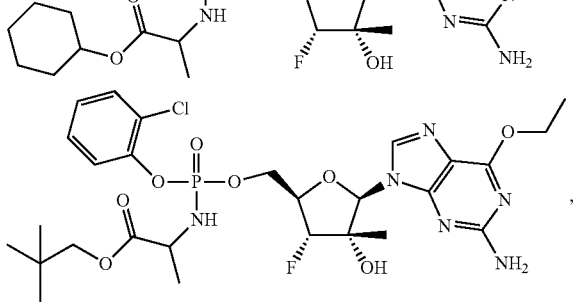

-continued

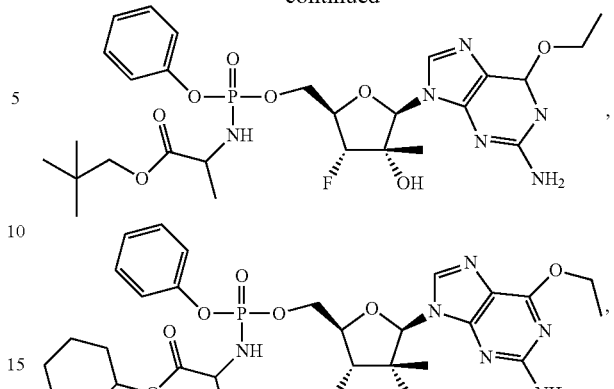

or a pharmaceutically acceptable salt of the foregoing.

As described herein, a compound of Formula (I), or a pharmaceutically acceptable salt thereof, can have $R^3$ being

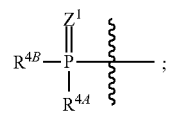

$R^{4A}$ being an optionally substituted N-linked amino acid or an optionally substituted N-linked amino acid ester derivative; and $R^{4B}$ being an —O-optionally substituted aryl, an —O-optionally substituted heteroaryl, an —O-optionally substituted heterocyclyl, an optionally substituted N-linked amino acid or an optionally substituted N-linked amino acid ester derivative. By neutralizing the charge on the phosphate or thiophosphate, penetration of the cell membrane may be facilitated as a result of the increased lipophilicity of the compound. Once absorbed and taken inside the cell, the groups attached to the phosphorus can be easily removed by esterases, proteases and/or other enzymes. In some embodiments, the groups attached to the phosphorus can be removed by simple hydrolysis. Inside the cell, the phosphate thus released may then be metabolized by cellular enzymes to the diphosphate or the active triphosphate. Likewise, the thio-phosphate may be metabolized to the alpha-thiodiphosphate or the alpha-thiotriphosphate. Furthermore, in some embodiments, varying the substituents on a compound described herein, such as compound of Formula (I), can help maintain the efficacy of such the compound by reducing undesirable effects, such as isomerization.

In some embodiments, the phosphorylation of a thio-monophosphate of a compound of Formula (I), or pharmaceutically acceptable salt thereof, can be stereoselective. For example, a thio-monophosphate of a compound of Formula (I) can be phosphorylated to give an alpha-thiodiphosphate and/or an alpha-thiotriphosphate compound that can be enriched in the (R) or (S) diastereomer with respect to the 5'-O-phosphorous atom. For example, one of the (R) and (S) configuration with respect to the 5'-O-phosphorous atom of the alpha-thiodiphosphate and/or the alpha-thiotriphosphate compound can be present in an amount >50%, ≥75%, ≥90%, ≥95% or ≥99% compared to the amount of the other of the (R) or (S) configuration with respect to the 5'-O-phosphorous atom. In some embodiments, phosphorylation of a compound of Formula (I), or pharmaceutically acceptable salt thereof, can result in the formation of a compound that has the (R)-configuration at the 5'-O-phosphorous atom. In some embodiments, phosphorylation of a compound of Formula (I), or pharmaceutically acceptable salt thereof, can result in formation of a compound that has the (S)-configuration at the 5'-O-phosphorous atom.

In some embodiments, a compound of Formula (I), or a pharmaceutically acceptable salt thereof, can act as a chain terminator of HCV replication. For example, since compounds of Formula (I) do not contain a hydroxyl group at the 3'-position, once the compound is incorporated into an RNA chain no further chain elongation can occur.

In some embodiments, a compound of Formula (I), or a pharmaceutically acceptable salt thereof, can have increased metabolic and/or plasma stability. In some embodiments, a compound of Formula (I), or a pharmaceutically acceptable salt thereof, can be more resistant to hydrolysis and/or more resistant to enzymatic transformations. For example, a compound of Formula (I), or a pharmaceutically acceptable salt thereof, can have increased metabolic stability, increased plasma stability, can be more resistant to hydrolysis and/or can be more resistant to enzymatic transformations compared to a compound that is identical in structure but for having a OH group in place of the fluoro at the 3'-position. In some embodiments, a compound of Formula (I), or a pharmaceutically acceptable salt thereof, can have improved properties. A non-limiting list of example properties include, but are not limited to, increased biological half-life, increased bioavailability, increase potency, a sustained in vivo response, increased dosing intervals, decreased dosing amounts, decreased cytotoxicity, reduction in required amounts for treating disease conditions, reduction in viral load, reduction in time to seroconversion (i.e., the virus becomes undetectable in patient serum), increased sustained viral response, a reduction of morbidity or mortality in clinical outcomes, increased subject compliance, decreased liver conditions (such as liver fibrosis, liver cirrhosis and/or liver cancer), and compatibility with other medications. In some embodiments, a compound of Formula (I), or a pharmaceutically acceptable salt thereof, can have a biological half-life of greater than 24 hours. In some embodiments, a compound of Formula (I), or a pharmaceutically acceptable salt thereof, can have a biological half-life greater than a compound that is identical in structure but for having a OH group in place of the fluoro at the 3'-position. In some embodiments, a compound of Formula (I), or a pharmaceutically acceptable salt thereof, can have more potent antiviral activity (for example, a lower $EC_{50}$ in an HCV replicon assay) as compared to the current standard of care. In some embodiments, a compound of Formula (I), or a pharmaceutically acceptable salt thereof, does not significantly inhibit mitochondrial function of the mitochondrial RNA polymerase. For example, a compound of Formula (I), or a pharmaceutically acceptable salt thereof, is incorporated in the human mitochondrial RNA polymerase less than 10% compared to the natural 5'-triphosphate nucleotide with the same $B^1$.

Additionally, in some embodiments, the presence of a thiophosphoramidate, phosphoramidate, thiophosphorbisamidate or phosphorbisamidate in a compound of Formula (I) can increase the stability of the compound by inhibiting its degradation. Also, in some embodiments, the presence of a thiophosphoramidate, phosphoramidate, thiophosphorbisamidate or phosphorbisamidate can make the compound more resistant to cleavage in vivo and provide sustained, extended efficacy. In some embodiments, a thiophosphoramidate, phosphoramidate, thiophosphorbisamidate or phosphorbisamidate can facilitate the penetration of the cell membrane by a compound of Formula (I) by making the compound more lipophilic. In some embodiments, a thiophosphoramidate, phosphoramidate, thiophosphorbisamidate or phosphorbisamidate can have improved oral bioavailability, improved aqueous stability and/or reduced risk of byproduct-related toxicity. In some embodiments, for comparison purposes, a compound of Formula (I) can be compared to a compound that is identical in structure but for having a OH group in place of the fluoro at the 3'-position.

Synthesis

Compounds of Formula (I) and those described herein may be prepared in various ways. General synthetic routes to the compound of Formula (I), and some examples of starting materials used to synthesize the compounds of Formula (I) are shown in Schemes 1 and 2, and described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Compounds of Formula (I) can be prepared using various methods known to those skilled in the art. Examples of methods are shown in Schemes 1 and 2. Suitable phosphorus containing precursors can be commercially obtained or prepared by synthetic methods known to those skilled in the art. Examples of general structures of phosphorus containing precursors are shown in Schemes 1 and 2, and include phosphorochloridates and thiophosphorochloridates. Suitable phosphorochloridates and thiophosphorochloridates are commercially available and/or can be synthetically prepared.

Scheme 1

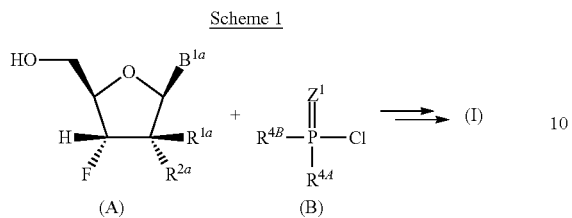

One method for forming a compound of Formula (I) is shown in Scheme 1. In Scheme 1, $R^{1a}$, $R^{2a}$ and $B^{1a}$ can be the same as $R^1$, $R^2$ and $B^1$ as described herein for Formula (I). In some embodiments, a compound of Formula (I) can be generated from a compound of Formula (A) and a compound of Formula (B) using an organometallic reagent, such as a Grignard reagent. Suitable Grignard reagents are known to those skilled in the art and include, but are not limited to, alkylmagnesium chlorides and alkylmagnesium bromides. In other embodiments, an appropriate base can be used to form a compound of Formula (I). Examples of suitable bases include, but are not limited to, an amine base, such as an alkylamine (including mono-, di- and tri-alkylamines (e.g., triethylamine)), optionally substituted pyridines (e.g. collidine) and optionally substituted imidazoles (e.g., N-methylimidazole)).

When compounds of Formula (I) has $Z^1$ being sulfur, the sulfur can be added in various manners. In some embodiments, the sulfur can be part of the phosphorus containing precursor, for example,

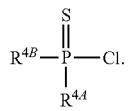

Alternatively, one of the oxygens attached to the phosphorus can be exchanged with a sulfur using a sulfurization reagent. Suitable sulfurization agents are known to those skilled in the art, and include, but are not limited to, elemental sulfur, Lawesson's reagent, cyclooctasulfur, 3H-1,2-Benzodithiole-3-one-1,1-dioxide (Beaucage's reagent), 3-((N,N-dimethylaminomethylidene)amino)-3H-1,2,4-dithiazole-5-thione (DDTT) and bis(3-triethoxysilyl)propyl-tetrasulfide (TEST).

Scheme 2

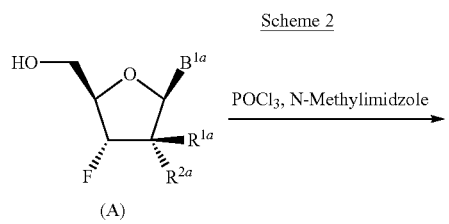

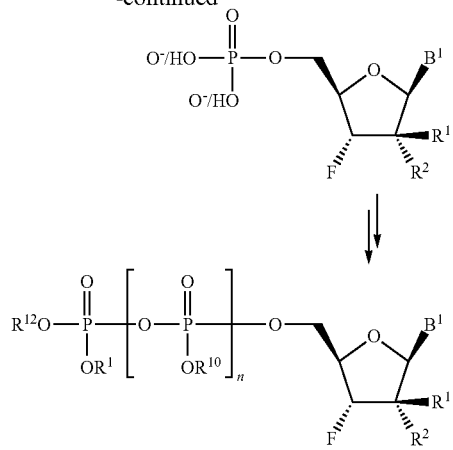

A phosphorus containing precursor can be coupled to the nucleoside, for example, a compound of Formula (A). Following the coupling of the phosphorus containing precursor, any leaving groups can be cleaved under suitable conditions, such as hydrolysis. In Scheme 2, $R^{1a}$, $R^{2a}$ and $B^{1a}$ can be the same as $R^1$, $R^2$ and $B^1$ as described herein for Formula (I). Further phosphorus containing groups can be added using methods known to those skilled in the art, for example using a pyrophosphate. If desired, one or more bases can be used during the addition of each phosphorus-containing group. Examples of suitable bases are described herein.

As provided herein, $R^2$ can be —OC(=O)$R^{15}$. The —OC(=O)$R^{15}$ group can be formed at the 2'-position using various methods known to those skilled in the art. As an example, a compound of Formula (I), wherein $R^2$ is a hydroxy group, can be treated with an alkyl anhydride (e.g., acetic anhydride and propionic anhydride) or an alkyl acid chloride (e.g., acetylchloride). If desired, a catalyst can be used to facilitate the reaction. An example of suitable catalyst is 4-dimethylaminopyridine (DMAP). Alternatively, the —OC(=O)$^{15}$ group can be formed at the 2'-position by reacting an alkyl acid (e.g. acetic acid and propionic acid) in the presences of a carbodiimide or a coupling reagent. Examples of carbodiimides include, but are not limited to, N,N'-dicyclohexylcarbodiimide (DCC), N,N'-diisopropylcarbodiimide (DIC) and 1-ethyl-3-(3-dimethylaminopropyl)carbodiimide (EDC).

To reduce the formation of side products, one or more the groups attached to the pentose ring can be protected with one or more suitable protecting groups. As an example, if $R^2$ is a hydroxy group, the hydroxy group can be protected with a suitable protecting group, such as triarylmethyl and/or silyl group. Examples of triarylmethyl groups include but are not limited to, trityl, monomethoxytrityl (MMTr), 4,4'-dimethoxytrityl (DMTr), 4,4',4''-trimethoxytrityl (TMTr), 4,4',4''-tris-(benzoyloxy)trityl (TBTr), 4,4',4''-tris(4,5-dichlorophthalimido)trityl (CPTr), 4,4',4''-tris(levulinyloxy)trityl (TLTr), p-anisyl-1-naphthylphenylmethyl, di-o-anisyl-1-naphthylmethyl, p-tolyldipheylmethyl, 3-(imidazolylmethyl)-4,4'-dimethoxytrityl, 9-phenylxanthen-9-yl (Pixyl), 9-(p-methoxyphenyl)xanthen-9-yl (Mox), 4-decyloxytrityl, 4-hexadecyloxytrityl, 4,4'-dioctadecyltrityl, 9-(4-octadecyloxyphenyl)xanthen-9-yl, 1,1'-bis-(4-methoxyphenyl)-1'-pyrenylmethyl, 4,4',4''-tris-(tert-butylphenyl)methyl (TTTr) and 4,4'-di-3,5-hexadienoxytrityl. Examples of suitable silyl groups are described herein and include trimethylsilyl (TMS), tert-butyldimethylsilyl (TBDMS), triisopropylsilyl (TIPS), tert-butyldiphenylsilyl (TBDPS), tri-iso-propylsilyloxymethyl and [2-(trimethylsilyl)ethoxy]methyl.

Pharmaceutical Compositions

Some embodiments described herein relates to a pharmaceutical composition, that can include a therapeutically effective amount of one or more compounds described herein (e.g., a compound of Formula (I)), or a pharmaceutically acceptable salt thereof) and a pharmaceutically acceptable carrier, diluent, excipient or combination thereof. In some embodiments, the pharmaceutical composition can include a single diastereomer of a compound of Formula (I), or a pharmaceutically acceptable salt thereof, (for example, a single diastereomer is present in the pharmaceutical composition at a concentration of greater than 99% compared to the total concentration of the other diastereomers). In other embodiments, the pharmaceutical composition can include a mixture of diastereomers of a compound of Formula (I), or a pharmaceutically acceptable salt thereof. For example, the pharmaceutical composition can include a concentration of one diastereomer of >50%, ≥60%, ≥70%, ≥80%, ≥90%, ≥95%, or ≥98%, as compared to the total concentration of the other diastereomers. In some embodiments, the pharmaceutical composition includes a 1:1 mixture of two diastereomers of a compound of Formula (I), or a pharmaceutically acceptable salt thereof.

The term "pharmaceutical composition" refers to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

Methods of Use

Some embodiments disclosed herein relate to a method of treating and/or ameliorating a disease or condition that can include administering to a subject a therapeutically effective amount of one or more compounds described herein, such as a compound of Formula (I), or a pharmaceutically acceptable salt thereof, or a pharmaceutical composition that includes a compound described herein, or a pharmaceutically acceptable salt thereof. Other embodiments disclosed herein relate to a method of treating and/or ameliorating a disease or condition that can include administering to a subject identified as suffering from the disease or condition a therapeutically effective amount of one or more compounds described herein, such as a compound of Formula (I), or a pharmaceutically acceptable salt thereof, or a pharmaceutical composition that includes a compound described herein, or a pharmaceutically acceptable salt thereof.

Some embodiments disclosed herein relates to a method of ameliorating or treating a HCV infection that can include administering to a subject identified as suffering from a HCV infection a therapeutically effective amount of one or more compounds described herein (for example, a compound of Formula (I)), or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for ameliorating and/or treating a HCV infection that can include administering to a subject identified as suffering from a HCV infection a therapeutically effective amount of one or more compounds described herein. Still other embodiments described herein relate to one or more compounds described herein, or a pharmaceutically acceptable salt of a compound described herein, that can be used for ameliorating and/or treating a HCV infection by administering to a subject identified as suffering from a HCV infection a therapeutically effective amount of one or more compounds described herein.

Some embodiments disclosed herein relate to methods of ameliorating and/or treating a HCV infection that can include contacting a cell infected with the hepatitis C virus with an effective amount of one or more compounds described herein, or a pharmaceutically acceptable salt of a compound described herein, or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for ameliorating and/or treating a HCV infection that can include contacting a cell infected with the hepatitis C virus with an effective amount of said compound(s). Still other embodiments described herein relate to one or more compounds described herein, or a pharmaceutically acceptable salt of a compound described herein, that can be used for ameliorating and/or treating a HCV infection by contacting a cell infected with the hepatitis C virus with an effective amount of said compound(s).

Some embodiments disclosed herein relate to methods of inhibiting replication of a hepatitis C virus that can include contacting a cell infected with the hepatitis C virus with an effective amount of one or more compounds described herein, or a pharmaceutically acceptable salt of a compound described herein, or a pharmaceutical composition that includes one or more compounds described herein, or a pharmaceutically acceptable salt thereof. Other embodiments described herein relate to using one or more compounds described herein, or a pharmaceutically acceptable salt of a compound described herein, in the manufacture of a medicament for inhibiting replication of a hepatitis C virus that can include contacting a cell infected with the hepatitis C virus with an effective amount of said compound(s). Still other embodiments described herein relate to a compound described herein, or a pharmaceutically acceptable salt of a compound described herein, that can be used for inhibiting replication of a hepatitis C virus by contacting a cell infected with the hepatitis C virus with an effective amount of said compound(s). In some embodiments, the compound of Formula (I), or a pharmaceutical acceptable salt thereof, that can be used to ameliorating and/or treating a viral infection (for example, a HCV infection) and/or inhibit replication of a virus (such as a HCV virus) can be any of the embodiments provided in any of the embodiments described in paragraphs [0090]-[0108].

In some embodiments, the compound can be a compound of Formula (I), or a pharmaceutical acceptable salt thereof, wherein $R^3$ is hydrogen. In other embodiments, the compound can be a compound of Formula (I), wherein compound of Formula (I) is a mono, di, or triphosphate, or a pharmaceutically acceptable salt of the foregoing. In still other embodiments, the compound can be a compound of Formula (I), wherein compound of Formula (I) is a thiomonophosphate, alpha-thiodiphosphate, or alpha-thiotriphosphate, or a pharmaceutically acceptable salt of the foregoing. In yet still other embodiments, the compound can be a compound of Formula (I), wherein compound of Formula (I) is phosphoramidate or phosphorbisamidate, or a pharmaceutically acceptable salt of the foregoing. In some embodiments, the compound can be a compound of Formula (I), wherein compound of Formula (I) is thiophosphoramidate or thiophosphorbisamidate, or a pharmaceutically acceptable salt of the foregoing.

HCV is an enveloped positive strand RNA virus in the Flaviviridae family. There are various nonstructural proteins of HCV, such as NS2, NS3, NS4, NS4A, NS4B, NS5A and NS5B. NS5B is believed to be an RNA-dependent RNA polymerase involved in the replication of HCV RNA.

Some embodiments described herein relate to a method of inhibiting NS5B polymerase activity that can include contacting a cell infected with hepatitis C virus with an effective amount of a compound of Formula (I), or a pharmaceutical acceptable salt thereof. Some embodiments described herein relate to a method of inhibiting NS5B polymerase activity that can include administering to a subject infected with hepatitis C virus an effective amount of a compound of Formula (I), or a pharmaceutical acceptable salt thereof. In some embodiments, a compound of Formula (I), or a pharmaceutically acceptable salt thereof, can inhibit a RNA dependent RNA polymerase, and thus, inhibit the replication of HCV RNA. In some embodiments, a compound of Formula (I), or a pharmaceutically acceptable salt thereof, can inhibit a HCV polymerase (for example, NS5B polymerase).

Some embodiments described herein relate to a method of treating a condition selected from liver fibrosis, liver cirrhosis and liver cancer in a subject suffering from one or more of the aforementioned liver conditions that can include administering to the subject an effective amount of a compound or a pharmaceutical composition described herein (for example, a compound of Formula (I), or a pharmaceutical acceptable salt thereof), wherein the liver condition is caused by a HCV infection. Some embodiments described herein relate to a method of increasing liver function in a subject having a HCV infection that can include administering to the subject an effective amount of a compound or a pharmaceutical composition described herein (for example, a compound of Formula (I), or a pharmaceutical acceptable salt thereof). Also contemplated is a method for reducing or eliminating further virus-caused liver damage in a subject having an HCV infection by administering to the subject an effective amount of a compound or a pharmaceutical composition described herein (for example, a compound of Formula (I), or a pharmaceutical acceptable salt thereof). In some embodiments, this method can include slowing or halting the progression of liver disease. In other embodiments, the course of the disease can be reversed, and stasis or improvement in liver function is contemplated. In some embodiments, liver fibrosis, liver cirrhosis and/or liver cancer can be treated; liver function can be increased; virus-caused liver damage can be reduced or eliminated; progression of liver disease can be slowed or halted; the course of the liver disease can be reversed and/or liver function can be improved or maintained by contacting a cell infected with hepatitis C virus with an effective amount of a compound described herein (for example, a compound of Formula (I), or a pharmaceutically acceptable salt thereof.)

There are a variety of genotypes of HCV, and a variety of subtypes within each genotype. For example, at present it is known that there are eleven (numbered 1 through 11) main genotypes of HCV, although others have classified the genotypes as 6 main genotypes. Each of these genotypes is further subdivided into subtypes (1a-1c; 2a-2c; 3a-3b; 4a-4e; 5a; 6a; 7a-7b; 8a-8b; 9a; 10a; and 11a). In some embodiments, an effective amount of a compound of Formula (I), or a pharmaceutical acceptable salt thereof, or a pharmaceutical composition that includes an effective amount of a compound of Formula (I), or a pharmaceutical acceptable salt thereof, can be effective to treat at least one genotype of HCV. In some embodiments, a compound described herein (for example, a compound of Formula (I), or a pharmaceutical acceptable salt thereof) can be effective to treat all 11 genotypes of HCV. In some embodiments, a compound described herein (for example, a compound of Formula (I), or a pharmaceutical acceptable salt thereof) can be effective to treat 3 or more, 5 or more, 7 or more, or 9 or more genotypes of HCV. In some embodiments, a compound of Formula (I), or a pharmaceutical acceptable salt thereof can be more effective against a larger number of HCV genotypes than the standard of care. In some embodiments, a compound of Formula (I), or a pharmaceutical acceptable salt thereof, can be more effective against a particular HCV genotype than the standard of care (such as genotype 1, 2, 3, 4, 5 and/or 6).

Various indicators for determining the effectiveness of a method for treating a HCV infection are known to those skilled in the art. Examples of suitable indicators include, but are not limited to, a reduction in viral load, a reduction in viral replication, a reduction in time to seroconversion (virus undetectable in patient serum), an increase in the rate of sustained viral response to therapy, a reduction of morbidity or mortality in clinical outcomes, a reduction in the rate of liver function decrease; stasis in liver function; improvement in liver function; reduction in one or more markers of liver dysfunction, including alanine transaminase, aspartate transaminase, total bilirubin, conjugated bilirubin, gamma glutamyl transpeptidase and/or other indicator of disease response. Similarly, successful therapy with an effective amount of a compound or a pharmaceutical composition described herein (for example, a compound of Formula (I), or a pharmaceutical acceptable salt thereof) can reduce the incidence of liver cancer in HCV infected subjects.

In some embodiments, an effective amount of a compound of Formula (I), or a pharmaceutically acceptable salt thereof, is an amount that is effective to reduce HCV viral titers to undetectable levels, for example, to about 100 to about 500, to about 50 to about 100, to about 10 to about 50, or to about 15 to about 25 international units/mL serum. In some embodiments, an effective amount of a compound of Formula (I), or a pharmaceutically acceptable salt thereof, is an amount that is effective to reduce HCV viral load compared to the HCV viral load before administration of the compound of Formula (I), or a pharmaceutically acceptable salt thereof. For example, wherein the HCV viral load is measured before administration of the compound of Formula (I), or a pharmaceutically acceptable salt thereof, and again after completion of the treatment regime with the compound of Formula (I), or a pharmaceutically acceptable salt thereof (for example, 1 month after completion). In some embodiments, an effective amount of a compound of Formula (I), or a pharmaceutically acceptable salt thereof, can be an amount that is effective to reduce HCV viral load to lower than about 25 international units/mL serum. In some embodiments, an effective amount of a compound of Formula (I), or a pharmaceutically acceptable salt thereof, is an amount that is effective to achieve a reduction in HCV viral titer in the serum of the subject in the range of about 1.5-log to about a 2.5-log reduction, about a 3-log to about a 4-log reduction, or a greater than about 5-log reduction compared to the viral load before administration of the compound of Formula (I), or a pharmaceutically acceptable salt thereof. For example, the HCV viral load can be measured before administration of the compound of Formula (I), or a pharmaceutically acceptable salt thereof, and again after completion of the treatment regime with the compound of Formula (I), or a pharmaceutically acceptable salt thereof (for example, 1 month after completion).

In some embodiments, a compound of Formula (I), or a pharmaceutically acceptable salt thereof, can result in at least a 1, 2, 3, 4, 5, 10, 15, 20, 25, 50, 75, 100-fold or more reduction in the replication of the hepatitis C virus relative to pre-treatment levels in a subject, as determined after completion of the treatment regime (for example 1 month after completion). In some embodiments, a compound of Formula (I), or a pharmaceutically acceptable salt thereof, can result in a reduction of the replication of the hepatitis C virus relative to pre-treatment levels in the range of about 2 to about 5 fold, about 10 to about 20 fold, about 15 to about 40 fold, or about 50 to about 100 fold. In some embodiments, a compound of Formula (I), or a pharmaceutically acceptable salt thereof, can result in a reduction of the hepatitis C virus replication in the range of 1 to 1.5 log, 1.5 log to 2 log, 2 log to 2.5 log, 2.5 to 3 log, 3 log to 3.5 log or 3.5 to 4 log more reduction of the hepatitis C virus replication compared to the reduction of the hepatitis C virus reduction achieved by pegylated interferon in combination with ribavirin, administered according to the standard of care, or may achieve the same reduction as that standard of care therapy in a shorter period of time, for example, in one month, two months, or three months, as compared to the reduction achieved after six months of standard of care therapy with ribavirin and pegylated interferon.

In some embodiments, an effective amount of a compound of Formula (I), or a pharmaceutically acceptable salt thereof, is an amount that is effective to achieve a sustained viral response, for example, non-detectable or substantially non-detectable HCV RNA (e.g., less than about 500, less than about 200, less than about 100, less than about 25, or less than about 15 international units per milliliter serum) is found in the subject's serum for a period of at least about one month, at least about two months, at least about three months, at least about four months, at least about five months, or at least about six months following cessation of therapy.

In some embodiments, a therapeutically effective amount of a compound of Formula (I), or a pharmaceutically acceptable salt thereof, can reduce a level of a marker of liver fibrosis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80%, or more, compared to the level of the marker in an untreated subject, or to a placebo-treated subject. Methods of measuring serum markers are known to those skilled in the art and include immunological-based methods, e.g., enzyme-linked immunosorbent assays (ELISA), radioimmunoassays, and the like, using antibody specific for a given serum marker. A non-limiting list of examples of markers includes measuring the levels of serum alanine aminotransferase (ALT), aspartate aminotransferase (AST), alkaline phosphatase (ALP), gamma-glutamyl transpeptidase (GGT) and total bilirubin (TBIL) using known methods. In general, an ALT level of less than about 45 IU/L (international units/liter), an AST in the range of 10-34 IU/L, ALP in the range of 44-147 IU/L, GGT in the range of 0-51 IU/L, TBIL in the range of 0.3-1.9 mg/dL is considered normal. In some embodiments, an effective amount of a compound of Formula (I), or a pharmaceutically acceptable salt thereof, can be an amount effective to reduce ALT, AST, ALP, GGT and/or TBIL levels to with what is considered a normal level.

Subjects who are clinically diagnosed with HCV infection include "naïve" subjects (e.g., subjects not previously treated for HCV, particularly those who have not previously received IFN-alpha-based and/or ribavirin-based therapy) and individuals who have failed prior treatment for HCV ("treatment failure" subjects). Treatment failure subjects include "non-responders" (i.e., subjects in whom the HCV titer was not significantly or sufficiently reduced by a previous treatment for HCV (≤0.5 log IU/mL), for example, a previous IFN-alpha monotherapy, a previous IFN-alpha and ribavirin combination therapy, or a previous pegylated IFN-alpha and ribavirin combination therapy); and "relapsers" (i.e., subjects who were previously treated for HCV, for example, who received a previous IFN-alpha monotherapy, a previous IFN-alpha and ribavirin combination therapy, or a previous pegylated IFN-alpha and ribavirin combination therapy, whose HCV titer decreased, and subsequently increased).

In some embodiments, a compound of Formula (I), or a pharmaceutically acceptable salt thereof, can be administered to a treatment failure subject suffering from HCV. In some embodiments, a compound of Formula (I), or a pharmaceutically acceptable salt thereof, can be administered to a non-responder subject suffering from HCV. In some embodiments, a compound of Formula (I), or a pharmaceutically acceptable salt thereof, can be administered to a relapsed subject suffering from HCV.

After a period of time, infectious agents can develop resistance to one or more therapeutic agents. The term "resistance" as used herein refers to a viral strain displaying a delayed, lessened and/or null response to a therapeutic agent(s). For example, after treatment with an antiviral agent, the viral load of a subject infected with a resistant virus may be reduced to a lesser degree compared to the amount in viral load reduction exhibited by a subject infected with a non-resistant strain. In some embodiments, a compound of Formula (I), or a pharmaceutically acceptable salt thereof, can be administered to a subject infected with an HCV strain that is resistant to one or more different anti-HCV agents (for example, an agent used in a conventional standard of care). In some embodiments, development of resistant HCV strains is delayed when a subject is treated with a compound of Formula (I), or a pharmaceutically acceptable salt thereof, compared to the development of HCV strains resistant to other HCV drugs (such as a drug used in a conventional standard of care).

In some embodiments, an effective amount of a compound of Formula (I), or a pharmaceutically acceptable salt thereof, can be administered to a subject for whom other anti-HCV medications are contraindicated. For example, administration of pegylated interferon alpha in combination with ribavirin is contraindicated in subjects with hemoglobinopathies (e.g., thalassemia major, sickle-cell anemia) and other subjects at risk from the hematologic side effects of current therapy. In some embodiments, a compound of Formula (I), or a pharmaceutically acceptable salt thereof, can be provided to a subject that is hypersensitive to interferon and/or ribavirin.

Some subjects being treated for HCV experience a viral load rebound. The term "viral load rebound" as used herein refers to a sustained ≥0.5 log IU/mL increase of viral load above nadir before the end of treatment, where nadir is a ≥0.5 log IU/mL decrease from baseline. In some embodiments, a compound of Formula (I), or a pharmaceutically acceptable salt thereof, can be administered to a subject experiencing viral load rebound, or can prevent such viral load rebound when used to treat the subject.

The standard of care for treating HCV has been associated with several side effects (adverse events). In some embodiments, a compound of Formula (I), or a pharmaceutically acceptable salt thereof, can decrease the number and/or severity of side effects that can be observed in HCV patients being treated with ribavirin and pegylated interferon according to the standard of care. Examples of side effects include, but are not limited to fever, malaise, tachycardia, chills, headache, arthralgias, myalgias, fatigue, apathy, loss of appetite, nausea, vomiting, cognitive changes, asthenia, drowsiness, lack of initiative, irritability, confusion, depression, severe depression, suicidal ideation, anemia, low white blood cell counts, and thinning of hair. In some embodiments, a compound of Formula (I), or a pharmaceutically acceptable salt thereof, can be provided to a subject that discontinued a HCV therapy because of one or more adverse effects or side effects associated with one or more other HCV agents (for example, an agent used in a conventional standard of care).

Table 1 provides some embodiments of the percentage improvement obtained using a compound of Formula (I), or a pharmaceutically acceptable salt thereof, as compared to the standard of care. Examples include the following: in some embodiments, a compound of Formula (I), or a pharmaceutically acceptable salt thereof, results in a percentage of non-responders that is 10% less than the percentage of non-responders receiving the standard of care; in some embodiments, a compound of Formula (I), or a pharmaceutically acceptable salt thereof, results in a number of side effects that is in the range of about 10% to about 30% less than compared to the number of side effects experienced by a subject receiving the standard of care; and in some embodiments, a compound of Formula (I), or a pharmaceutically acceptable salt thereof, results in a severity of a side effect (such as one of those described herein) that is 25% less than compared to the severity of the same side effect experienced by a subject receiving the standard of care. Methods of quantifying the severity of a side effect are known to those skilled in the art.

TABLE 1

| Percentage of non-responders | Percentage of relapsers | Percentage of resistance | Percentage of viral load rebound | Number of side effects | Severity of side effects |
| --- | --- | --- | --- | --- | --- |
| 10% less | 10% less | 10% less | 10% less | 10% less | 10% less |
| 25% less | 25% less | 25% less | 25% less | 25% less | 25% less |

TABLE 1-continued

| Percentage of non-responders | Percentage of relapsers | Percentage of resistance | Percentage of viral load rebound | Number of side effects | Severity of side effects |
|---|---|---|---|---|---|
| 40% less | 40% less | 40% less | 40% less | 40% less | 40% less |
| 50% less | 50% less | 50% less | 50% less | 50% less | 50% less |
| 60% less | 60% less | 60% less | 60% less | 60% less | 60% less |
| 70% less | 70% less | 70% less | 70% less | 70% less | 70% less |
| 80% less | 80% less | 80% less | 80% less | 80% less | 80% less |
| 90% less | 90% less | 90% less | 90% less | 90% less | 90% less |
| about 10% to about 30% less | about 10% to about 30% less | about 10% to about 30% less | about 10% to about 30% less | about 10% to about 30% less | about 10% to about 30% less |
| about 20% to about 50% less | about 20% to about 50% less | about 20% to about 50% less | about 20% to about 50% less | about 20% to about 50% less | about 20% to about 50% less |
| about 30% to about 70% less | about 30% to about 70% less | about 30% to about 70% less | about 30% to about 70% less | about 30% to about 70% less | about 30% to about 70% less |
| about 20% to about 80% less | about 20% to about 80% less | about 20% to about 80% less | about 20% to about 80% less | about 20% to about 80% less | about 20% to about 80% less |

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound can be the amount needed to prevent, alleviate or ameliorate symptoms of disease or prolong the survival of the subject being treated. This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some embodiments, the compounds will be administered for a period of continuous therapy, for example for a week or more, or for months or years. In some embodiments, a compound of Formula (I), or a pharmaceutically acceptable salt thereof, can be administered less frequently compared to the frequency of administration of an agent within the standard of care. In some embodiments, a compound of Formula (I), or a pharmaceutically acceptable salt thereof, can be administered one time per day. For example, a compound of Formula (I), or a pharmaceutically acceptable salt thereof, can be administered one time per day to a subject suffering from a HCV infection. In some embodiments, the total time of the treatment regime with a compound of Formula (I), or a pharmaceutically acceptable salt thereof, can less compared to the total time of the treatment regime with the standard of care.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Combination Therapies

In some embodiments, the compounds disclosed herein, such as a compound of Formula (I), or a pharmaceutically acceptable salt thereof, or a pharmaceutical composition that includes a compound described herein, or a pharmaceutically acceptable salt thereof, can be used in combination with one or more additional agent(s). Examples of additional agents that can be used in combination with a compound of Formula (I), or a pharmaceutically acceptable salt thereof, or a pharmaceutical composition that includes a compound of Formula (I), or a pharmaceutically acceptable salt thereof, include, but are not limited to, agents currently used in a conventional standard of care for treating HCV, HCV protease inhibitors, HCV polymerase inhibitors, NS5A inhibitors, other antiviral compounds, compounds of Formula (AA), (including pharmaceutically acceptable salts and pharmaceutical compositions that can include a compound of Formula (AA), or a pharmaceutically acceptable salt thereof), compounds of Formula (BB) (including pharmaceutically acceptable salts and pharmaceutical compositions that can include a compound of Formula (BB), or a pharmaceutically acceptable salt thereof), compounds of Formula (CC) (including pharmaceutically acceptable salts and pharmaceutical compositions that can include a compound of Formula (CC), or a pharmaceutically acceptable salt thereof), and/or combinations thereof. In some embodiments, a compound of Formula (I), or a pharmaceutically acceptable salt thereof, or a pharmaceutical composition that includes a compound of Formula (I), or a pharmaceutically acceptable salt thereof, can be used with one, two, three or more additional agents described herein. A non-limiting list of examples of combinations of a compound of Formula (I), or a pharmaceutically acceptable salt thereof, or a pharmaceutical composition that includes a compound of Formula (I), or a pharmaceutically acceptable salt thereof, is provided in Tables A, B, C, D and E.

In some embodiments, a compound of Formula (I), or a pharmaceutically acceptable salt thereof, or a pharmaceutical composition that includes a compound of Formula (I), or a pharmaceutically acceptable salt thereof, can be used in combination with an agent(s) currently used in a conventional standard of care therapy. For example, for the treatment of HCV, a compound disclosed herein can be used in combination with Pegylated interferon-alpha-2a (brand name PEGASYS®) and ribavirin, or Pegylated interferon-alpha-2b (brand name PEG-INTRON®) and ribavirin.

In some embodiments, a compound of Formula (I), or a pharmaceutically acceptable salt thereof, or a pharmaceutical composition that includes a compound of Formula (I), or a pharmaceutically acceptable salt thereof, can be substituted for an agent currently used in a conventional standard of care therapy. For example, for the treatment of HCV, a compound of Formula (I), or a pharmaceutically acceptable salt thereof, or a pharmaceutical composition that includes a compound of Formula (I), or a pharmaceutically acceptable salt thereof, can be used in place of ribavirin.

In some embodiments, a compound of Formula (I), or a pharmaceutically acceptable salt thereof, or a pharmaceutical composition that includes a compound of Formula (I), or a pharmaceutically acceptable salt thereof, can be used in combination with an interferon, such as a pegylated interferon. Examples of suitable interferons include, but are not limited to, Pegylated interferon-alpha-2a (brand name PEGASYS®), Pegylated interferon-alpha-2b (brand name PEG-INTRON®), interferon alfacon-1 (brand name INFERGEN®), pegylated interferon lambda and/or a combination thereof.

In some embodiments, a compound of Formula (I), or a pharmaceutically acceptable salt thereof, or a pharmaceutical composition that includes a compound of Formula (I), or a pharmaceutically acceptable salt thereof, can be used in combination with a HCV protease inhibitor. A non-limiting list of example HCV protease inhibitors include the following: VX-950 (TELAPREVIR®), MK-5172, ABT-450, BILN-2061, BI-201335, BMS-650032, SCH 503034 (BOCEPREVIR®), GS-9256, GS-9451, IDX-320, ACH-1625, ACH-2684, TMC-435, ITMN-191 (DANOPREVIR®) and/or a combination thereof. Additional HCV protease inhibitors suitable for use in combination with a compound of Formula (I), or a pharmaceutically acceptable salt thereof, or a pharmaceutical composition that includes a compound of Formula (I), or a pharmaceutically acceptable salt thereof, include VP-19744, PSI-879, VCH-759/VX-759, HCV-371, IDX-375, GL-60667, JTK-109, PSI-6130, R1479, R-1626, R-7182, MK-0608, INX-8014, INX-8018, A-848837, A-837093, BILB-1941, VCH-916, VCH-716, GSK-71185, GSK-625433, XTL-2125 and those disclosed in PCT Publication No. WO 2012/142085, which is hereby incorporated by reference for the limited purpose of its disclosure of HCV protease inhibitors, HCV polymerase inhibitors and NS5A inhibitors. A non-limiting list of example HCV protease inhibitors includes the compounds numbered 1001-1016 in FIG. 1.

In some embodiments, a compound of Formula (I), or a pharmaceutically acceptable salt thereof, or a pharmaceutical composition that includes a compound of Formula (I), or a pharmaceutically acceptable salt thereof, can be used in combination with a HCV polymerase inhibitor. In some embodiments, the HCV polymerase inhibitor can be a nucleoside inhibitor. In other embodiments, the HCV polymerase inhibitor can be a non-nucleoside inhibitor. Examples of suitable nucleoside inhibitors include, but are not limited to, RG7128, PSI-7851, PSI-7977, INX-189, PSI-352938, PSI-661, 4'-azidouridine (including known prodrugs of 4'-azidouridine), GS-6620, IDX-184, and TMC649128 and/or combinations thereof. A non-limiting list of example nucleoside inhibitors includes compounds numbered 2001-2012 in FIG. 2. Examples of suitable non-nucleoside inhibitors include, but are not limited to, ABT-333, ANA-598, VX-222, HCV-796, BI-207127, GS-9190, PF-00868554 (FILIBUVIR®), VX-497 and/or combinations thereof. A non-limiting list of example non-nucleoside inhibitors includes the compounds numbered 3001-3014 in FIG. 3. Further HCV polymerase inhibitors suitable for use in combination with a compound of Formula (I), or a pharmaceutically acceptable salt thereof, or a pharmaceutical composition that includes a compound of Formula (I), or a pharmaceutically acceptable salt thereof, include VX-500, VX-813, VBY-376, TMC-435350, EZ-058, EZ-063, GS-9132, ACH-1095, IDX-136, IDX-316, ITMN-8356, ITMN-8347, ITMN-8096, ITMN-7587, VX-985, and those disclosed in PCT Publication No. WO 2012/142085.

In some embodiments, a compound of Formula (I), or a pharmaceutically acceptable salt thereof, or a pharmaceutical composition that includes a compound of Formula (I), or a pharmaceutically acceptable salt thereof, can be used in combination with a NS5A inhibitor. Examples of NS5A inhibitors include BMS-790052, PPI-461, ACH-2928, GS-5885, BMS-824393 and/or combinations thereof. A non-limiting list of example NS5A inhibitors includes the compounds numbered 4001-4012 in FIG. 4. Additional NS5A inhibitors suitable for use in combination with a compound of Formula (I), or a pharmaceutically acceptable salt thereof, or a pharmaceutical composition that includes a compound of Formula (I), or a pharmaceutically acceptable salt thereof, include A-832, PPI-1301 and those disclosed in PCT Publication No. WO 2012/142085.

In some embodiments, a compound of Formula (I), or a pharmaceutically acceptable salt thereof, or a pharmaceutical composition that includes a compound of Formula (I), or a pharmaceutically acceptable salt thereof, can be used in combination with other antiviral compounds. Examples of other antiviral compounds include, but are not limited to, Debio-025, MIR-122, cyclosporin A and/or combinations thereof. A non-limiting list of example other antiviral compounds includes the compounds numbered 5001-5012 in FIG. 5.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (AA), or a pharmaceutically acceptable salt thereof, or a pharmaceutical composition that includes a compound of Formula (AA), or a pharmaceutically acceptable salt thereof (see, U.S. Publication No. 2013/0164261, filed Jun. 27, 2013, the contents of which are incorporated by reference in its entirety):

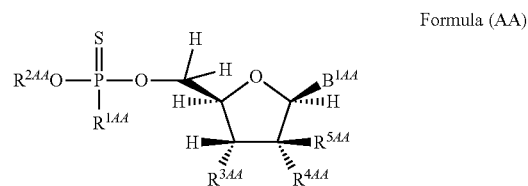

Formula (AA)

wherein: $B^{AA1}$ can be an optionally substituted heterocyclic base or an optionally substituted heterocyclic base with a protected amino group; $R^{AA1}$ can be selected from O⁻, OH, an optionally substituted N-linked amino acid and an optionally substituted N-linked amino acid ester derivative; $R^{AA2}$ can be absent or selected from hydrogen, an optionally substituted aryl, an optionally substituted heteroaryl, an optionally substituted heterocyclyl and

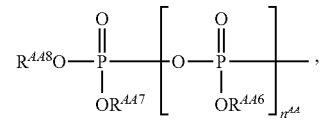

wherein $R^{AA6}$, $R^{AA7}$ and $R^{AA8}$ can be independently absent or hydrogen, and $n^{AA}$ can be 0 or 1; provided that when $R^{AA1}$ is O⁻ or OH, then $R^{AA2}$ is absent, hydrogen or

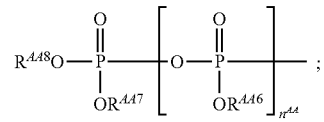

$R^{AA3}$ can be selected from hydrogen, halogen, —$OR^{AA9}$ and —OC(=O)$R^{AA10}$; $R^{AA4}$ can be selected from halogen, —$OR^{AA11}$ and —OC(=O)$R^{AA12}$; or $R^{AA3}$ and $R^{AA4}$ can be both an oxygen atom which are linked together by a carbonyl group; $R^{AA5}$ can be selected from an optionally substituted $C_{2-6}$ alkyl, an optionally substituted $C_{2-6}$ alkenyl, an optionally substituted $C_{2-6}$ alkynyl and an optionally substituted $C_{3-6}$ cycloalkyl; or $R^{AA4}$ and $R^{AA5}$ together can form —($C_{1-6}$ alkyl)-O— or —O—($C_{1-6}$ alkyl)-; $R^{AA9}$ and $R^{AA11}$ can be independently hydrogen or an optionally substituted $C_{1-6}$ alkyl; and $R^{AA10}$ and $R^{AA12}$ can be independently an optionally substituted $C_{1-6}$ alkyl or an optionally substituted $C_{3-6}$ cycloalkyl. A non-limiting list of examples of compounds of Formula (AA) includes the compounds numbered 7000-7027 in FIG. 7.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (BB), or a pharmaceutically acceptable salt thereof, or a pharmaceutical composition that includes a compound of Formula (BB), or a pharmaceutically acceptable salt thereof (see, U.S. Publication No. 2012/0165286, published Jun. 28, 2012, the contents of which are incorporated by reference in their entireties):

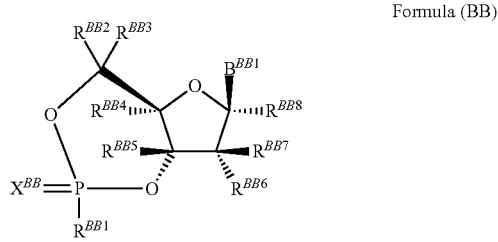

Formula (BB)

wherein $B^{BB1}$ can be an optionally substituted heterocyclic base or an optionally substituted heterocyclic base with a protected amino group; $X^{BB}$ can be O (oxygen) or S (sulfur); $R^{BB1}$ can be selected from $—Z^{BB}—R^{BB9}$, an optionally substituted N-linked amino acid and an optionally substituted N-linked amino acid ester derivative; $Z^{BB}$ can be selected from O (oxygen), S (sulfur) and $N(R^{BB10})$; $R^{BB2}$ and $R^{BB3}$ can be independently selected from hydrogen, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and an optionally substituted aryl($C_{1-6}$ alkyl); or $R^{BB2}$ and $R^{BB3}$ can be taken together to form a group selected from an optionally substituted $C_{3-6}$ cycloalkyl, an optionally substituted $C_{3-6}$ cycloalkenyl, an optionally substituted $C_{3-6}$ aryl and an optionally substituted $C_{3-6}$ heteroaryl; $R^{BB4}$ can be selected from hydrogen, halogen, azido, cyano, an optionally substituted $C_{1-6}$ alkyl, an optionally substituted $C_{2-6}$ alkenyl, an optionally substituted $C_{2-6}$ alkynyl and an optionally substituted allenyl; $R^{BB5}$ can be hydrogen or an optionally substituted $C_{1-6}$ alkyl; $R^{BB6}$ can be selected from hydrogen, halogen, azido, amino, cyano, an optionally substituted $C_{1-6}$ alkyl, $—OR^{BB11}$ and $—OC(=O)R^{BB12}$; $R^{BB7}$ can be selected from hydrogen, halogen, azido, cyano, an optionally substituted $C_{1-6}$ alkyl, $—OR^{BB13}$ and $—OC(=O)R^{BB14}$; $R^{BB8}$ can be selected from hydrogen, halogen, azido, cyano, an optionally substituted $C_{1-6}$ alkyl, $—OR^{BB15}$ and $—OC(=O)R^{BB16}$; $R^{BB9}$ can be selected from an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$alkyl), an optionally substituted heteroaryl($C_{1-6}$alkyl) and an optionally substituted heterocyclyl ($C_{1-6}$alkyl); $R^{BB10}$ can be selected from hydrogen, an optionally substituted alkyl, an optionally substituted alkenyl, an optionally substituted alkynyl, an optionally substituted cycloalkyl, an optionally substituted cycloalkenyl, an optionally substituted aryl, an optionally substituted heteroaryl, an optionally substituted heterocyclyl, an optionally substituted aryl($C_{1-6}$alkyl), an optionally substituted heteroaryl($C_{1-6}$alkyl) and an optionally substituted heterocyclyl ($C_{1-6}$alkyl); $R^{BB11}$, $R^{BB13}$ and $R^{BB15}$ can be independently hydrogen or an optionally substituted $C_{1-6}$ alkyl; and $R^{BB12}$, $R^{BB14}$ and $R^{BB16}$ can be independently an optionally substituted $C_{1-6}$ alkyl or an optionally substituted $C_{3-6}$ cycloalkyl. In some embodiments, at least one of $R^{BB2}$ and $R^{BB3}$ is not hydrogen. A non-limiting list of example compounds of Formula (BB) includes the compound numbered 8000-8016 in FIG. 8.

In some embodiments, a compound of Formula (I), or a pharmaceutically acceptable salt thereof, or a pharmaceutical composition that includes a compound of Formula (I), or a pharmaceutically acceptable salt thereof, can be used in combination with a compound of Formula (CC), or a pharmaceutically acceptable salt thereof, or a pharmaceutical composition that includes a compound of Formula (CC), or a pharmaceutically acceptable salt thereof (see, U.S. Publication No. 2012/0071434, published Mar. 22, 2012, the contents of which are incorporated by reference in its entirety):

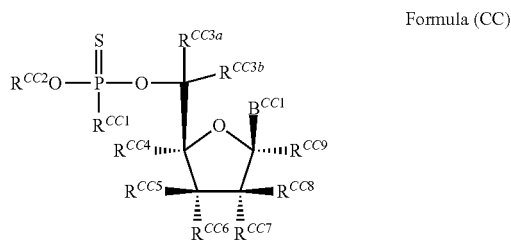

Formula (CC)

wherein $B^{CC1}$ can be an optionally substituted heterocyclic base or an optionally substituted heterocyclic base with a protected amino group; $R^{CC1}$ can be selected from $O^-$, OH, an optionally substituted N-linked amino acid and an optionally substituted N-linked amino acid ester derivative; $R^{CC2}$ can be selected from an optionally substituted aryl, an optionally substituted heteroaryl, an optionally substituted heterocyclyl and

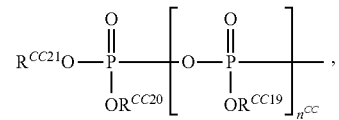

wherein $R^{CC19}$, $R^{CC20}$ and $R^{CC21}$ can be independently absent or hydrogen, and $n^{CC}$ can be 0 or 1; provided that when $R^{CC1}$ is $O^-$ or OH, then $R^{CC2}$ is

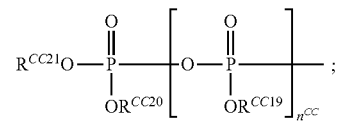

$R^{CC3a}$ and $R^{CC3b}$ can be independently selected from hydrogen, deuterium, an optionally substituted $C_{1-6}$ alkyl, an optionally substituted $C_{2-6}$ alkenyl, an optionally substituted $C_{2-6}$ alkynyl, an optionally substituted $C_{1-6}$ haloalkyl and aryl($C_{1-6}$ alkyl); or $R^{CC3a}$ and $R^{CC3b}$ can be taken together to form an optionally substituted $C_{3-6}$ cycloalkyl; $R^{CC4}$ can be selected from hydrogen, azido, an optionally substituted $C_{1-6}$ alkyl, an optionally substituted $C_{2-6}$ alkenyl and an optionally substituted $C_{2-6}$ alkynyl; $R^{CC5}$ can be selected from hydrogen, halogen, azido, cyano, an optionally substituted $C_{1-6}$ alkyl, $—OR^{CC10}$ and $—OC(=O)R^{CC11}$; $R^{CC6}$ can be selected from hydrogen, halogen, cyano, an optionally substituted $C_{1-6}$ alkyl, $—OR^{CC12}$ and $—OC(=O)$ $R^{CC13}$; $R^{CC7}$ can be selected from hydrogen, halogen, azido, cyano, an optionally substituted $C_{1-6}$ alkyl, —$OR^{CC14}$ and —$OC(=O)R^{CC15}$; or $R^{CC6}$ and $R^{CC7}$ can be selected and linked together by a carbonyl group; $R^{CC8}$ can be selected from hydrogen, halogen, azido, cyano, an optionally substituted $C_{1-6}$ alkyl, —$OR^{CC16}$ and —$OC(=O)R^{CC17}$; $R^{CC9}$ can be selected from hydrogen, azido, cyano, an optionally substituted $C_{1-6}$ alkyl and —$OR^{CC18}$; $R^{CC10}$, $R^{CC12}$, $R^{CC14}$, $R^{CC16}$ and $R^{CC18}$ can be independently selected from hydrogen and an optionally substituted $C_{1-6}$ alkyl; and $R^{CC11}$, $R^{CC13}$, $R^{CC15}$ and $R^{CC17}$ can be independently selected from an optionally substituted $C_{1-6}$ alkyl and an optionally substituted $C_{3-6}$ cycloalkyl. In some embodiments, when $R^{CC3a}$, $R^{CC3b}$, $R^{CC4}$, $R^{CC5}$, $R^{CC7}$, $R^{CC8}$ and $R^{CC9}$ are all hydrogen, then $R^{CC6}$ is not azido. In some embodiments, $R^{CC2}$ cannot be

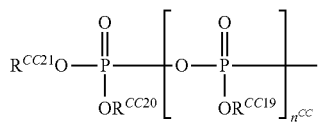

when $R^{CC3a}$ is hydrogen, $R^{CC3b}$ is hydrogen, $R^{CC4}$ is H, $R^{CC5}$ is OH or H, $R^{CC6}$ is hydrogen, OH, or —$OC(=O)$ $CH_3$, $R^{CC7}$ is hydrogen, OH, $OCH_3$ or —$OC(=O)CH_3$, $R^{CC8}$ is hydrogen, OH or $OCH_3$, $R^{CC9}$ is H and $B^{CC1}$ is an optionally substituted adenine, an optionally substituted guanine, an optionally substituted uracil or an optionally substituted hypoxanthine. In some embodiments, $R^{CC2}$ cannot be

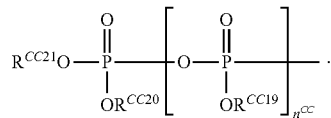

A non-limiting list of examples of compounds of Formula (CC) includes the compounds numbered 6000-6078 in FIG. 6.

Some embodiments described herein relate to a method of ameliorating or treating a HCV infection that can include contacting a cell infected with the HCV infection with a therapeutically effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB) and a compound of Formula (CC), or a pharmaceutically acceptable salt of any of the aforementioned compounds.

Some embodiments described herein relate to a method of ameliorating or treating a HCV infection that can include administering to a subject suffering from the HCV infection a therapeutically effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB) and a compound of Formula (CC), or a pharmaceutically acceptable salt of any of the aforementioned compounds.

Some embodiments described herein relate to a method of inhibiting the replication of a hepatitis C virus that can include contacting a cell infected with the hepatitis C virus with an effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB) and a compound of Formula (CC), or a pharmaceutically acceptable salt of any of the aforementioned compounds.

Some embodiments described herein relate to a method of inhibiting the replication of a hepatitis C virus that can include administering to a subject infected with the hepatitis C virus an effective amount of a compound of Formula (I), or a pharmaceutically acceptable salt thereof, in combination with one or more agents selected from an interferon, ribavirin, a HCV protease inhibitor, a HCV polymerase inhibitor, a NS5A inhibitor, an antiviral compound, a compound of Formula (AA), a compound of Formula (BB) and a compound of Formula (CC), or a pharmaceutically acceptable salt of any of the aforementioned compounds.

In some embodiments, a compound of Formula (I), or a pharmaceutically acceptable salt thereof, can be administered with one or more additional agent(s) together in a single pharmaceutical composition. In some embodiments, a compound of Formula (I), or a pharmaceutically acceptable salt the thereof, can be administered with one or more additional agent(s) as two or more separate pharmaceutical compositions. For example, a compound of Formula (I), or a pharmaceutically acceptable salt thereof, can be administered in one pharmaceutical composition, and at least one of the additional agents can be administered in a second pharmaceutical composition. If there are at least two additional agents, one or more of the additional agents can be in a first pharmaceutical composition that includes a compound of Formula (I), or a pharmaceutically acceptable salt thereof, and at least one of the other additional agent(s) can be in a second pharmaceutical composition.

The dosing amount(s) and dosing schedule(s) when using a compound of Formula (I), or a pharmaceutically acceptable salt thereof, or a pharmaceutical composition that includes a compound of Formula (I), or a pharmaceutically acceptable salt thereof, and one or more additional agents are within the knowledge of those skilled in the art. For example, when performing a conventional standard of care therapy using art-recognized dosing amounts and dosing schedules, a compound of Formula (I), or a pharmaceutically acceptable salt thereof, or a pharmaceutical composition that includes a compound of Formula (I), or a pharmaceutically acceptable salt thereof, can be administered in addition to that therapy, or in place of one of the agents of a combination therapy, using effective amounts and dosing protocols as described herein.

The order of administration of a compound of Formula (I), or a pharmaceutically acceptable salt thereof, with one or more additional agent(s) can vary. In some embodiments, a compound of Formula (I), or a pharmaceutically acceptable salt thereof, can be administered prior to all additional agents. In other embodiments, a compound of Formula (I), or a pharmaceutically acceptable salt thereof, can be administered prior to at least one additional agent. In still other embodiments, a compound of Formula (I), or a pharmaceutically acceptable salt thereof, can be administered concomitantly with one or more additional agent(s). In yet still other embodiments, a compound of Formula (I), or a pharmaceutically acceptable salt thereof, can be administered subsequent to the administration of at least one additional agent. In some embodiments, a compound of Formula (I), or a pharmaceutically acceptable salt thereof, can be administered subsequent to the administration of all additional agents.

In some embodiments, the combination of a compound of Formula (I), or a pharmaceutically acceptable salt thereof, in combination with one or more additional agent(s) in FIGS. 1-8 (including pharmaceutically acceptable salts and prodrugs thereof) can result in an additive effect. In some embodiments, the combination of a compound of Formula (I), or a pharmaceutically acceptable salt thereof, in combination with one or more additional agent(s) in FIGS. 1-8 (including pharmaceutically acceptable salts and prodrugs thereof) can result in a synergistic effect. In some embodiments, the combination of a compound of Formula (I), or a pharmaceutically acceptable salt thereof, in combination with one or more additional agent(s) in FIGS. 1-8 (including pharmaceutically acceptable salts and prodrugs thereof) can result in a strongly synergistic effect. In some embodiments, the combination of a compound of Formula (I), or a pharmaceutically acceptable salt thereof, in combination with one or more additional agent(s) in FIGS. 1-8 (including pharmaceutically acceptable salts and prodrugs thereof) is not antagonistic.

As used herein, the term "antagonistic" means that the activity of the combination of compounds is less compared to the sum of the activities of the compounds in combination when the activity of each compound is determined individually (i.e. as a single compound). As used herein, the term "synergistic effect" means that the activity of the combination of compounds is greater than the sum of the individual activities of the compounds in the combination when the activity of each compound is determined individually. As used herein, the term "additive effect" means that the activity of the combination of compounds is about equal to the sum of the individual activities of the compound in the combination when the activity of each compound is determined individually.

A potential advantage of utilizing a compound of Formula (I), or a pharmaceutically acceptable salt thereof, in combination with one or more additional agent(s) in FIGS. 1-8 (including pharmaceutically acceptable salts thereof) may be a reduction in the required amount(s) of one or more compounds of FIGS. 1-8 (including pharmaceutically acceptable salts thereof) that is effective in treating a disease condition disclosed herein (for example, HCV), as compared to the amount required to achieve same therapeutic result when one or more compounds of FIGS. 1-8 (including pharmaceutically acceptable salts thereof) are administered without a compound of Formula (I), or a pharmaceutically acceptable salt thereof. For example, the amount of a compound in FIGS. 1-8 (including a pharmaceutically acceptable salt thereof), can be less compared to the amount of the compound in FIGS. 1-8 (including a pharmaceutically acceptable salt thereof), needed to achieve the same viral load reduction when administered as a monotherapy. Another potential advantage of utilizing a compound of Formula (I), or a pharmaceutically acceptable salt thereof, in combination with one or more additional agent(s) in FIGS. 1-8 (including pharmaceutically acceptable salts thereof) is that the use of two or more compounds having different mechanism of actions can create a higher barrier to the development of resistant viral strains compared to the barrier when a compound is administered as monotherapy.

Additional advantages of utilizing a compound of Formula (I), or a pharmaceutically acceptable salt thereof, in combination with one or more additional agent(s) in FIGS. 1-8 (including pharmaceutically acceptable salts thereof) may include little to no cross resistance between a compound of Formula (I), or a pharmaceutically acceptable salt thereof, and one or more additional agent(s) in FIGS. 1-8 (including pharmaceutically acceptable salts thereof) thereof; different routes for elimination of a compound of Formula (I), or a pharmaceutically acceptable salt thereof, and one or more additional agent(s) in FIGS. 1-8 (including pharmaceutically acceptable salts thereof); little to no overlapping toxicities between a compound of Formula (I), or a pharmaceutically acceptable salt thereof, and one or more additional agent(s) in FIGS. 1-8 (including pharmaceutically acceptable salts thereof); little to no significant effects on cytochrome P450; little to no pharmacokinetic interactions between a compound of Formula (I), or a pharmaceutically acceptable salt thereof, and one or more additional agent(s) in FIGS. 1-8 (including pharmaceutically acceptable salts thereof); greater percentage of subjects achieving a sustained viral response compared to when a compound is administered as monotherapy and/or a decrease in treatment time to achieve a sustained viral response compared to when a compound is administered as monotherapy.

A non-limiting list of example combination of compounds of Formula (I), or a pharmaceutically acceptable salt thereof, or a pharmaceutical composition that includes a compound described herein, with one or more additional agent(s) are provided in Tables A, B, C, D and E. Each numbered X and Y compound in Tables A, B, C, D and E has a corresponding name and/or structure provided in FIGS. 1-8. The numbered compounds in Tables A, B, C, D and E includes pharmaceutically acceptable salts of the compounds and pharmaceutical compositions containing the compounds or a pharmaceutically acceptable salt thereof. For example, 1001 includes the compound corresponding to 1001, pharmaceutically acceptable salts thereof, and pharmaceutical compositions that include compound 1001 and/or a pharmaceutically acceptable salt thereof. The combinations exemplified in Tables A, B, C, D and E are designated by the formula X:Y, which represents a combination of a compound X with a compound Y. For example, the combination designated as 1001:9002 in Table A represents a combination of compound 1001 with compound 9002, including pharmaceutically acceptable salts of compound 1001 and/or 9002, and pharmaceutical compositions including compound 1001 and 9002 (including pharmaceutical compositions that include pharmaceutically acceptable salts of compound 1001 and/or compound 9002). Thus, the combination designated as 1001: 9002 in Table A represents the combination of Telaprevir (compound 1001, as shown in FIG. 1) and

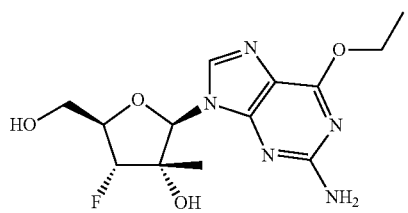 [SMILES: CCOc1nc(N)nc2c1ncn2[C@@H]1O[C@H](CO)[C@@H](F)[C@@]1(C)O]

Figure 9:
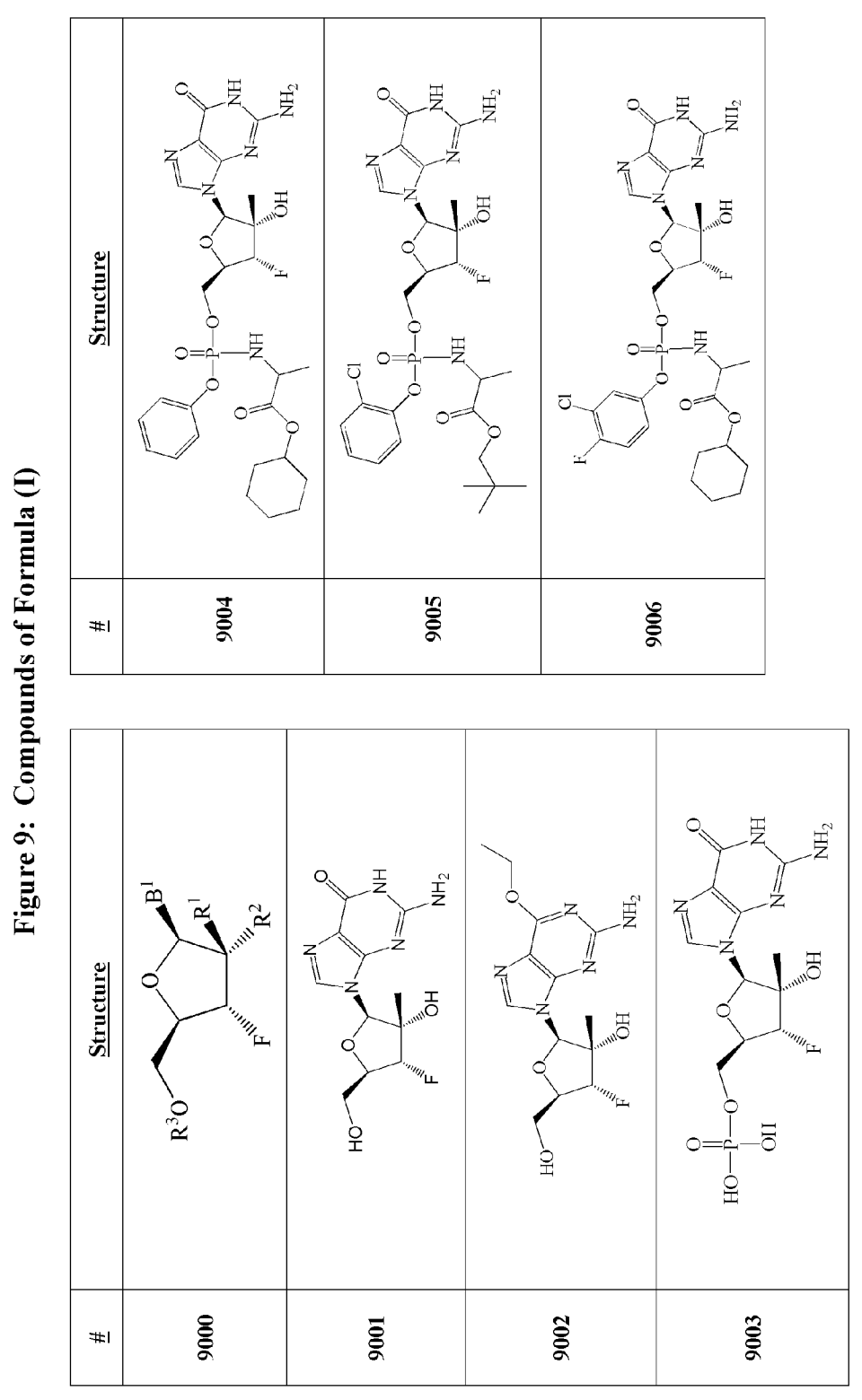

(compound 9002, as shown in FIG. 9), including pharmaceutically acceptable salts of compound 1001 and/or 9002, and pharmaceutical compositions including compound 1001 and 9002 (including pharmaceutical compositions that include pharmaceutically acceptable salts of compound 1001 and/or compound 9002). Each of the combinations provided in Tables A, B, C, D and E can be used with one, two, three or more additional agents described herein. In some embodiments described herein, the combination of agents can be used to treat, ameliorate and/or inhibit a virus and/or a viral infection, wherein the virus can be HCV and the viral infection can be an HCV viral infection.

TABLE A

Example combinations of a compound X with a compound Y.

| X:Y | X:Y | X:Y | X:Y | X:Y | X:Y |
|---|---|---|---|---|---|
| 1001:9000 | 1001:9001 | 1001:9002 | 1001:9003 | 1001:9004 | 1001:9005 |
| 1002:9000 | 1002:9001 | 1002:9002 | 1002:9003 | 1002:9004 | 1002:9005 |
| 1003:9000 | 1003:9001 | 1003:9002 | 1003:9003 | 1003:9004 | 1003:9005 |
| 1004:9000 | 1004:9001 | 1004:9002 | 1004:9003 | 1004:9004 | 1004:9005 |
| 1005:9000 | 1005:9001 | 1005:9002 | 1005:9003 | 1005:9004 | 1005:9005 |
| 1006:9000 | 1006:9001 | 1006:9002 | 1006:9003 | 1006:9004 | 1006:9005 |
| 1007:9000 | 1007:9001 | 1007:9002 | 1007:9003 | 1007:9004 | 1007:9005 |
| 1008:9000 | 1008:9001 | 1008:9002 | 1008:9003 | 1008:9004 | 1008:9005 |
| 1009:9000 | 1009:9001 | 1009:9002 | 1009:9003 | 1009:9004 | 1009:9005 |
| 1010:9000 | 1010:9001 | 1010:9002 | 1010:9003 | 1010:9004 | 1010:9005 |
| 1011:9000 | 1011:9001 | 1011:9002 | 1011:9003 | 1011:9004 | 1011:9005 |
| 1012:9000 | 1012:9001 | 1012:9002 | 1012:9003 | 1012:9004 | 1012:9005 |
| 1013:9000 | 1013:9001 | 1013:9002 | 1013:9003 | 1013:9004 | 1013:9005 |
| 1014:9000 | 1014:9001 | 1014:9002 | 1014:9003 | 1014:9004 | 1014:9005 |
| 1015:9000 | 1015:9001 | 1015:9002 | 1015:9003 | 1015:9004 | 1015:9005 |
| 1016:9000 | 1016:9001 | 1016:9002 | 1016:9003 | 1016:9004 | 1016:9005 |
| 2001:9000 | 2001:9001 | 2001:9002 | 2001:9003 | 2001:9004 | 2001:9005 |
| 2002:9000 | 2002:9001 | 2002:9002 | 2002:9003 | 2002:9004 | 2002:9005 |
| 2003:9000 | 2003:9001 | 2003:9002 | 2003:9003 | 2003:9004 | 2003:9005 |
| 2004:9000 | 2004:9001 | 2004:9002 | 2004:9003 | 2004:9004 | 2004:9005 |
| 2005:9000 | 2005:9001 | 2005:9002 | 2005:9003 | 2005:9004 | 2005:9005 |
| 2006:9000 | 2006:9001 | 2006:9002 | 2006:9003 | 2006:9004 | 2006:9005 |
| 2007:9000 | 2007:9001 | 2007:9002 | 2007:9003 | 2007:9004 | 2007:9005 |
| 2008:9000 | 2008:9001 | 2008:9002 | 2008:9003 | 2008:9004 | 2008:9005 |
| 2009:9000 | 2009:9001 | 2009:9002 | 2009:9003 | 2009:9004 | 2009:9005 |
| 2010:9000 | 2010:9001 | 2010:9002 | 2010:9003 | 2010:9004 | 2010:9005 |
| 2011:9000 | 2011:9001 | 2011:9002 | 2011:9003 | 2011:9004 | 2011:9005 |
| 2012:9000 | 2012:9001 | 2012:9002 | 2012:9003 | 2012:9004 | 2012:9005 |
| 1001:9006 | 1001:9007 | 1001:9008 | 1001:9009 | 1001:9010 | 1001:9011 |
| 1002:9006 | 1002:9007 | 1002:9008 | 1002:9009 | 1002:9010 | 1002:9011 |
| 1003:9006 | 1003:9007 | 1003:9008 | 1003:9009 | 1003:9010 | 1003:9011 |
| 1004:9006 | 1004:9007 | 1004:9008 | 1004:9009 | 1004:9010 | 1004:9011 |
| 1005:9006 | 1005:9007 | 1005:9008 | 1005:9009 | 1005:9010 | 1005:9011 |
| 1006:9006 | 1006:9007 | 1006:9008 | 1006:9009 | 1006:9010 | 1006:9011 |
| 1007:9006 | 1007:9007 | 1007:9008 | 1007:9009 | 1007:9010 | 1007:9011 |
| 1008:9006 | 1008:9007 | 1008:9008 | 1008:9009 | 1008:9010 | 1008:9011 |
| 1009:9006 | 1009:9007 | 1009:9008 | 1009:9009 | 1009:9010 | 1009:9011 |
| 1010:9006 | 1010:9007 | 1010:9008 | 1010:9009 | 1010:9010 | 1010:9011 |
| 1011:9006 | 1011:9007 | 1011:9008 | 1011:9009 | 1011:9010 | 1011:9011 |
| 1012:9006 | 1012:9007 | 1012:9008 | 1012:9009 | 1012:9010 | 1012:9011 |
| 1013:9006 | 1013:9007 | 1013:9008 | 1013:9009 | 1013:9010 | 1013:9011 |
| 1014:9006 | 1014:9007 | 1014:9008 | 1014:9009 | 1014:9010 | 1014:9011 |
| 1015:9006 | 1015:9007 | 1015:9008 | 1015:9009 | 1015:9010 | 1015:9011 |
| 1016:9006 | 1016:9007 | 1016:9008 | 1016:9009 | 1016:9010 | 1016:9011 |
| 2001:9006 | 2001:9007 | 2001:9008 | 2001:9009 | 2001:9010 | 2001:9011 |
| 2002:9006 | 2002:9007 | 2002:9008 | 2002:9009 | 2002:9010 | 2002:9011 |
| 2003:9006 | 2003:9007 | 2003:9008 | 2003:9009 | 2003:9010 | 2003:9011 |
| 2004:9006 | 2004:9007 | 2004:9008 | 2004:9009 | 2004:9010 | 2004:9011 |
| 2005:9006 | 2005:9007 | 2005:9008 | 2005:9009 | 2005:9010 | 2005:9011 |
| 2006:9006 | 2006:9007 | 2006:9008 | 2006:9009 | 2006:9010 | 2006:9011 |
| 2007:9006 | 2007:9007 | 2007:9008 | 2007:9009 | 2007:9010 | 2007:9011 |
| 2008:9006 | 2008:9007 | 2008:9008 | 2008:9009 | 2008:9010 | 2008:9011 |
| 2009:9006 | 2009:9007 | 2009:9008 | 2009:9009 | 2009:9010 | 2009:9011 |
| 2010:9006 | 2010:9007 | 2010:9008 | 2010:9009 | 2010:9010 | 2010:9011 |
| 2011:9006 | 2011:9007 | 2011:9008 | 2011:9009 | 2011:9010 | 2011:9011 |
| 2012:9006 | 2012:9007 | 2012:9008 | 2012:9009 | 2012:9010 | 2012:9011 |
| 1001:9012 | 1001:9013 | 1001:9014 | 1001:9015 | — | — |
| 1002:9012 | 1002:9013 | 1002:9014 | 1002:9015 | | |
| 1003:9012 | 1003:9013 | 1003:9014 | 1003:9015 | | |
| 1004:9012 | 1004:9013 | 1004:9014 | 1004:9015 | | |
| 1005:9012 | 1005:9013 | 1005:9014 | 1005:9015 | | |
| 1006:9012 | 1006:9013 | 1006:9014 | 1006:9015 | | |
| 1007:9012 | 1007:9013 | 1007:9014 | 1007:9015 | | |
| 1008:9012 | 1008:9013 | 1008:9014 | 1008:9015 | | |
| 1009:9012 | 1009:9013 | 1009:9014 | 1009:9015 | | |
| 1010:9012 | 1010:9013 | 1010:9014 | 1010:9015 | | |
| 1011:9012 | 1011:9013 | 1011:9014 | 1011:9015 | | |
| 1012:9012 | 1012:9013 | 1012:9014 | 1012:9015 | | |
| 1013:9012 | 1013:9013 | 1013:9014 | 1013:9015 | | |
| 1014:9012 | 1014:9013 | 1014:9014 | 1014:9015 | | |
| 1015:9012 | 1015:9013 | 1015:9014 | 1015:9015 | | |
| 1016:9012 | 1016:9013 | 1016:9014 | 1016:9015 | | |
| 2001:9012 | 2001:9013 | 2001:9014 | 2001:9015 | | |
| 2002:9012 | 2002:9013 | 2002:9014 | 2002:9015 | | |
| 2003:9012 | 2003:9013 | 2003:9014 | 2003:9015 | | |
| 2004:9012 | 2004:9013 | 2004:9014 | 2004:9015 | | |
| 2005:9012 | 2005:9013 | 2005:9014 | 2005:9015 | | |
| 2006:9012 | 2006:9013 | 2006:9014 | 2006:9015 | | |
| 2007:9012 | 2007:9013 | 2007:9014 | 2007:9015 | | |
| 2008:9012 | 2008:9013 | 2008:9014 | 2008:9015 | | |
| 2009:9012 | 2009:9013 | 2009:9014 | 2009:9015 | | |
| 2010:9012 | 2010:9013 | 2010:9014 | 2010:9015 | | |
| 2011:9012 | 2011:9013 | 2011:9014 | 2011:9015 | | |
| 2012:9012 | 2012:9013 | 2012:9014 | 2012:9015 | | |

TABLE B

Example combinations of a compound X with a compound Y.

| X:Y | X:Y | X:Y | X:Y | X:Y | X:Y |
|---|---|---|---|---|---|
| 3001:9000 | 3001:9001 | 3001:9002 | 3001:9003 | 3001:9004 | 3001:9005 |
| 3002:9000 | 3002:9001 | 3002:9002 | 3002:9003 | 3002:9004 | 3002:9005 |
| 3003:9000 | 3003:9001 | 3003:9002 | 3003:9003 | 3003:9004 | 3003:9005 |
| 3004:9000 | 3004:9001 | 3004:9002 | 3004:9003 | 3004:9004 | 3004:9005 |
| 3005:9000 | 3005:9001 | 3005:9002 | 3005:9003 | 3005:9004 | 3005:9005 |
| 3006:9000 | 3006:9001 | 3006:9002 | 3006:9003 | 3006:9004 | 3006:9005 |
| 3007:9000 | 3007:9001 | 3007:9002 | 3007:9003 | 3007:9004 | 3007:9005 |
| 3008:9000 | 3008:9001 | 3008:9002 | 3008:9003 | 3008:9004 | 3008:9005 |
| 3009:9000 | 3009:9001 | 3009:9002 | 3009:9003 | 3009:9004 | 3009:9005 |
| 3010:9000 | 3010:9001 | 3010:9002 | 3010:9003 | 3010:9004 | 3010:9005 |
| 3011:9000 | 3011:9001 | 3011:9002 | 3011:9003 | 3011:9004 | 3011:9005 |
| 3012:9000 | 3012:9001 | 3012:9002 | 3012:9003 | 3012:9004 | 3012:9005 |
| 3013:9000 | 3013:9001 | 3013:9002 | 3013:9003 | 3013:9004 | 3013:9005 |
| 3014:9000 | 3014:9001 | 3014:9002 | 3014:9003 | 3014:9004 | 3014:9005 |
| 4001:9000 | 4001:9001 | 4001:9002 | 4001:9003 | 4001:9004 | 4001:9005 |
| 4002:9000 | 4002:9001 | 4002:9002 | 4002:9003 | 4002:9004 | 4002:9005 |
| 4003:9000 | 4003:9001 | 4003:9002 | 4003:9003 | 4003:9004 | 4003:9005 |
| 4004:9000 | 4004:9001 | 4004:9002 | 4004:9003 | 4004:9004 | 4004:9005 |
| 4005:9000 | 4005:9001 | 4005:9002 | 4005:9003 | 4005:9004 | 4005:9005 |
| 4006:9000 | 4006:9001 | 4006:9002 | 4006:9003 | 4006:9004 | 4006:9005 |
| 4007:9000 | 4007:9001 | 4007:9002 | 4007:9003 | 4007:9004 | 4007:9005 |
| 4008:9000 | 4008:9001 | 4008:9002 | 4008:9003 | 4008:9004 | 4008:9005 |
| 4009:9000 | 4009:9001 | 4009:9002 | 4009:9003 | 4009:9004 | 4009:9005 |
| 4010:9000 | 4010:9001 | 4010:9002 | 4010:9003 | 4010:9004 | 4010:9005 |
| 4011:9000 | 4011:9001 | 4011:9002 | 4011:9003 | 4011:9004 | 4011:9005 |
| 4012:9000 | 4012:9001 | 4012:9002 | 4012:9003 | 4012:9004 | 4012:9005 |
| 5001:9000 | 5001:9001 | 5001:9002 | 5001:9003 | 5001:9004 | 5001:9005 |
| 5002:9000 | 5002:9001 | 5002:9002 | 5002:9003 | 5002:9004 | 5002:9005 |
| 5003:9000 | 5003:9001 | 5003:9002 | 5003:9003 | 5003:9004 | 5003:9005 |
| 5004:9000 | 5004:9001 | 5004:9002 | 5004:9003 | 5004:9004 | 5004:9005 |
| 5005:9000 | 5005:9001 | 5005:9002 | 5005:9003 | 5005:9004 | 5005:9005 |
| 5006:9000 | 5006:9001 | 5006:9002 | 5006:9003 | 5006:9004 | 5006:9005 |
| 5007:9000 | 5007:9001 | 5007:9002 | 5007:9003 | 5007:9004 | 5007:9005 |
| 5008:9000 | 5008:9001 | 5008:9002 | 5008:9003 | 5008:9004 | 5008:9005 |
| 5009:9000 | 5009:9001 | 5009:9002 | 5009:9003 | 5009:9004 | 5009:9005 |
| 5010:9000 | 5010:9001 | 5010:9002 | 5010:9003 | 5010:9004 | 5010:9005 |
| 5011:9000 | 5011:9001 | 5011:9002 | 5011:9003 | 5011:9004 | 5011:9005 |
| 5012:9000 | 5012:9001 | 5012:9002 | 5012:9003 | 5012:9004 | 5012:9005 |
| 3001:9006 | 3001:9007 | 3001:9008 | 3001:9009 | 3001:9010 | 3001:9011 |
| 3002:9006 | 3002:9007 | 3002:9008 | 3002:9009 | 3002:9010 | 3002:9011 |
| 3003:9006 | 3003:9007 | 3003:9008 | 3003:9009 | 3003:9010 | 3003:9011 |
| 3004:9006 | 3004:9007 | 3004:9008 | 3004:9009 | 3004:9010 | 3004:9011 |
| 3005:9006 | 3005:9007 | 3005:9008 | 3005:9009 | 3005:9010 | 3005:9011 |
| 3006:9006 | 3006:9007 | 3006:9008 | 3006:9009 | 3006:9010 | 3006:9011 |
| 3007:9006 | 3007:9007 | 3007:9008 | 3007:9009 | 3007:9010 | 3007:9011 |
| 3008:9006 | 3008:9007 | 3008:9008 | 3008:9009 | 3008:9010 | 3008:9011 |
| 3009:9006 | 3009:9007 | 3009:9008 | 3009:9009 | 3009:9010 | 3009:9011 |
| 3010:9006 | 3010:9007 | 3010:9008 | 3010:9009 | 3010:9010 | 3010:9011 |

TABLE B-continued

Example combinations of a compound X with a compound Y.

| X:Y | X:Y | X:Y | X:Y | X:Y | X:Y |
|---|---|---|---|---|---|
| 3011:9006 | 3011:9007 | 3011:9008 | 3011:9009 | 3011:9010 | 3011:9011 |
| 3012:9006 | 3012:9007 | 3012:9008 | 3012:9009 | 3012:9010 | 3012:9011 |
| 3013:9006 | 3013:9007 | 3013:9008 | 3013:9009 | 3013:9010 | 3013:9011 |
| 3014:9006 | 3014:9007 | 3014:9008 | 3014:9009 | 3014:9010 | 3014:9011 |
| 4001:9006 | 4001:9007 | 4001:9008 | 4001:9009 | 4001:9010 | 4001:9011 |
| 4002:9006 | 4002:9007 | 4002:9008 | 4002:9009 | 4002:9010 | 4002:9011 |
| 4003:9006 | 4003:9007 | 4003:9008 | 4003:9009 | 4003:9010 | 4003:9011 |
| 4004:9006 | 4004:9007 | 4004:9008 | 4004:9009 | 4004:9010 | 4004:9011 |
| 4005:9006 | 4005:9007 | 4005:9008 | 4005:9009 | 4005:9010 | 4005:9011 |
| 4006:9006 | 4006:9007 | 4006:9008 | 4006:9009 | 4006:9010 | 4006:9011 |
| 4007:9006 | 4007:9007 | 4007:9008 | 4007:9009 | 4007:9010 | 4007:9011 |
| 4008:9006 | 4008:9007 | 4008:9008 | 4008:9009 | 4008:9010 | 4008:9011 |
| 4009:9006 | 4009:9007 | 4009:9008 | 4009:9009 | 4009:9010 | 4009:9011 |
| 4010:9006 | 4010:9007 | 4010:9008 | 4010:9009 | 4010:9010 | 4010:9011 |
| 4011:9006 | 4011:9007 | 4011:9008 | 4011:9009 | 4011:9010 | 4011:9011 |
| 4012:9006 | 4012:9007 | 4012:9008 | 4012:9009 | 4012:9010 | 4012:9011 |
| 5001:9006 | 5001:9007 | 5001:9008 | 5001:9009 | 5001:9010 | 5001:9011 |
| 5002:9006 | 5002:9007 | 5002:9008 | 5002:9009 | 5002:9010 | 5002:9011 |
| 5003:9006 | 5003:9007 | 5003:9008 | 5003:9009 | 5003:9010 | 5003:9011 |
| 5004:9006 | 5004:9007 | 5004:9008 | 5004:9009 | 5004:9010 | 5004:9011 |
| 5005:9006 | 5005:9007 | 5005:9008 | 5005:9009 | 5005:9010 | 5005:9011 |
| 5006:9006 | 5006:9007 | 5006:9008 | 5006:9009 | 5006:9010 | 5006:9011 |
| 5007:9006 | 5007:9007 | 5007:9008 | 5007:9009 | 5007:9010 | 5007:9011 |
| 5008:9006 | 5008:9007 | 5008:9008 | 5008:9009 | 5008:9010 | 5008:9011 |
| 5009:9006 | 5009:9007 | 5009:9008 | 5009:9009 | 5009:9010 | 5009:9011 |
| 5010:9006 | 5010:9007 | 5010:9008 | 5010:9009 | 5010:9010 | 5010:9011 |
| 5011:9006 | 5011:9007 | 5011:9008 | 5011:9009 | 5011:9010 | 5011:9011 |
| 5012:9006 | 5012:9007 | 5012:9008 | 5012:9009 | 5012:9010 | 5012:9011 |
| 3001:9012 | 3001:9013 | 3001:9014 | 3001:9015 | — | — |
| 3002:9012 | 3002:9013 | 3002:9014 | 3002:9015 | | |
| 3003:9012 | 3003:9013 | 3003:9014 | 3003:9015 | | |
| 3004:9012 | 3004:9013 | 3004:9014 | 3004:9015 | | |
| 3005:9012 | 3005:9013 | 3005:9014 | 3005:9015 | | |
| 3006:9012 | 3006:9013 | 3006:9014 | 3006:9015 | | |
| 3007:9012 | 3007:9013 | 3007:9014 | 3007:9015 | | |
| 3008:9012 | 3008:9013 | 3008:9014 | 3008:9015 | | |
| 3009:9012 | 3009:9013 | 3009:9014 | 3009:9015 | | |
| 3010:9012 | 3010:9013 | 3010:9014 | 3010:9015 | | |
| 3011:9012 | 3011:9013 | 3011:9014 | 3011:9015 | | |
| 3012:9012 | 3012:9013 | 3012:9014 | 3012:9015 | | |
| 3013:9012 | 3013:9013 | 3013:9014 | 3013:9015 | | |
| 3014:9012 | 3014:9013 | 3014:9014 | 3014:9015 | | |
| 4001:9012 | 4001:9013 | 4001:9014 | 4001:9015 | | |
| 4002:9012 | 4002:9013 | 4002:9014 | 4002:9015 | | |
| 4003:9012 | 4003:9013 | 4003:9014 | 4003:9015 | | |
| 4004:9012 | 4004:9013 | 4004:9014 | 4004:9015 | | |
| 4005:9012 | 4005:9013 | 4005:9014 | 4005:9015 | | |
| 4006:9012 | 4006:9013 | 4006:9014 | 4006:9015 | | |
| 4007:9012 | 4007:9013 | 4007:9014 | 4007:9015 | | |
| 4008:9012 | 4008:9013 | 4008:9014 | 4008:9015 | | |
| 4009:9012 | 4009:9013 | 4009:9014 | 4009:9015 | | |
| 4010:9012 | 4010:9013 | 4010:9014 | 4010:9015 | | |
| 4011:9012 | 4011:9013 | 4011:9014 | 4011:9015 | | |
| 4012:9012 | 4012:9013 | 4012:9014 | 4012:9015 | | |
| 5001:9012 | 5001:9013 | 5001:9014 | 5001:9015 | | |
| 5002:9012 | 5002:9013 | 5002:9014 | 5002:9015 | | |
| 5003:9012 | 5003:9013 | 5003:9014 | 5003:9015 | | |
| 5004:9012 | 5004:9013 | 5004:9014 | 5004:9015 | | |
| 5005:9012 | 5005:9013 | 5005:9014 | 5005:9015 | | |
| 5006:9012 | 5006:9013 | 5006:9014 | 5006:9015 | | |
| 5007:9012 | 5007:9013 | 5007:9014 | 5007:9015 | | |
| 5008:9012 | 5008:9013 | 5008:9014 | 5008:9015 | | |
| 5009:9012 | 5009:9013 | 5009:9014 | 5009:9015 | | |
| 5010:9012 | 5010:9013 | 5010:9014 | 5010:9015 | | |
| 5011:9012 | 5011:9013 | 5011:9014 | 5011:9015 | | |
| 5012:9012 | 5012:9013 | 5012:9014 | 5012:9015 | | |

TABLE C

Example combinations of a compound X with a compound Y.

| X:Y | X:Y | X:Y | X:Y | X:Y | X:Y |
|---|---|---|---|---|---|
| 6000:9000 | 6043:9000 | 6000:9001 | 6043:9001 | 6000:9002 | 6043:9002 |
| 6001:9000 | 6044:9000 | 6001:9001 | 6044:9001 | 6001:9002 | 6044:9002 |
| 6002:9000 | 6045:9000 | 6002:9001 | 6045:9001 | 6002:9002 | 6045:9002 |
| 6003:9000 | 6046:9000 | 6003:9001 | 6046:9001 | 6003:9002 | 6046:9002 |
| 6004:9000 | 6047:9000 | 6004:9001 | 6047:9001 | 6004:9002 | 6047:9002 |
| 6005:9000 | 6048:9000 | 6005:9001 | 6048:9001 | 6005:9002 | 6048:9002 |
| 6006:9000 | 6049:9000 | 6006:9001 | 6049:9001 | 6006:9002 | 6049:9002 |
| 6007:9000 | 6050:9000 | 6007:9001 | 6050:9001 | 6007:9002 | 6050:9002 |
| 6008:9000 | 6051:9000 | 6008:9001 | 6051:9001 | 6008:9002 | 6051:9002 |
| 6009:9000 | 6052:9000 | 6009:9001 | 6052:9001 | 6009:9002 | 6052:9002 |
| 6010:9000 | 6053:9000 | 6010:9001 | 6053:9001 | 6010:9002 | 6053:9002 |
| 6011:9000 | 6054:9000 | 6011:9001 | 6054:9001 | 6011:9002 | 6054:9002 |
| 6012:9000 | 6055:9000 | 6012:9001 | 6055:9001 | 6012:9002 | 6055:9002 |
| 6013:9000 | 6056:9000 | 6013:9001 | 6056:9001 | 6013:9002 | 6056:9002 |
| 6014:9000 | 6057:9000 | 6014:9001 | 6057:9001 | 6014:9002 | 6057:9002 |
| 6015:9000 | 6058:9000 | 6015:9001 | 6058:9001 | 6015:9002 | 6058:9002 |
| 6016:9000 | 6059:9000 | 6016:9001 | 6059:9001 | 6016:9002 | 6059:9002 |
| 6017:9000 | 6060:9000 | 6017:9001 | 6060:9001 | 6017:9002 | 6060:9002 |
| 6018:9000 | 6061:9000 | 6018:9001 | 6061:9001 | 6018:9002 | 6061:9002 |
| 6019:9000 | 6062:9000 | 6019:9001 | 6062:9001 | 6019:9002 | 6062:9002 |
| 6020:9000 | 6063:9000 | 6020:9001 | 6063:9001 | 6020:9002 | 6063:9002 |
| 6021:9000 | 6064:9000 | 6021:9001 | 6064:9001 | 6021:9002 | 6064:9002 |
| 6022:9000 | 6065:9000 | 6022:9001 | 6065:9001 | 6022:9002 | 6065:9002 |
| 6023:9000 | 6066:9000 | 6023:9001 | 6066:9001 | 6023:9002 | 6066:9002 |
| 6024:9000 | 6067:9000 | 6024:9001 | 6067:9001 | 6024:9002 | 6067:9002 |
| 6025:9000 | 6068:9000 | 6025:9001 | 6068:9001 | 6025:9002 | 6068:9002 |
| 6026:9000 | 6069:9000 | 6026:9001 | 6069:9001 | 6026:9002 | 6069:9002 |
| 6027:9000 | 6070:9000 | 6027:9001 | 6070:9001 | 6027:9002 | 6070:9002 |
| 6028:9000 | 6071:9000 | 6028:9001 | 6071:9001 | 6028:9002 | 6071:9002 |
| 6029:9000 | 6072:9000 | 6029:9001 | 6072:9001 | 6029:9002 | 6072:9002 |
| 6030:9000 | 6073:9000 | 6030:9001 | 6073:9001 | 6030:9002 | 6073:9002 |
| 6031:9000 | 6074:9000 | 6031:9001 | 6074:9001 | 6031:9002 | 6074:9002 |
| 6032:9000 | 6075:9000 | 6032:9001 | 6075:9001 | 6032:9002 | 6075:9002 |
| 6033:9000 | 6076:9000 | 6033:9001 | 6076:9001 | 6033:9002 | 6076:9002 |
| 6034:9000 | 6077:9000 | 6034:9001 | 6077:9001 | 6034:9002 | 6077:9002 |
| 6035:9000 | 6078:9000 | 6035:9001 | 6078:9001 | 6035:9002 | 6078:9002 |
| 6036:9000 | | 6036:9001 | | 6036:9002 | |
| 6037:9000 | | 6037:9001 | | 6037:9002 | |
| 6038:9000 | | 6038:9001 | | 6038:9002 | |
| 6039:9000 | | 6039:9001 | | 6039:9002 | |
| 6040:9000 | | 6040:9001 | | 6040:9002 | |
| 6041:9000 | | 6041:9001 | | 6041:9002 | |
| 6042:9000 | | 6042:9001 | | 6042:9002 | |
| 6000:9003 | 6043:9003 | 6000:9004 | 6043:9004 | 6000:9005 | 6043:9005 |
| 6001:9003 | 6044:9003 | 6001:9004 | 6044:9004 | 6001:9005 | 6044:9005 |
| 6002:9003 | 6045:9003 | 6002:9004 | 6045:9004 | 6002:9005 | 6045:9005 |
| 6003:9003 | 6046:9003 | 6003:9004 | 6046:9004 | 6003:9005 | 6046:9005 |
| 6004:9003 | 6047:9003 | 6004:9004 | 6047:9004 | 6004:9005 | 6047:9005 |
| 6005:9003 | 6048:9003 | 6005:9004 | 6048:9004 | 6005:9005 | 6048:9005 |
| 6006:9003 | 6049:9003 | 6006:9004 | 6049:9004 | 6006:9005 | 6049:9005 |
| 6007:9003 | 6050:9003 | 6007:9004 | 6050:9004 | 6007:9005 | 6050:9005 |
| 6008:9003 | 6051:9003 | 6008:9004 | 6051:9004 | 6008:9005 | 6051:9005 |
| 6009:9003 | 6052:9003 | 6009:9004 | 6052:9004 | 6009:9005 | 6052:9005 |
| 6010:9003 | 6053:9003 | 6010:9004 | 6053:9004 | 6010:9005 | 6053:9005 |
| 6011:9003 | 6054:9003 | 6011:9004 | 6054:9004 | 6011:9005 | 6054:9005 |
| 6012:9003 | 6055:9003 | 6012:9004 | 6055:9004 | 6012:9005 | 6055:9005 |
| 6013:9003 | 6056:9003 | 6013:9004 | 6056:9004 | 6013:9005 | 6056:9005 |
| 6014:9003 | 6057:9003 | 6014:9004 | 6057:9004 | 6014:9005 | 6057:9005 |
| 6015:9003 | 6058:9003 | 6015:9004 | 6058:9004 | 6015:9005 | 6058:9005 |
| 6016:9003 | 6059:9003 | 6016:9004 | 6059:9004 | 6016:9005 | 6059:9005 |
| 6017:9003 | 6060:9003 | 6017:9004 | 6060:9004 | 6017:9005 | 6060:9005 |
| 6018:9003 | 6061:9003 | 6018:9004 | 6061:9004 | 6018:9005 | 6061:9005 |
| 6019:9003 | 6062:9003 | 6019:9004 | 6062:9004 | 6019:9005 | 6062:9005 |
| 6020:9003 | 6063:9003 | 6020:9004 | 6063:9004 | 6020:9005 | 6063:9005 |
| 6021:9003 | 6064:9003 | 6021:9004 | 6064:9004 | 6021:9005 | 6064:9005 |
| 6022:9003 | 6065:9003 | 6022:9004 | 6065:9004 | 6022:9005 | 6065:9005 |
| 6023:9003 | 6066:9003 | 6023:9004 | 6066:9004 | 6023:9005 | 6066:9005 |
| 6024:9003 | 6067:9003 | 6024:9004 | 6067:9004 | 6024:9005 | 6067:9005 |
| 6025:9003 | 6068:9003 | 6025:9004 | 6068:9004 | 6025:9005 | 6068:9005 |
| 6026:9003 | 6069:9003 | 6026:9004 | 6069:9004 | 6026:9005 | 6069:9005 |
| 6027:9003 | 6070:9003 | 6027:9004 | 6070:9004 | 6027:9005 | 6070:9005 |
| 6028:9003 | 6071:9003 | 6028:9004 | 6071:9004 | 6028:9005 | 6071:9005 |
| 6029:9003 | 6072:9003 | 6029:9004 | 6072:9004 | 6029:9005 | 6072:9005 |
| 6030:9003 | 6073:9003 | 6030:9004 | 6073:9004 | 6030:9005 | 6073:9005 |
| 6031:9003 | 6074:9003 | 6031:9004 | 6074:9004 | 6031:9005 | 6074:9005 |
| 6032:9003 | 6075:9003 | 6032:9004 | 6075:9004 | 6032:9005 | 6075:9005 |

TABLE C-continued

Example combinations of a compound X with a compound Y.

| X:Y | X:Y | X:Y | X:Y | X:Y | X:Y |
|---|---|---|---|---|---|
| 6033:9003 | 6076:9003 | 6033:9004 | 6076:9004 | 6033:9005 | 6076:9005 |
| 6034:9003 | 6077:9003 | 6034:9004 | 6077:9004 | 6034:9005 | 6077:9005 |
| 6035:9003 | 6078:9003 | 6035:9004 | 6078:9004 | 6035:9005 | 6078:9005 |
| 6036:9003 | | 6036:9004 | | 6036:9005 | |
| 6037:9003 | | 6037:9004 | | 6037:9005 | |
| 6038:9003 | | 6038:9004 | | 6038:9005 | |
| 6039:9003 | | 6039:9004 | | 6039:9005 | |
| 6040:9003 | | 6040:9004 | | 6040:9005 | |
| 6041:9003 | | 6041:9004 | | 6041:9005 | |
| 6042:9003 | | 6042:9004 | | 6042:9005 | |
| 6000:9006 | 6043:9006 | 6000:9007 | 6043:9007 | 6000:9008 | 6043:9008 |
| 6001:9006 | 6044:9006 | 6001:9007 | 6044:9007 | 6001:9008 | 6044:9008 |
| 6002:9006 | 6045:9006 | 6002:9007 | 6045:9007 | 6002:9008 | 6045:9008 |
| 6003:9006 | 6046:9006 | 6003:9007 | 6046:9007 | 6003:9008 | 6046:9008 |
| 6004:9006 | 6047:9006 | 6004:9007 | 6047:9007 | 6004:9008 | 6047:9008 |
| 6005:9006 | 6048:9006 | 6005:9007 | 6048:9007 | 6005:9008 | 6048:9008 |
| 6006:9006 | 6049:9006 | 6006:9007 | 6049:9007 | 6006:9008 | 6049:9008 |
| 6007:9006 | 6050:9006 | 6007:9007 | 6050:9007 | 6007:9008 | 6050:9008 |
| 6008:9006 | 6051:9006 | 6008:9007 | 6051:9007 | 6008:9008 | 6051:9008 |
| 6009:9006 | 6052:9006 | 6009:9007 | 6052:9007 | 6009:9008 | 6052:9008 |
| 6010:9006 | 6053:9006 | 6010:9007 | 6053:9007 | 6010:9008 | 6053:9008 |
| 6011:9006 | 6054:9006 | 6011:9007 | 6054:9007 | 6011:9008 | 6054:9008 |
| 6012:9006 | 6055:9006 | 6012:9007 | 6055:9007 | 6012:9008 | 6055:9008 |
| 6013:9006 | 6056:9006 | 6013:9007 | 6056:9007 | 6013:9008 | 6056:9008 |
| 6014:9006 | 6057:9006 | 6014:9007 | 6057:9007 | 6014:9008 | 6057:9008 |
| 6015:9006 | 6058:9006 | 6015:9007 | 6058:9007 | 6015:9008 | 6058:9008 |
| 6016:9006 | 6059:9006 | 6016:9007 | 6059:9007 | 6016:9008 | 6059:9008 |
| 6017:9006 | 6060:9006 | 6017:9007 | 6060:9007 | 6017:9008 | 6060:9008 |
| 6018:9006 | 6061:9006 | 6018:9007 | 6061:9007 | 6018:9008 | 6061:9008 |
| 6019:9006 | 6062:9006 | 6019:9007 | 6062:9007 | 6019:9008 | 6062:9008 |
| 6020:9006 | 6063:9006 | 6020:9007 | 6063:9007 | 6020:9008 | 6063:9008 |
| 6021:9006 | 6064:9006 | 6021:9007 | 6064:9007 | 6021:9008 | 6064:9008 |
| 6022:9006 | 6065:9006 | 6022:9007 | 6065:9007 | 6022:9008 | 6065:9008 |
| 6023:9006 | 6066:9006 | 6023:9007 | 6066:9007 | 6023:9008 | 6066:9008 |
| 6024:9006 | 6067:9006 | 6024:9007 | 6067:9007 | 6024:9008 | 6067:9008 |
| 6025:9006 | 6068:9006 | 6025:9007 | 6068:9007 | 6025:9008 | 6068:9008 |
| 6026:9006 | 6069:9006 | 6026:9007 | 6069:9007 | 6026:9008 | 6069:9008 |
| 6027:9006 | 6070:9006 | 6027:9007 | 6070:9007 | 6027:9008 | 6070:9008 |
| 6028:9006 | 6071:9006 | 6028:9007 | 6071:9007 | 6028:9008 | 6071:9008 |
| 6029:9006 | 6072:9006 | 6029:9007 | 6072:9007 | 6029:9008 | 6072:9008 |
| 6030:9006 | 6073:9006 | 6030:9007 | 6073:9007 | 6030:9008 | 6073:9008 |
| 6031:9006 | 6074:9006 | 6031:9007 | 6074:9007 | 6031:9008 | 6074:9008 |
| 6032:9006 | 6075:9006 | 6032:9007 | 6075:9007 | 6032:9008 | 6075:9008 |
| 6033:9006 | 6076:9006 | 6033:9007 | 6076:9007 | 6033:9008 | 6076:9008 |
| 6034:9006 | 6077:9006 | 6034:9007 | 6077:9007 | 6034:9008 | 6077:9008 |
| 6035:9006 | 6078:9006 | 6035:9007 | 6078:9007 | 6035:9008 | 6078:9008 |
| 6036:9006 | | 6036:9007 | | 6036:9008 | |
| 6037:9006 | | 6037:9007 | | 6037:9008 | |
| 6038:9006 | | 6038:9007 | | 6038:9008 | |
| 6039:9006 | | 6039:9007 | | 6039:9008 | |
| 6040:9006 | | 6040:9007 | | 6040:9008 | |
| 6041:9006 | | 6041:9007 | | 6041:9008 | |
| 6042:9006 | | 6042:9007 | | 6042:9008 | |
| 6000:9009 | 6043:9009 | 6000:9010 | 6043:9010 | 6000:9011 | 6043:9011 |
| 6001:9009 | 6044:9009 | 6001:9010 | 6044:9010 | 6001:9011 | 6044:9011 |
| 6002:9009 | 6045:9009 | 6002:9010 | 6045:9010 | 6002:9011 | 6045:9011 |
| 6003:9009 | 6046:9009 | 6003:9010 | 6046:9010 | 6003:9011 | 6046:9011 |
| 6004:9009 | 6047:9009 | 6004:9010 | 6047:9010 | 6004:9011 | 6047:9011 |
| 6005:9009 | 6048:9009 | 6005:9010 | 6048:9010 | 6005:9011 | 6048:9011 |
| 6006:9009 | 6049:9009 | 6006:9010 | 6049:9010 | 6006:9011 | 6049:9011 |
| 6007:9009 | 6050:9009 | 6007:9010 | 6050:9010 | 6007:9011 | 6050:9011 |
| 6008:9009 | 6051:9009 | 6008:9010 | 6051:9010 | 6008:9011 | 6051:9011 |
| 6009:9009 | 6052:9009 | 6009:9010 | 6052:9010 | 6009:9011 | 6052:9011 |
| 6010:9009 | 6053:9009 | 6010:9010 | 6053:9010 | 6010:9011 | 6053:9011 |
| 6011:9009 | 6054:9009 | 6011:9010 | 6054:9010 | 6011:9011 | 6054:9011 |
| 6012:9009 | 6055:9009 | 6012:9010 | 6055:9010 | 6012:9011 | 6055:9011 |
| 6013:9009 | 6056:9009 | 6013:9010 | 6056:9010 | 6013:9011 | 6056:9011 |
| 6014:9009 | 6057:9009 | 6014:9010 | 6057:9010 | 6014:9011 | 6057:9011 |
| 6015:9009 | 6058:9009 | 6015:9010 | 6058:9010 | 6015:9011 | 6058:9011 |
| 6016:9009 | 6059:9009 | 6016:9010 | 6059:9010 | 6016:9011 | 6059:9011 |
| 6017:9009 | 6060:9009 | 6017:9010 | 6060:9010 | 6017:9011 | 6060:9011 |
| 6018:9009 | 6061:9009 | 6018:9010 | 6061:9010 | 6018:9011 | 6061:9011 |
| 6019:9009 | 6062:9009 | 6019:9010 | 6062:9010 | 6019:9011 | 6062:9011 |
| 6020:9009 | 6063:9009 | 6020:9010 | 6063:9010 | 6020:9011 | 6063:9011 |
| 6021:9009 | 6064:9009 | 6021:9010 | 6064:9010 | 6021:9011 | 6064:9011 |
| 6022:9009 | 6065:9009 | 6022:9010 | 6065:9010 | 6022:9011 | 6065:9011 |
| 6023:9009 | 6066:9009 | 6023:9010 | 6066:9010 | 6023:9011 | 6066:9011 |
| 6024:9009 | 6067:9009 | 6024:9010 | 6067:9010 | 6024:9011 | 6067:9011 |
| 6025:9009 | 6068:9009 | 6025:9010 | 6068:9010 | 6025:9011 | 6068:9011 |
| 6026:9009 | 6069:9009 | 6026:9010 | 6069:9010 | 6026:9011 | 6069:9011 |
| 6027:9009 | 6070:9009 | 6027:9010 | 6070:9010 | 6027:9011 | 6070:9011 |
| 6028:9009 | 6071:9009 | 6028:9010 | 6071:9010 | 6028:9011 | 6071:9011 |
| 6029:9009 | 6072:9009 | 6029:9010 | 6072:9010 | 6029:9011 | 6072:9011 |
| 6030:9009 | 6073:9009 | 6030:9010 | 6073:9010 | 6030:9011 | 6073:9011 |
| 6031:9009 | 6074:9009 | 6031:9010 | 6074:9010 | 6031:9011 | 6074:9011 |
| 6032:9009 | 6075:9009 | 6032:9010 | 6075:9010 | 6032:9011 | 6075:9011 |
| 6033:9009 | 6076:9009 | 6033:9010 | 6076:9010 | 6033:9011 | 6076:9011 |
| 6034:9009 | 6077:9009 | 6034:9010 | 6077:9010 | 6034:9011 | 6077:9011 |
| 6035:9009 | 6078:9009 | 6035:9010 | 6078:9010 | 6035:9011 | 6078:9011 |
| 6036:9009 | | 6036:9010 | | 6036:9011 | |
| 6037:9009 | | 6037:9010 | | 6037:9011 | |
| 6038:9009 | | 6038:9010 | | 6038:9011 | |
| 6039:9009 | | 6039:9010 | | 6039:9011 | |
| 6040:9009 | | 6040:9010 | | 6040:9011 | |
| 6041:9009 | | 6041:9010 | | 6041:9011 | |
| 6042:9009 | | 6042:9010 | | 6042:9011 | |
| 6000:9012 | 6043:9012 | 6000:9013 | 6043:9013 | 6000:9014 | 6043:9014 |
| 6001:9012 | 6044:9012 | 6001:9013 | 6044:9013 | 6001:9014 | 6044:9014 |
| 6002:9012 | 6045:9012 | 6002:9013 | 6045:9013 | 6002:9014 | 6045:9014 |
| 6003:9012 | 6046:9012 | 6003:9013 | 6046:9013 | 6003:9014 | 6046:9014 |
| 6004:9012 | 6047:9012 | 6004:9013 | 6047:9013 | 6004:9014 | 6047:9014 |
| 6005:9012 | 6048:9012 | 6005:9013 | 6048:9013 | 6005:9014 | 6048:9014 |
| 6006:9012 | 6049:9012 | 6006:9013 | 6049:9013 | 6006:9014 | 6049:9014 |
| 6007:9012 | 6050:9012 | 6007:9013 | 6050:9013 | 6007:9014 | 6050:9014 |
| 6008:9012 | 6051:9012 | 6008:9013 | 6051:9013 | 6008:9014 | 6051:9014 |
| 6009:9012 | 6052:9012 | 6009:9013 | 6052:9013 | 6009:9014 | 6052:9014 |
| 6010:9012 | 6053:9012 | 6010:9013 | 6053:9013 | 6010:9014 | 6053:9014 |
| 6011:9012 | 6054:9012 | 6011:9013 | 6054:9013 | 6011:9014 | 6054:9014 |
| 6012:9012 | 6055:9012 | 6012:9013 | 6055:9013 | 6012:9014 | 6055:9014 |
| 6013:9012 | 6056:9012 | 6013:9013 | 6056:9013 | 6013:9014 | 6056:9014 |
| 6014:9012 | 6057:9012 | 6014:9013 | 6057:9013 | 6014:9014 | 6057:9014 |
| 6015:9012 | 6058:9012 | 6015:9013 | 6058:9013 | 6015:9014 | 6058:9014 |
| 6016:9012 | 6059:9012 | 6016:9013 | 6059:9013 | 6016:9014 | 6059:9014 |
| 6017:9012 | 6060:9012 | 6017:9013 | 6060:9013 | 6017:9014 | 6060:9014 |
| 6018:9012 | 6061:9012 | 6018:9013 | 6061:9013 | 6018:9014 | 6061:9014 |
| 6019:9012 | 6062:9012 | 6019:9013 | 6062:9013 | 6019:9014 | 6062:9014 |
| 6020:9012 | 6063:9012 | 6020:9013 | 6063:9013 | 6020:9014 | 6063:9014 |
| 6021:9012 | 6064:9012 | 6021:9013 | 6064:9013 | 6021:9014 | 6064:9014 |
| 6022:9012 | 6065:9012 | 6022:9013 | 6065:9013 | 6022:9014 | 6065:9014 |
| 6023:9012 | 6066:9012 | 6023:9013 | 6066:9013 | 6023:9014 | 6066:9014 |
| 6024:9012 | 6067:9012 | 6024:9013 | 6067:9013 | 6024:9014 | 6067:9014 |
| 6025:9012 | 6068:9012 | 6025:9013 | 6068:9013 | 6025:9014 | 6068:9014 |
| 6026:9012 | 6069:9012 | 6026:9013 | 6069:9013 | 6026:9014 | 6069:9014 |
| 6027:9012 | 6070:9012 | 6027:9013 | 6070:9013 | 6027:9014 | 6070:9014 |
| 6028:9012 | 6071:9012 | 6028:9013 | 6071:9013 | 6028:9014 | 6071:9014 |
| 6029:9012 | 6072:9012 | 6029:9013 | 6072:9013 | 6029:9014 | 6072:9014 |
| 6030:9012 | 6073:9012 | 6030:9013 | 6073:9013 | 6030:9014 | 6073:9014 |
| 6031:9012 | 6074:9012 | 6031:9013 | 6074:9013 | 6031:9014 | 6074:9014 |
| 6032:9012 | 6075:9012 | 6032:9013 | 6075:9013 | 6032:9014 | 6075:9014 |
| 6033:9012 | 6076:9012 | 6033:9013 | 6076:9013 | 6033:9014 | 6076:9014 |
| 6034:9012 | 6077:9012 | 6034:9013 | 6077:9013 | 6034:9014 | 6077:9014 |
| 6035:9012 | 6078:9012 | 6035:9013 | 6078:9013 | 6035:9014 | 6078:9014 |
| 6036:9012 | | 6036:9013 | | 6036:9014 | |
| 6037:9012 | | 6037:9013 | | 6037:9014 | |
| 6038:9012 | | 6038:9013 | | 6038:9014 | |
| 6039:9012 | | 6039:9013 | | 6039:9014 | |
| 6040:9012 | | 6040:9013 | | 6040:9014 | |
| 6041:9012 | | 6041:9013 | | 6041:9014 | |
| 6042:9012 | | 6042:9013 | | 6042:9014 | |
| 6000:9015 | 6043:9015 | — | — | — | — |
| 6001:9015 | 6044:9015 | | | | |
| 6002:9015 | 6045:9015 | | | | |
| 6003:9015 | 6046:9015 | | | | |
| 6004:9015 | 6047:9015 | | | | |
| 6005:9015 | 6048:9015 | | | | |
| 6006:9015 | 6049:9015 | | | | |
| 6007:9015 | 6050:9015 | | | | |
| 6008:9015 | 6051:9015 | | | | |
| 6009:9015 | 6052:9015 | | | | |
| 6010:9015 | 6053:9015 | | | | |
| 6011:9015 | 6054:9015 | | | | |
| 6012:9015 | 6055:9015 | | | | |

TABLE C-continued

Example combinations of a compound X with a compound Y.

| X:Y | X:Y |
|---|---|
| 6013:9015 | 6056:9015 |
| 6014:9015 | 6057:9015 |
| 6015:9015 | 6058:9015 |
| 6016:9015 | 6059:9015 |
| 6017:9015 | 6060:9015 |
| 6018:9015 | 6061:9015 |
| 6019:9015 | 6062:9015 |
| 6020:9015 | 6063:9015 |
| 6021:9015 | 6064:9015 |
| 6022:9015 | 6065:9015 |
| 6023:9015 | 6066:9015 |
| 6024:9015 | 6067:9015 |
| 6025:9015 | 6068:9015 |
| 6026:9015 | 6069:9015 |
| 6027:9015 | 6070:9015 |
| 6028:9015 | 6071:9015 |
| 6029:9015 | 6072:9015 |
| 6030:9015 | 6073:9015 |
| 6031:9015 | 6074:9015 |
| 6032:9015 | 6075:9015 |
| 6033:9015 | 6076:9015 |
| 6034:9015 | 6077:9015 |
| 6035:9015 | 6078:9015 |
| 6036:9015 | |
| 6037:9015 | |
| 6038:9015 | |
| 6039:9015 | |
| 6040:9015 | |
| 6041:9015 | |
| 6042:9015 | |

TABLE D

Example combinations of a compound X with a compound Y.

| X:Y | X:Y | X:Y | X:Y | X:Y | X:Y |
|---|---|---|---|---|---|
| 9000:7000 | 9001:7000 | 9002:7000 | 9003:7000 | 9004:7000 | 9005:7000 |
| 9000:7001 | 9001:7001 | 9002:7001 | 9003:7001 | 9004:7001 | 9005:7001 |
| 9000:7002 | 9001:7002 | 9002:7002 | 9003:7002 | 9004:7002 | 9005:7002 |
| 9000:7003 | 9001:7003 | 9002:7003 | 9003:7003 | 9004:7003 | 9005:7003 |
| 9000:7004 | 9001:7004 | 9002:7004 | 9003:7004 | 9004:7004 | 9005:7004 |
| 9000:7005 | 9001:7005 | 9002:7005 | 9003:7005 | 9004:7005 | 9005:7005 |
| 9000:7006 | 9001:7006 | 9002:7006 | 9003:7006 | 9004:7006 | 9005:7006 |
| 9000:7007 | 9001:7007 | 9002:7007 | 9003:7007 | 9004:7007 | 9005:7007 |
| 9000:7008 | 9001:7008 | 9002:7008 | 9003:7008 | 9004:7008 | 9005:7008 |
| 9000:7009 | 9001:7009 | 9002:7009 | 9003:7009 | 9004:7009 | 9005:7009 |
| 9000:7010 | 9001:7010 | 9002:7010 | 9003:7010 | 9004:7010 | 9005:7010 |
| 9000:7011 | 9001:7011 | 9002:7011 | 9003:7011 | 9004:7011 | 9005:7011 |
| 9000:7012 | 9001:7012 | 9002:7012 | 9003:7012 | 9004:7012 | 9005:7012 |
| 9000:7013 | 9001:7013 | 9002:7013 | 9003:7013 | 9004:7013 | 9005:7013 |
| 9000:7014 | 9001:7014 | 9002:7014 | 9003:7014 | 9004:7014 | 9005:7014 |
| 9000:7015 | 9001:7015 | 9002:7015 | 9003:7015 | 9004:7015 | 9005:7015 |
| 9000:7016 | 9001:7016 | 9002:7016 | 9003:7016 | 9004:7016 | 9005:7016 |
| 9000:7017 | 9001:7017 | 9002:7017 | 9003:7017 | 9004:7017 | 9005:7017 |
| 9000:7018 | 9001:7018 | 9002:7018 | 9003:7018 | 9004:7018 | 9005:7018 |
| 9000:7019 | 9001:7019 | 9002:7019 | 9003:7019 | 9004:7019 | 9005:7019 |
| 9000:7020 | 9001:7020 | 9002:7020 | 9003:7020 | 9004:7020 | 9005:7020 |
| 9000:7021 | 9001:7021 | 9002:7021 | 9003:7021 | 9004:7021 | 9005:7021 |
| 9000:7022 | 9001:7022 | 9002:7022 | 9003:7022 | 9004:7022 | 9005:7022 |
| 9000:7023 | 9001:7023 | 9002:7023 | 9003:7023 | 9004:7023 | 9005:7023 |
| 9000:7024 | 9001:7024 | 9002:7024 | 9003:7024 | 9004:7024 | 9005:7024 |
| 9000:7025 | 9001:7025 | 9002:7025 | 9003:7025 | 9004:7025 | 9005:7025 |
| 9000:7026 | 9001:7026 | 9002:7026 | 9003:7026 | 9004:7026 | 9005:7026 |
| 9000:7027 | 9001:7027 | 9002:7027 | 9003:7027 | 9004:7027 | 9005:7027 |
| 9006:7000 | 9007:7000 | 9008:7000 | 9009:7000 | 9010:7000 | 9011:7000 |
| 9006:7001 | 9007:7001 | 9008:7001 | 9009:7001 | 9010:7001 | 9011:7001 |
| 9006:7002 | 9007:7002 | 9008:7002 | 9009:7002 | 9010:7002 | 9011:7002 |
| 9006:7003 | 9007:7003 | 9008:7003 | 9009:7003 | 9010:7003 | 9011:7003 |
| 9006:7004 | 9007:7004 | 9008:7004 | 9009:7004 | 9010:7004 | 9011:7004 |
| 9006:7005 | 9007:7005 | 9008:7005 | 9009:7005 | 9010:7005 | 9011:7005 |
| 9006:7006 | 9007:7006 | 9008:7006 | 9009:7006 | 9010:7006 | 9011:7006 |
| 9006:7007 | 9007:7007 | 9008:7007 | 9009:7007 | 9010:7007 | 9011:7007 |

TABLE D-continued

Example combinations of a compound X with a compound Y.

| X:Y | X:Y | X:Y | X:Y | X:Y | X:Y |
|---|---|---|---|---|---|
| 9006:7008 | 9007:7008 | 9008:7008 | 9009:7008 | 9010:7008 | 9011:7008 |
| 9006:7009 | 9007:7009 | 9008:7009 | 9009:7009 | 9010:7009 | 9011:7009 |
| 9006:7010 | 9007:7010 | 9008:7010 | 9009:7010 | 9010:7010 | 9011:7010 |
| 9006:7011 | 9007:7011 | 9008:7011 | 9009:7011 | 9010:7011 | 9011:7011 |
| 9006:7012 | 9007:7012 | 9008:7012 | 9009:7012 | 9010:7012 | 9011:7012 |
| 9006:7013 | 9007:7013 | 9008:7013 | 9009:7013 | 9010:7013 | 9011:7013 |
| 9006:7014 | 9007:7014 | 9008:7014 | 9009:7014 | 9010:7014 | 9011:7014 |
| 9006:7015 | 9007:7015 | 9008:7015 | 9009:7015 | 9010:7015 | 9011:7015 |
| 9006:7016 | 9007:7016 | 9008:7016 | 9009:7016 | 9010:7016 | 9011:7016 |
| 9006:7017 | 9007:7017 | 9008:7017 | 9009:7017 | 9010:7017 | 9011:7017 |
| 9006:7018 | 9007:7018 | 9008:7018 | 9009:7018 | 9010:7018 | 9011:7018 |
| 9006:7019 | 9007:7019 | 9008:7019 | 9009:7019 | 9010:7019 | 9011:7019 |
| 9006:7020 | 9007:7020 | 9008:7020 | 9009:7020 | 9010:7020 | 9011:7020 |
| 9006:7021 | 9007:7021 | 9008:7021 | 9009:7021 | 9010:7021 | 9011:7021 |
| 9006:7022 | 9007:7022 | 9008:7022 | 9009:7022 | 9010:7022 | 9011:7022 |
| 9006:7023 | 9007:7023 | 9008:7023 | 9009:7023 | 9010:7023 | 9011:7023 |
| 9006:7024 | 9007:7024 | 9008:7024 | 9009:7024 | 9010:7024 | 9011:7024 |
| 9006:7025 | 9007:7025 | 9008:7025 | 9009:7025 | 9010:7025 | 9011:7025 |
| 9006:7026 | 9007:7026 | 9008:7026 | 9009:7026 | 9010:7026 | 9011:7026 |
| 9006:7027 | 9007:7027 | 9008:7027 | 9009:7027 | 9010:7027 | 9011:7027 |
| 9012:7000 | 9013:7000 | 9014:7000 | 9015:7000 | — | — |
| 9012:7001 | 9013:7001 | 9014:7001 | 9015:7001 | | |
| 9012:7002 | 9013:7002 | 9014:7002 | 9015:7002 | | |
| 9012:7003 | 9013:7003 | 9014:7003 | 9015:7003 | | |
| 9012:7004 | 9013:7004 | 9014:7004 | 9015:7004 | | |
| 9012:7005 | 9013:7005 | 9014:7005 | 9015:7005 | | |
| 9012:7006 | 9013:7006 | 9014:7006 | 9015:7006 | | |
| 9012:7007 | 9013:7007 | 9014:7007 | 9015:7007 | | |
| 9012:7008 | 9013:7008 | 9014:7008 | 9015:7008 | | |
| 9012:7009 | 9013:7009 | 9014:7009 | 9015:7009 | | |
| 9012:7010 | 9013:7010 | 9014:7010 | 9015:7010 | | |
| 9012:7011 | 9013:7011 | 9014:7011 | 9015:7011 | | |
| 9012:7012 | 9013:7012 | 9014:7012 | 9015:7012 | | |
| 9012:7013 | 9013:7013 | 9014:7013 | 9015:7013 | | |
| 9012:7014 | 9013:7014 | 9014:7014 | 9015:7014 | | |
| 9012:7015 | 9013:7015 | 9014:7015 | 9015:7015 | | |
| 9012:7016 | 9013:7016 | 9014:7016 | 9015:7016 | | |
| 9012:7017 | 9013:7017 | 9014:7017 | 9015:7017 | | |
| 9012:7018 | 9013:7018 | 9014:7018 | 9015:7018 | | |
| 9012:7019 | 9013:7019 | 9014:7019 | 9015:7019 | | |
| 9012:7020 | 9013:7020 | 9014:7020 | 9015:7020 | | |
| 9012:7021 | 9013:7021 | 9014:7021 | 9015:7021 | | |
| 9012:7022 | 9013:7022 | 9014:7022 | 9015:7022 | | |
| 9012:7023 | 9013:7023 | 9014:7023 | 9015:7023 | | |
| 9012:7024 | 9013:7024 | 9014:7024 | 9015:7024 | | |
| 9012:7025 | 9013:7025 | 9014:7025 | 9015:7025 | | |
| 9012:7026 | 9013:7026 | 9014:7026 | 9015:7026 | | |
| 9012:7027 | 9013:7027 | 9014:7027 | 9015:7027 | | |

TABLE E

Example combinations of a compound X with a compound Y.

| X:Y | X:Y | X:Y | X:Y | X:Y | X:Y |
|---|---|---|---|---|---|
| 8000:9000 | 8000:9001 | 8000:9002 | 8000:9003 | 8000:9004 | 8000:9005 |
| 8001:9000 | 8001:9001 | 8001:9002 | 8001:9003 | 8001:9004 | 8001:9005 |
| 8002:9000 | 8002:9001 | 8002:9002 | 8002:9003 | 8002:9004 | 8002:9005 |
| 8003:9000 | 8003:9001 | 8003:9002 | 8003:9003 | 8003:9004 | 8003:9005 |
| 8004:9000 | 8004:9001 | 8004:9002 | 8004:9003 | 8004:9004 | 8004:9005 |
| 8005:9000 | 8005:9001 | 8005:9002 | 8005:9003 | 8005:9004 | 8005:9005 |
| 8006:9000 | 8006:9001 | 8006:9002 | 8006:9003 | 8006:9004 | 8006:9005 |
| 8007:9000 | 8007:9001 | 8007:9002 | 8007:9003 | 8007:9004 | 8007:9005 |
| 8008:9000 | 8008:9001 | 8008:9002 | 8008:9003 | 8008:9004 | 8008:9005 |
| 8009:9000 | 8009:9001 | 8009:9002 | 8009:9003 | 8009:9004 | 8009:9005 |
| 8010:9000 | 8010:9001 | 8010:9002 | 8010:9003 | 8010:9004 | 8010:9005 |
| 8011:9000 | 8011:9001 | 8011:9002 | 8011:9003 | 8011:9004 | 8011:9005 |
| 8012:9000 | 8012:9001 | 8012:9002 | 8012:9003 | 8012:9004 | 8012:9005 |
| 8013:9000 | 8013:9001 | 8013:9002 | 8013:9003 | 8013:9004 | 8013:9005 |
| 8014:9000 | 8014:9001 | 8014:9002 | 8014:9003 | 8014:9004 | 8014:9005 |
| 8015:9000 | 8015:9001 | 8015:9002 | 8015:9003 | 8015:9004 | 8015:9005 |
| 8016:9000 | 8016:9001 | 8016:9002 | 8016:9003 | 8016:9004 | 8016:9005 |
| 8000:9006 | 8000:9007 | 8000:9008 | 8000:9009 | 8000:9010 | 8000:9011 |

TABLE E-continued

Example combinations of a compound X with a compound Y.

| X:Y | X:Y | X:Y | X:Y | X:Y | X:Y |
|---|---|---|---|---|---|
| 8001:9006 | 8001:9007 | 8001:9008 | 8001:9009 | 8001:9010 | 8001:9011 |
| 8002:9006 | 8002:9007 | 8002:9008 | 8002:9009 | 8002:9010 | 8002:9011 |
| 8003:9006 | 8003:9007 | 8003:9008 | 8003:9009 | 8003:9010 | 8003:9011 |
| 8004:9006 | 8004:9007 | 8004:9008 | 8004:9009 | 8004:9010 | 8004:9011 |
| 8005:9006 | 8005:9007 | 8005:9008 | 8005:9009 | 8005:9010 | 8005:9011 |
| 8006:9006 | 8006:9007 | 8006:9008 | 8006:9009 | 8006:9010 | 8006:9011 |
| 8007:9006 | 8007:9007 | 8007:9008 | 8007:9009 | 8007:9010 | 8007:9011 |
| 8008:9006 | 8008:9007 | 8008:9008 | 8008:9009 | 8008:9010 | 8008:9011 |
| 8009:9006 | 8009:9007 | 8009:9008 | 8009:9009 | 8009:9010 | 8009:9011 |
| 8010:9006 | 8010:9007 | 8010:9008 | 8010:9009 | 8010:9010 | 8010:9011 |
| 8011:9006 | 8011:9007 | 8011:9008 | 8011:9009 | 8011:9010 | 8011:9011 |
| 8012:9006 | 8012:9007 | 8012:9008 | 8012:9009 | 8012:9010 | 8012:9011 |
| 8013:9006 | 8013:9007 | 8013:9008 | 8013:9009 | 8013:9010 | 8013:9011 |
| 8014:9006 | 8014:9007 | 8014:9008 | 8014:9009 | 8014:9010 | 8014:9011 |
| 8015:9006 | 8015:9007 | 8015:9008 | 8015:9009 | 8015:9010 | 8015:9011 |
| 8016:9006 | 8016:9007 | 8016:9008 | 8016:9009 | 8016:9010 | 8016:9011 |
| 8000:9012 | 8000:9013 | 8000:9014 | 8000:9015 | — | — |
| 8001:9012 | 8001:9013 | 8001:9014 | 8001:9015 | | |
| 8002:9012 | 8002:9013 | 8002:9014 | 8002:9015 | | |
| 8003:9012 | 8003:9013 | 8003:9014 | 8003:9015 | | |
| 8004:9012 | 8004:9013 | 8004:9014 | 8004:9015 | | |
| 8005:9012 | 8005:9013 | 8005:9014 | 8005:9015 | | |
| 8006:9012 | 8006:9013 | 8006:9014 | 8006:9015 | | |
| 8007:9012 | 8007:9013 | 8007:9014 | 8007:9015 | | |
| 8008:9012 | 8008:9013 | 8008:9014 | 8008:9015 | | |
| 8009:9012 | 8009:9013 | 8009:9014 | 8009:9015 | | |
| 8010:9012 | 8010:9013 | 8010:9014 | 8010:9015 | | |
| 8011:9012 | 8011:9013 | 8011:9014 | 8011:9015 | | |
| 8012:9012 | 8012:9013 | 8012:9014 | 8012:9015 | | |
| 8013:9012 | 8013:9013 | 8013:9014 | 8013:9015 | | |
| 8014:9012 | 8014:9013 | 8014:9014 | 8014:9015 | | |
| 8015:9012 | 8015:9013 | 8015:9014 | 8015:9015 | | |
| 8016:9012 | 8016:9013 | 8016:9014 | 8016:9015 | | |

EXAMPLES

Additional embodiments are disclosed in further detail in the following examples, which are not in any way intended to limit the scope of the claims.

Example 1

(2R,3S,4R,5R)-2-(2-amino-6-ethoxy-9H-purin-9-yl)-4-fluoro-5-(hydroxymethyl)-3-methyltetrahydrofuran-3-ol (1)

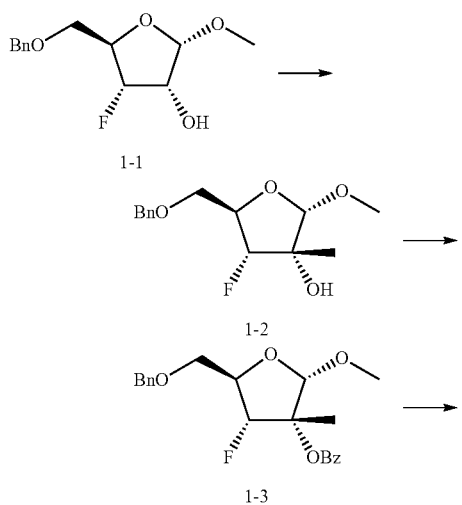

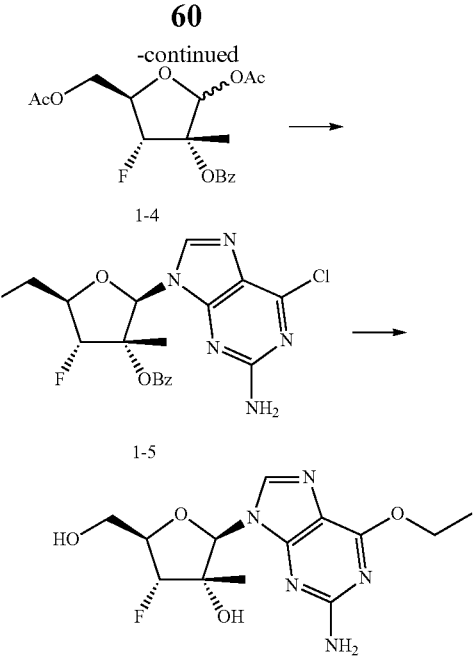

Preparation of (32-2):

To a stirred solution of 1-1 (5.0 g, 19.53 mmol) in anhydrous MeCN was added IBX (7.66 g, 27.34 mmol), and the mixture was heated to 80° C. for 12 h. The mixture was cooled to room temperature (R.T.) and filtered. The filtrate was concentrated to dryness to give the ketone (4.87 g, 98%) as a colorless oil. To a solution of the ketone (4.87 g, 19.33 mmol) in anhydrous THF was added methyl magnesium bromide (19.53 mL, 58.59 mmol) dropwise at −78° C. under $N_2$. The mixture was warmed to R.T. for 12 h. The reaction was quenched with a saturated ammonium chloride solution, extracted with ethyl acetate (EA) and concentrated to give a residue, which was purified on a silica gel column (2-10% EA in PE) to give 1-2 (4.37 g, 83%) as colorless oil.

Preparation of (32-3):

To a solution of 1-2 (4.37 g, 16.19 mmol) in anhydrous dichloromethane, DMAP (3.95 g, 32.38 mmol), TEA (4.91 g, 48.56 mmol) in ice water bath was added BzCl (6.80 g, 48.56 mmol). The mixture was stirred at R.T. for 12 h. The reaction was quenched with a saturated sodium hydrogen carbonate solution and extracted with EA. The organic phase was concentrated to dryness and purified on a silica gel column (2-20% EA in PE) to give 1-3 (5.3 g, 87%) as a colorless oil.

Preparation of (32-4):

To a solution of 1-3 (2.0 g, 5.33 mmol) and $Ac_2O$ (4.91 g, 48.13 mmol) in acetic acid (50 mL) was added concentrated $H_2SO_4$ (0.6 g, 6.01 mmol) at 0° C. The mixture was stirred at R.T. for 12 h. The mixture was then poured into ice water and extracted with EA. The organic phase was concentrated to dryness, and the residue was purified on a silica gel column (2-30% EA in PE) to give 1-4 (1.5 g, 81%) as colorless oil.

Preparation of (32-5):

To a stirred solution of 6-chloroguanine (560 mg, 3.31 mmol) and 1-4 (1.11 g, 2.76 mmol) in anhydrous MeCN (5 mL) under $N_2$ was added 1,8-diazobicyclo[5.4.0]undec-7-ene (1.27 g, 8.28 mmol) at 0° C. The mixture was stirred at R.T. for 0.5 h. TMSOTf (2.45 g, 11.04 mmol) was added at 0° C. The mixture was heated to 60° C. for 4 h and then concentrated to dryness. The residue was partitioned between EA and saturated sodium hydrogen carbonate. The organic phase was separated and concentrated to dryness. The residue was purified on a silica gel column (2-60% EA in PE) to give 1-5 (800 mg, 70%) as a white foam solid.

Preparation of (1):

To a solution of 1-6 (500 mg, 0.68 mmol) in anhydrous ethanol was added sodium ethoxide (0.64 mL, 2.04 mmol) at R.T. The mixture was stirred at R.T. for 16 h. The reaction was quenched by acetic acid to pH=7. The solvent was removed under reduce pressure. The residue was re-dissolved in EA, and washed with water and brine. The organic phase was dried and concentrated to dryness. The residue was purified on a silica gel column (1-3% DCM in MeOH) to give 1 (400 mg, 98%) as a white foam. ESI-MS: m/z 327.8 [M+H]$^+$.

Example 2

(2S)-neopentyl 2-(((((2R,3R,4S,5R)-5-(2-amino-6-ethoxy-1H-purin-9(6H)-yl)-3-fluoro-4-hydroxy-4-methyltetrahydrofuran-2-yl)methoxy)(2-chlorophenoxy)phosphoryl)amino)propanoate (2)

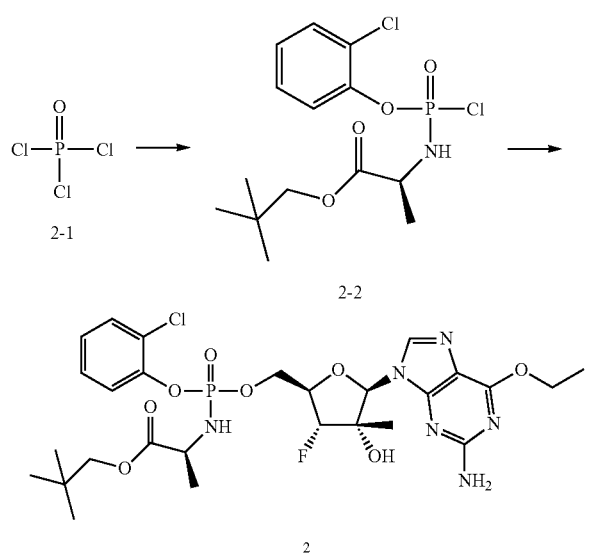

Preparation of (2-2):

To a stirred solution of 2-1 (2.00 g, 13.16 mmol) and 2-chlorophenol (1.68 g, 13.16 mmol) in anhydrous DCM (100 mL) was added a solution of TEA (1.33 g, 13.16 mmol) in DCM (20 mL) dropwise at −78° C. After the addition, the mixture was gradually warmed to R.T. and stirred for 2 h. The solution was re-cooled to −78° C. and neopentyl 2-aminopropanoate hydrogen chloride (3.51 g, 13.16 mmol) was added, followed by TEA (2.66 g, 26.32 mmol) dropwise at −78° C. The mixture was gradually warmed to R.T. and stirred at R.T. for 2 h. The solvent was removed, and the residue was dissolved in methyl-butyl ether. The precipitate was filtered off, and the filtrate was concentrated to dryness. The residue was purified on a silica gel column (pure anhydrous DCM) to give 2-2 (1.86 g, 32.18%) as a colorless oil.

Preparation of (2):

To a stirred solution of 1 (100 mg, 0.31 mmol) in anhydrous THF (10 mL) was added t-BuMgCl (1.53 mL, 1M in THF) dropwise at −78° C. The mixture was stirred at R.T. for 30 mins and re-cooled to −78° C. To the above mixture was added 2-2 (561 mg, 1.53 mmol) dropwise. The mixture was stirred at R.T. for 2 h. The reaction was quenched with water and extracted with EA. The organic layer was dried over anhydrous Na$_2$SO$_4$ and concentrated to dryness. The residue was purified on a silica gel column (1-8% DCM in MeOH) to give the crude product, which was further purified by RP HPLC (water and MeCN system) to give 2 (19.83 mg, 10%) as a white solid. ESI-LCMS: m/z 659.3 [M+H]$^+$.

Example 3

(2S)-cyclohexyl 2-(((((2R,3R,4S,5R)-5-(2-amino-6-ethoxy-1H-purin-9(6H)-yl)-3-fluoro-4-hydroxy-4-methyltetrahydrofuran-2-yl)methoxy)(3-chloro-4-fluorophenoxy)phosphoryl)amino)propanoate (3)

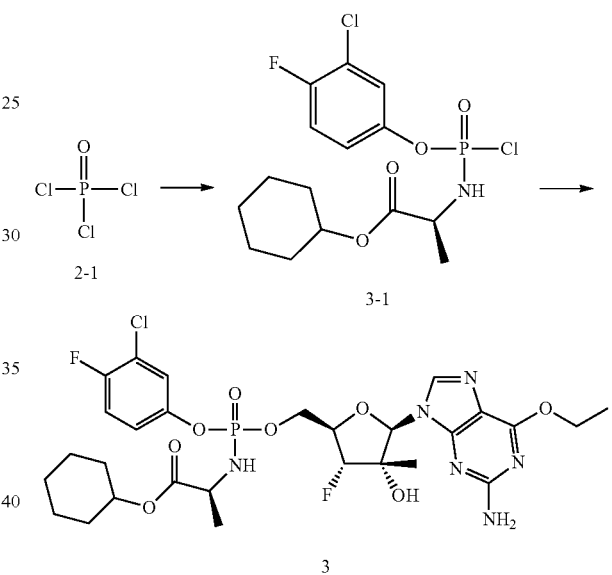

Preparation of (3-1):

To a stirred solution of phosphoryl trichloride (2.00 g, 13.16 mmol) and phenol (1.92 g, 13.16 mmol) in anhydrous DCM (100 mL) was added a solution of TEA (1.33 g, 13.16 mmol) in DCM (20 mL) dropwise at −78° C. After addition, the mixture was gradually warmed to R.T. and stirred for 2 h. The solution was re-cooled to −78° C. and the amine (2.72 g, 13.16 mmol) was added, followed by TEA (2.66 g, 26.32 mmol) dropwise at −78° C. The mixture was gradually warmed to R.T. and stirred for 2 h. The solvent was removed, and the residue was dissolved in methyl-butyl ether. The precipitate was filtered off, and the filtrate was concentrated. The residue was purified on a silica gel column (pure anhydrous DCM) to give 3-1 (1.90 g, 36.39%) as a colorless oil.

Preparation of (3):

To a stirred solution of 1 (181 mg, 0.55 mmol) in anhydrous THF (10 mL) was added t-BuMgCl (2.77 mL, 1M in THF) dropwise at −78° C. The mixture was stirred at R.T. for 30 mins and re-cooled to −78° C. To the mixture was added 3-1 (1.01 g, 2.77 mmol) dropwise. The mixture was stirred at R.T. for 12 h. The reaction was quenched with water and extracted with EA. The organic layer was dried over anhydrous Na₂SO₄ and concentrated to dryness. The residue was purified on a silica gel column (1-8% DCM in MeOH) to give the crude product, which was further purified by RP HPLC (water and MeCN system) to give 3 (76.81 mg, 20%) as a white solid. ESI-LCMS: m/z 689.3 [M+H]⁺.

Example 4

(2S)-neopentyl 2-(((((2R,3R,4S,5R)-5-(2-amino-6-ethoxy-1H-purin-9(6H)-yl)-3-fluoro-4-hydroxy-4-methyltetrahydrofuran-2-yl)methoxy)(phenoxy) phosphoryl)amino)propanoate (4)

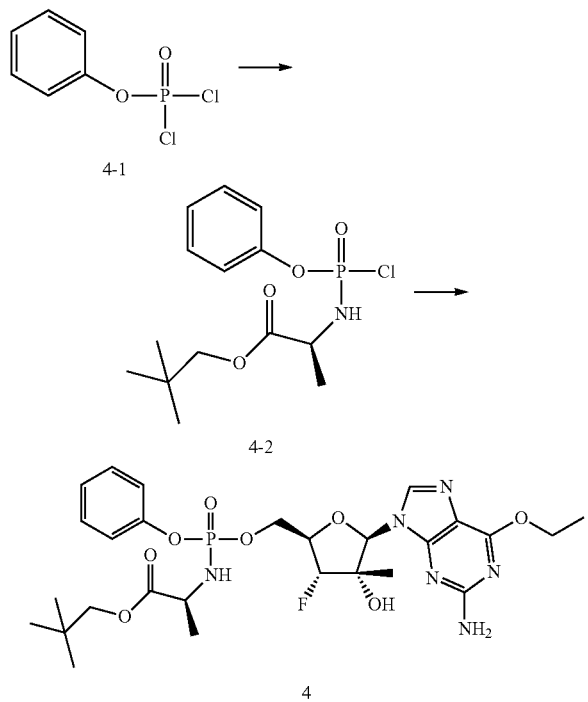

Preparation of (4-2):

To a stirred solution of 4-1 (3.20 g, 15.38 mmol) and amine (3.0 g, 15.38 mmol) in anhydrous DCM (100 mL) was added a solution of TEA (30.76 g, 30.76 mmol) in DCM (20 mL) dropwise at −78° C. After addition, the mixture was gradually warmed to R.T. and stirred for 2 h. The solvent was removed, and the residue was dissolved in methyl-butyl ether. The precipitate was filtered off, and the filtrate was concentrated. The residue was purified on a silica gel column (pure anhydrous DCM) to give 4-2 (2.0 g, 39%) as a colorless oil.

Preparation of (4):

To a stirred solution of 1 (83 mg, 0.25 mmol) in anhydrous THF (10 mL) was added a solution of t-BuMgCl (1.27 mL, 1M in THF) dropwise at −78° C. The mixture was stirred at R.T. for 30 mins and then re-cooled to −78° C. A solution of 4-2 (423 mg, 1.27 mmol) was added dropwise, and the mixture was stirred at R.T. for 12 h. The reaction was quenched with water and extracted with EA. The organic layer was dried over Na₂SO₄ and concentrated. The residue was purified on a silica gel column to give the crude product, which was further purified by RP HPLC (water and MeCN system) to give 4 (80 mg, 51%) as a white solid. ESI-LCMS: m/z 625.1 [M+H]⁺.

Example 5

(2S)-cyclohexyl 2-(((((2R,3R,4S,5R)-5-(2-amino-6-ethoxy-1H-purin-9(6H)-yl)-3-fluoro-4-hydroxy-4-methyltetrahydrofuran-2-yl)methoxy)(phenoxy) phosphoryl)amino)propanoate (5)

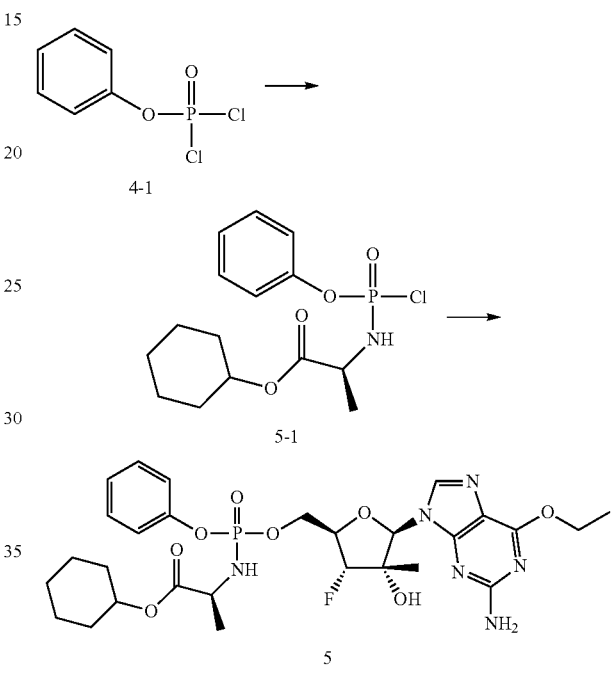

Preparation of (5-1):

To a stirred solution of 4-1 (2.00 g, 9.57 mmol) and amine (1.98 g, 9.57 mmol) in anhydrous DCM (100 mL) was added a solution of TEA (1.93 g, 19.14 mmol) in DCM (20 mL) dropwise at −78° C. After addition, the mixture was gradually warmed to R.T. and stirred for 2 h. The solvent was removed, and the residue was dissolved in methyl-butyl ether. The precipitate was filtered off, and the filtrate was concentrated. The residue was purified on a silica gel column (pure anhydrous DCM) to give 5-1 (700 mg, 21%) as a colorless oil.

Preparation of (5):

To a stirred solution of 1 (70 mg, 0.21 mmol) in anhydrous THF (1.5 mL) was added a solution of t-BuMgCl (1.07 mL, 1M in THF) dropwise at −78° C. The mixture was stirred at R.T. for 30 mins and then re-cooled to −78° C. A solution of 5-1 (369 mg, 1.07 mmol) was added dropwise. The mixture was stirred at R.T. for 2 h. The reaction was quenched with water and extracted with EA. The organic layer was dried over Na₂SO₄ and concentrated. The residue was purified on a silica gel column to give the crude product, which was further purified by RP HPLC (water and MeCN system) to give 5 (50 mg, 38%) as a white solid. ESI-LCMS: m/z 637.01 [M+H]⁺.

Example 6

2-amino-9-((2R,3S,4R,5R)-4-fluoro-3-hydroxy-5-(hydroxymethyl)-3-methyltetrahydrofuran-2-yl)-1H-purin-6(9H)-one (6)

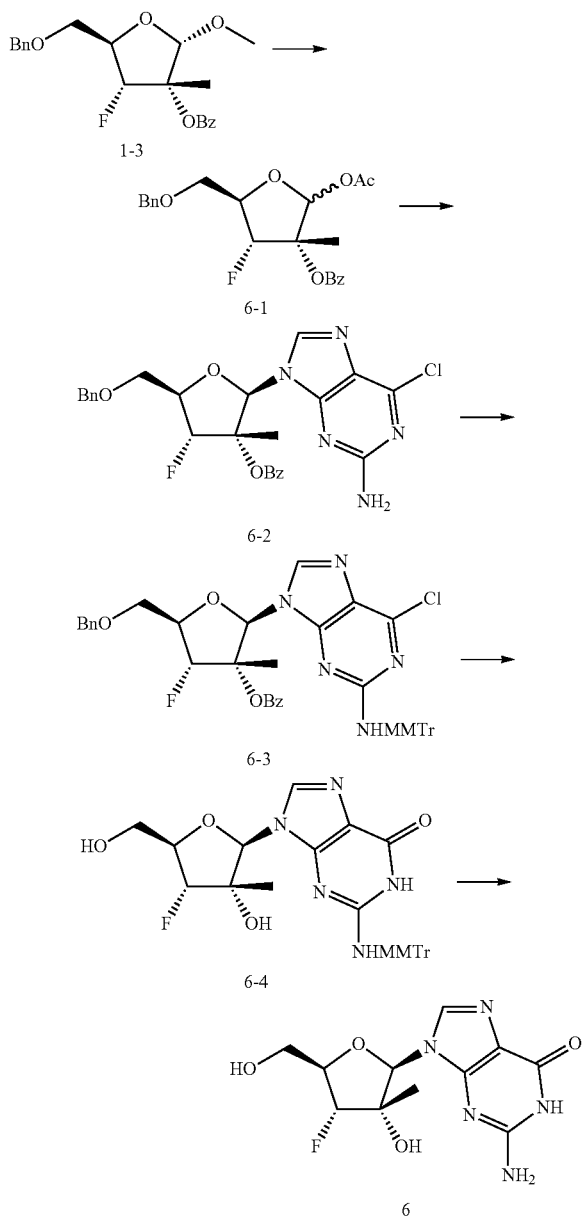

Preparation of (6-1):

To a solution of 1-3 (3.0 g, 8.02 mmol) and Ac₂O (4.91 g, 48.13 mmol) in acetic acid (30 mL) was added a solution of concentrated H₂SO₄ (2.41 g, 24.06 mmol) in acetic acid (10 mL) at 0° C. The mixture was stirred at R.T. for 12 h. The mixture was poured into ice water and extracted with EA. The organic phase was dried and concentrated to give a residue, which was purified by silica gel column chromatography (10% EA in PE) to give 6-1 (2.3 g, 81%) as a colorless oil.

Preparation of (6-2):

To a stirred mixture of 6-chloroguanine (560 mg, 3.31 mmol) and 6-1 (1.11 g, 2.76 mmol) in anhydrous MeCN (5 mL) under N₂ was added 1,8-diazobicyclo[5.4.0]undec-7-ene (1.27 g, 8.28 mmol) at 0° C. The mixture was stirred at R.T. for 0.5 h. The mixture was re-cooled to 0° C. and TMSOTf (2.45 g, 11.04 mmol) was added. The resulting mixture was heated to 60° C. for 4 h and then concentrated to dryness. The residue was partitioned between EA and saturated sodium hydrogen carbonate. The organic phase was separated and concentrated to give a residue, which was purified by silica gel column chromatography (2% MeOH in DCM) to give 6-2 (800 mg, 70%) as a white solid.

Preparation of (6-3):

To a solution of 6-2 (839 mg, 1.64 mmol) in anhydrous dichloromethane (10 mL) were added MMTrCl (1.46 g, 4.75 mmol), AgNO₃ (697 mg, 4.1 mmol) and collidine (794 mg, 6.56 mmol). The mixture was stirred at R.T. for 12 h. The reaction was quenched with saturated sodium hydrogen carbonate solution. The mixture was filtered, and the filtrate was extracted with EA. The organic layer was washed with water and brine, dried and concentrated to give a residue, which was purified on silica gel column chromatography (20% EA in PE) to give 6-3 (1.3 g, 72.5%) as a white solid.

Preparation of (6-4):

To a solution of 3-hydroxyl acrylic nitrile (413 g, 5.82 mmol) in anhydrous THF was added sodium hydrogen (464 mg, 11.6 mmol). The mixture was warmed to R.T. for 0.5 h, and then the mixture was re-cooled to 0° C. To the mixture was added a solution of 6-3 (0.912 g, 1.16 mmol) in anhydrous THF (5 mL). The mixture was warmed to R.T. for 12 h. The reaction was quenched with water and extracted with EA. The organic phase was separated and concentrated to give a residue, which was purified by silica gel column chromatography (5% MeOH in DCM) to give 6-4 (600 mg, 85%) as a white solid.

Preparation of (6):

To a solution of 6-4 (785 mg, 1.19 mmol) and ammonium formate (1.50 g, 23.75 mmol) in acetone (50 mL) was added dry Pd/C (785 mg). The mixture was heated to reflux for 12 h. The mixture was filtered, and the filtrate was concentrated under reduced pressure. The residue was purified by silica gel column chromatography (10% MeOH in DCM) to give 6 (400 mg, 59%) as a white solid. ESI-MS: m/z 299.77 [M+H]⁺.

Example 7

(2S)-neopentyl 2-(((((2R,3R,4S,5R)-5-(2-amino-6-oxo-1H-purin-9(6H)-yl)-3-fluoro-4-hydroxy-4-methyltetrahydrofuran-2-yl)methoxy)(2-chlorophenoxy)phosphoryl)amino)propanoate (7)

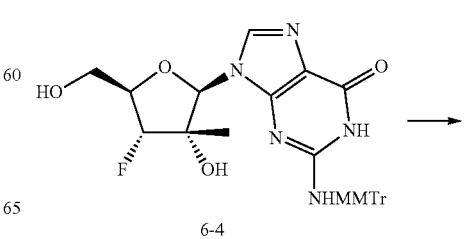

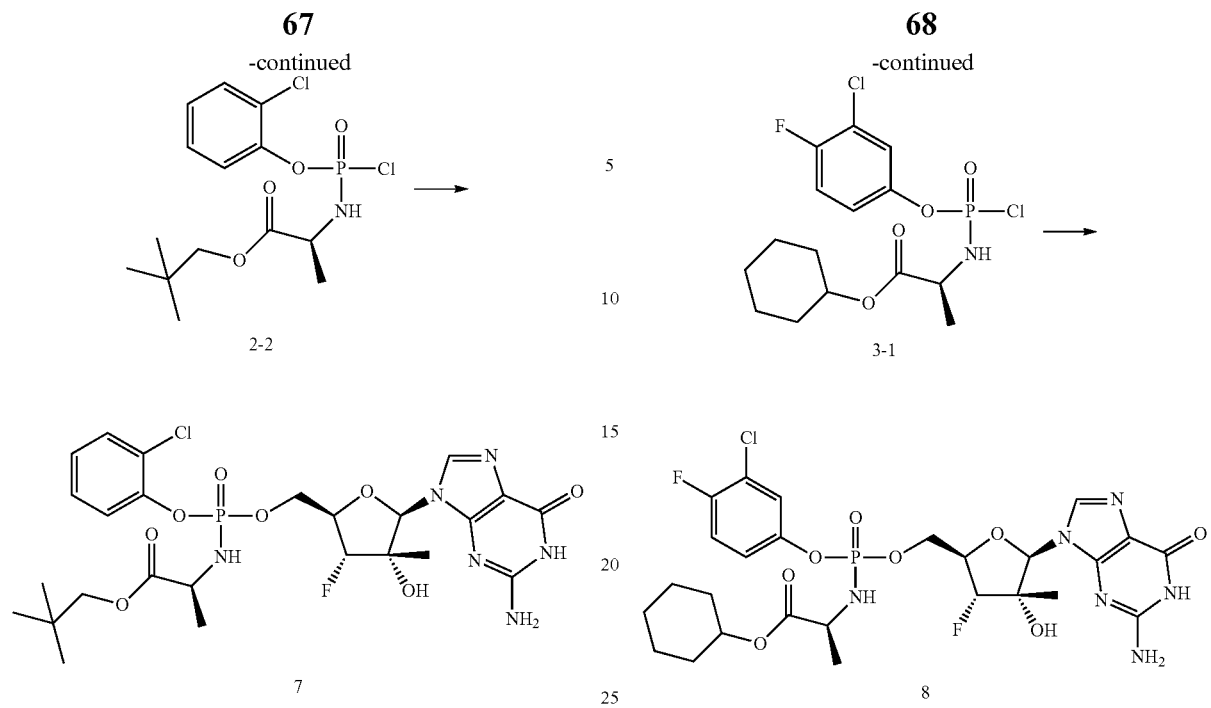

Preparation of (7):

To a stirred solution of 6-4 (161 mg, 0.28 mmol) in anhydrous THF (1 mL) was added a solution of t-BuMgCl (1.41 mL, 1M in THF) dropwise at 0° C. The mixture was stirred at R.T. for 0.5 h and then re-cooled to 0° C. To the mixture was added a solution of 2-2 (517 mg, 1.41 mmol) dropwise. The mixture was stirred at R.T. for 2 h. The reaction was quenched with water and extracted with EA. The organic layer was dried and concentrated. The residue was purified on a silica gel column to give a protected intermediate (100 mg). The protected intermediate was treated with a 60% acetic acid aqueous solution and stirred at R.T. for 12 h. The solvent was removed under reduced pressure. The residue was purified by silica gel column chromatography and then RP HPLC separation (0.1% HCOOH in water and MeCN) to give 7 (12.13 mg, 10%) as a white solid. ESI-LCMS: m/z 631.1 [M+H]$^+$.

Preparation of (8):

To a stirred solution of 6-4 (100 mg, 0.18 mmol) in anhydrous THF (1 mL) was added a solution of t-BuMgCl (0.9 mL, 0.9 mmol) dropwise at −78° C. The mixture was stirred at R.T. for 0.5 h and then re-cooled to −78° C. To the mixture was added a solution of 3-1 (357 mg, 0.9 mmol) dropwise. The mixture was stirred at R.T. for 12 h. The reaction was quenched with water and extracted with EA. The organic layer was dried and concentrated. The residue was purified on a silica gel column to give a protected intermediate (100 mg). The protected intermediate was treated with a 65% HCOOH aqueous solution and stirred at R.T. for 12 h. The solvent was removed under reduced pressure. The residue was purified by silica gel column chromatography and then RP HPLC (0.1% HCOOH in water and MeCN) to give 8 (16.83 mg, 14%) as a white solid. ESI-LCMS: m/z 661.1 [M+H]$^+$.

Example 8

(2S)-cyclohexyl 2-(((((2R,3R,4S,5R)-5-(2-amino-6-oxo-1H-purin-9(6H)-yl)-3-fluoro-4-hydroxy-4-methyltetrahydrofuran-2-yl)methoxy)(3-chloro-4-fluorophenoxy)phosphoryl)amino)propanoate (8)

Example 9

(2S)-cyclohexyl 2-(((((2R,3R,4S,5R)-5-(2-amino-6-oxo-1H-purin-9(6H)-yl)-3-fluoro-4-hydroxy-4-methyltetrahydrofuran-2-yl)methoxy)(phenoxy)phosphoryl)amino)propanoate

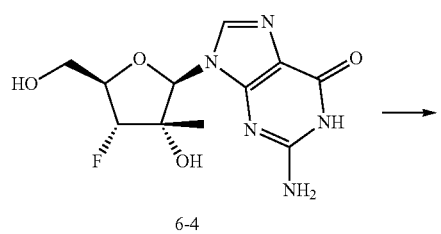

6-4

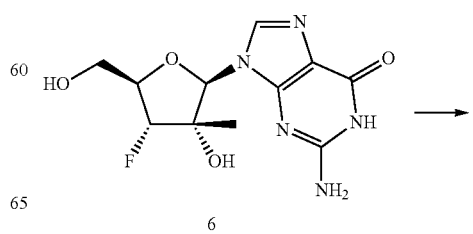

6

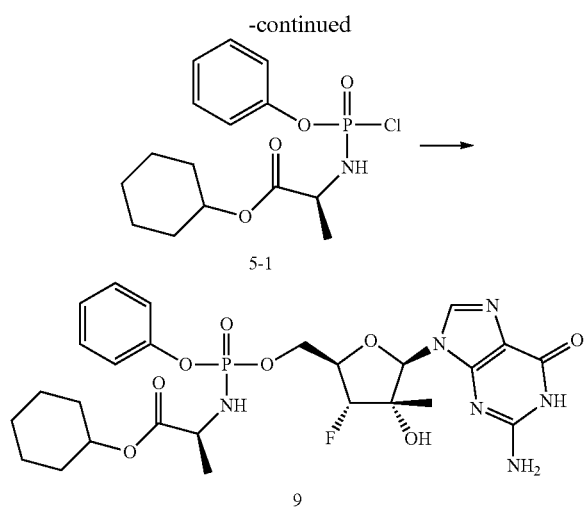

To a stirred solution of 6 (21 mg, 0.07 mmol) in NMI (0.25 mL) was added a solution of 5-1 (0.35 mL, 1M in THF) dropwise at 0° C. The mixture was stirred at R.T. for 5 h, then more 5-1 (0.21 mL) was added. The mixture was stirred for 3 days. Additionally, 5-1 (0.21 mL) was added, and the mixture was stirred at 35° C. for 1 day. After cooling to R.T., the mixture was diluted with EA, washed with NH$_4$Cl—AcOH (2 times), NH$_4$Cl (3 times), NaHCO$_3$. The organic layer was dried over sodium sulfate and concentrated. Chromatography on silica gel with 5-10% MeOH in DCM gave 9 (27 mg) as a slightly-yellow solid. Further chromatography on silica gel provided pure 9 (19 mg) as a white solid. ESI-LCMS: m/z 607.2 [M−H]$^-$.

Example 10

Compound (10)

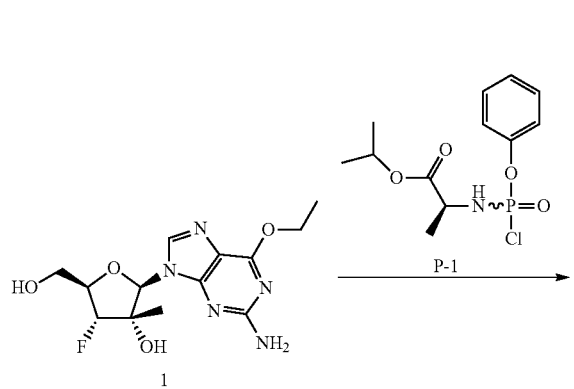

To an ice cold solution of 1 (53 mg; 016 mmol) in anhydrous THF (2 mL) was added isopropylmagnesium chloride (0.12 mL; 2 M in THF). The mixture stirred at 0° C. for 20 min. A solution of phosphorochloridate reagent P-1 (0.15 g; 3 equiv.) in THF (0.3 mL) was added dropwise. The mixture stirred overnight at R.T. The reaction was quenched with saturated aq. NH$_4$Cl solution and stirred at R.T. for 10 min. The mixture was diluted with water and CH$_2$Cl$_2$. The resulting two layers were separated. The organic layer was washed with water, half saturated aq. NaHCO$_3$ and brine, and then dried with Na$_2$SO$_4$. The evaporated residue was purified on silica gel column with CH$_2$Cl$_2$-MeOH solvent system (2-10% gradient) to yield a Rp/Sp-mixture of 10 (48 mg; 50%). $^{31}$P-NMR (DMSO-d$_6$): δ 3.98, 3.81. MS: m/z=595 [M−1]$^-$.

Example 11

Compound (11)

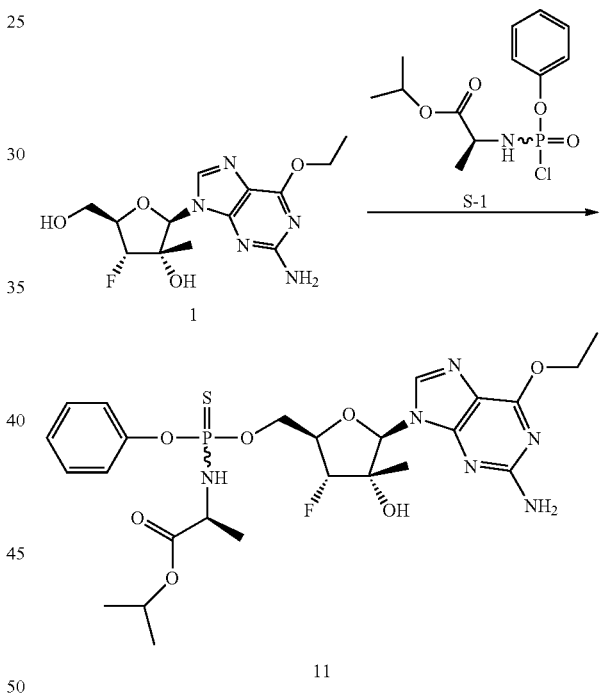

To an ice cold solution of 1 (95 mg; 029 mmol) in anhydrous THF (3 mL) was added isopropylmagnesium chloride (0.29 mL; 2 M in THF). The mixture stirred at 0° C. for 20 min. A solution of thiophosphorochloridate reagent S-1 (0.28 g; 3 equiv.) in THF (0.3 mL) was added, and the mixture stirred 1 day at 40° C. The reaction was quenched with saturated aq. NH$_4$Cl solution and stirred at R. T. for 10 min. The mixture was diluted with water and CH$_2$Cl$_2$, and the two layers were separated. The organic layer was washed with water, half saturated aq. NaHCO$_3$, and brine, and dried with Na$_2$SO$_4$. The evaporated residue was purified on silica gel column with CH$_2$Cl$_2$-MeOH solvent system (4-10% gradient) to yield Rp/Sp-mixture of 11 (42 mg; 24%). $^{31}$P-NMR (DMSO-d$_6$): δ 68.32, 68.19. MS: m/z=611 [M−1]$^-$.

Example 12

Compound (12)

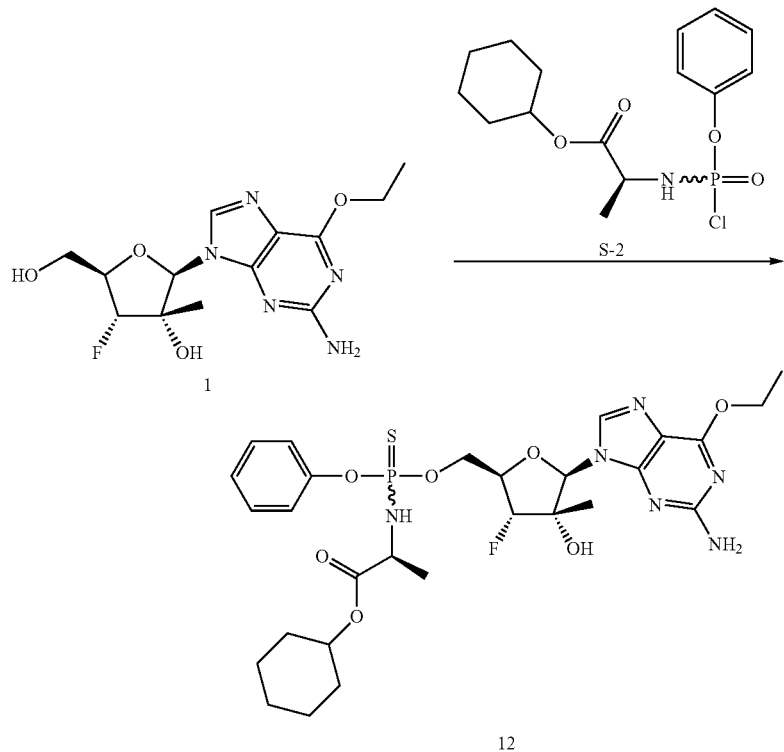

To a solution of 1 (91 mg; 0.28 mmol) in acetonitrile (2 mL) were added 1-methylimidazole (0.21 mL; 8 equiv.) and thiophosphorochloridate reagent S-2 (0.3 g; 3 equiv). The mixture stirred 1 day at 40° C. The reaction was quenched at R.T. with MeOH, and the mixture evaporated. The oily residue was dissolved in $CH_2Cl_2$ and washed with 1N citric acid, half saturated aq. $NaHCO_3$ and brine, and dried with $Na_2SO_4$. The evaporated residue was purified on silica gel column with $CH_2Cl_2$-MeOH solvent system (4-10% gradient) to yield Rp/Sp-mixture of 12 (120 mg; 66%). $^{31}$P-NMR (DMSO-$d_6$): δ 68.27, 68.24. MS: m/z=651 [M−1]$^−$.

Example 13

Compound (13)

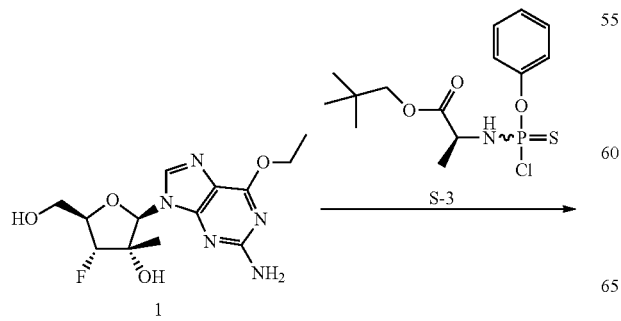

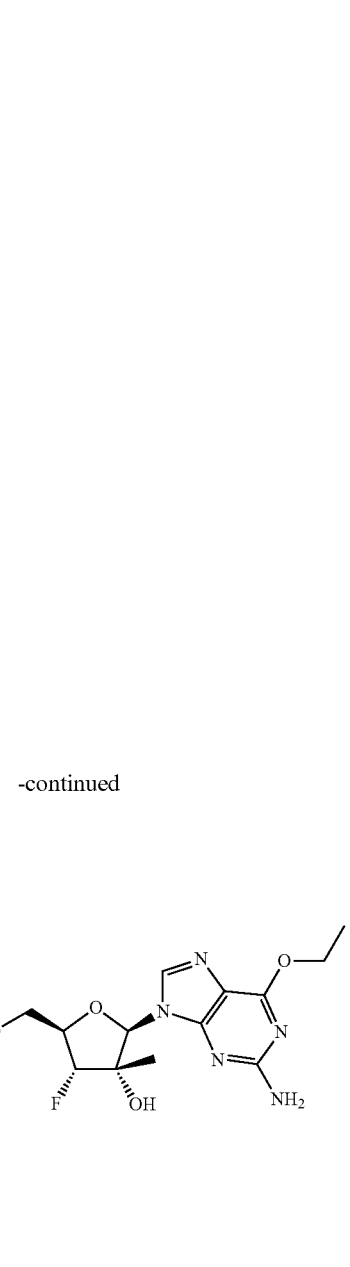

Compound 13 was prepared in the same way as described for 12 from 1 (75 mg; 0.23 mmol) with 1-methylimidazole (0.15 mL) and thiophosphorochloridate reagent S-3 (0.24 g) in acetonitrile (2 mL). 55 mg yield (37%). $^{31}$P-NMR (DMSO-$d_6$): δ 68.40, 68.16. MS: m/z=639 [M−1]$^−$.

Example 14

Compounds (14) and (15)

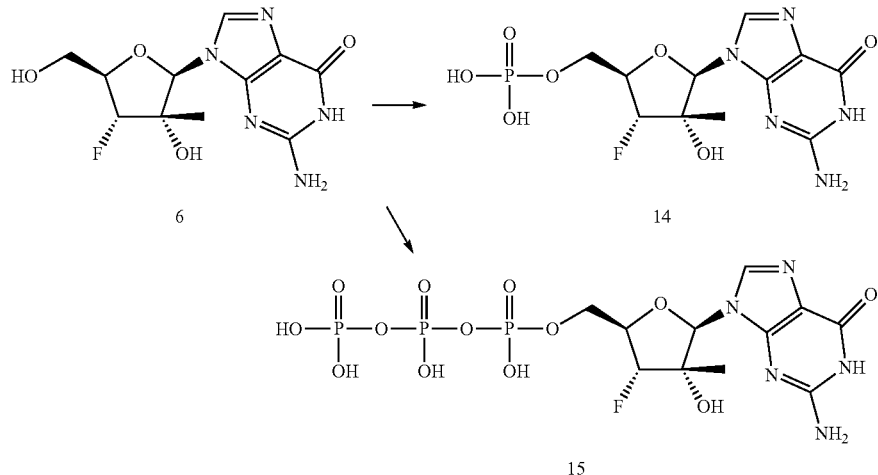

Dry 6 (18 mg, 0.05 mmol) was dissolved in the mixture of PO(OMe)$_3$ (0.750 mL) and pyridine (0.5 mL). The mixture was evaporated in vacuum for 15 mins at bath temperature (42° C.), and then cooled down to R.T. N-Methylimidazole (0.009 mL, 0.11 mmol) was added followed by POCl$_3$ (0.009 mL, 0.1 mmol). The mixture was kept at R.T. for 45 mins. Tributylamine (0.065 mL, 0.3 mmol) and N-tetrabutyl ammonium salt of pyrophosphate (100 mg) was added. Dry DMF (about 1 mL) was added to get a homogeneous solution. In 1 h, the reaction was quenched with 2M ammonium acetate buffer (1 mL, pH=7.5), diluted to 10 mL with water and loaded on the column HiLoad 16/10 with Q Sepharose High Performance.

Separation was done in a linear gradient of NaCl from 0 to 1N in 50 mM TRIS-buffer (pH=7.5). The fractions eluted at 60% buffer B contained 14 and at 80% buffer B contained 15. The corresponding fractions were concentrated, and the residue purified by RP HPLC on Synergy 4 micron Hydro-RP column (Phenominex). A linear gradient of methanol from 0 to 30% in 50 mM triethylammonium acetate buffer (pH 7.5) was used for elution. The corresponding fractions were combined, concentrated and lyophilized 3 times to remove excess of buffer. Compound 14: P$^{31}$-NMR (D$_2$O): −3.76 (s); $^1$H-NMR (D$_2$O): 8.00 (s, 1H), 5.88 (s, 1H), 5.10-4.95 (m, 2H), 4.05-3.98 (m, 2H), 1.00 (s, 3H); MS: 378.2 [M−1]$^−$. Compound 15: P$^{31}$-NMR (D$_2$O): −10.24 (Pα), −11.46 (Pβ), −23.18 (Pγ); $^1$H-NMR (D$_2$O): (D$_2$O): 8.44 (s, 1H), 8.17 (s, 1H), 5.05 (s, 1H), 4.18 (m, 2H), 4.02 (m, 3H); MS 538.0 [M−1]$^−$.

Example 15

HCV Replicon Assay

Cells

Huh-7 cells containing the self-replicating, subgenomic HCV replicon with a stable luciferase (LUC) reporter were cultured in Dulbecco's modified Eagle's medium (DMEM) containing 2 mM L-glutamine and supplemented with 10% heat-inactivated fetal bovine serum (FBS), 1% penicillin-streptomyocin, 1% nonessential amino acids, and 0.5 mg/mL G418.

Determination of Anti-HCV Activity

Determination of 50% inhibitory concentration (EC$_{50}$) of compounds in HCV replicon cells were performed by the following procedure. On the first day, 5,000 HCV replicon cells were plated per well in a 96-well plate. On the following day, test compounds were solubilized in 100% DMSO to 100× the desired final testing concentration. Each compound was then serially diluted (1:3) up to 9 different concentrations. Compounds in 100% DMSO are reduced to 10% DMSO by diluting 1:10 in cell culture media. The compounds were diluted to 10% DMSO with cell culture media, which were used to dose the HCV replicon cells in 96-well format. The final DMSO concentration was 1%. The HCV replicon cells were incubated at 37° C. for 72 h. At 72 h, cells were processed when the cells are still subconfluent. Compounds that reduce the LUC signal are determined by Bright-Glo Luciferase Assay (Promega, Madison, Wis.). % Inhibition was determined for each compound concentration in relation to the control cells (untreated HCV replicon) to calculate the EC$_{50}$.

Compounds of Formula (I) are active in the replicon assay. The antiviral activity of exemplary compounds is shown in Table 2, where 'A' indicates an EC$_{50}$<1 μM, 'B' indicates an EC$_{50}$≥1 μM and <10 μM, and 'C' indicates an EC$_{50}$≥10 μM and <100 μM.

TABLE 2

| Compound # | EC$_{50}$ |
|---|---|
| 2 | A |
| 3 | A |
| 4 | A |
| 5 | A |
| 6 | C |
| 7 | C |
| 8 | C |
| 9 | B |
| 10 | A |
| 11 | C |
| 12 | B |
| 13 | B |

Example 16

NS5B Inhibition Assay

The enzyme activity of NS5B570-Con1 (Delta-21) was measured as an incorporation of tritiated NMP into acid-insoluble RNA products. The complementary IRES (cIRES) RNA sequence was used as a template, corresponding to 377 nucleotides from the 3'-end of HCV (−) strand RNA of the Con-1 strain, with a base content of 21% Ade, 23% Ura, 28% Cyt, and 28% Gua. The cIRES RNA was transcribed in vitro using a T7 transcription kit (Ambion, Inc.) and purified using the Qiagen RNeasy maxi kit. HCV polymerase reactions contained 50 nM NS5B570-Con1, 50 nM cIRES RNA, about 0.5 µCi tritiated NTP, 1 µM of competing cold NTP, 20 mM NaCl, 40 mM Tris-HCl (pH 8.0), 4 mM dithiothreitol, and 4 mM $MgCl_2$. Standard reactions were incubated for 2 h at 37° C., in the presence of increasing concentration of inhibitor. At the end of the reaction, RNA was precipitated with 10% TCA, and acid-insoluble RNA products were filtered on a size exclusion 96-well plate. After washing of the plate, scintillation liquid was added and radio labeled RNA products were detected according to standard procedures with a Trilux Topcount scintillation counter. The compound concentration at which the enzyme-catalyzed rate was reduced by 50% ($IC_{50}$) was calculated by fitting the data to a non-linear regression (sigmoidal). The $IC_{50}$ values were derived from the mean of several independent experiments and are shown in Table 3. Compounds of Formula (I) showed activity in this assay. A value of 'A' in the table below indicates an $IC_{50}$ of <1 µM, a value of 'B' indicates an $IC_{50} \geq 1$ µM and <10 µM, and a value of 'C' indicates an $IC_{50}$ value of ≥10 µM and <100 µM.

TABLE 3

| Compound # | $IC_{50}$ |
|---|---|
| 15 | A |

Example 17

Assessment of Inhibition of Mitochondrial Function

Drug-associated dysfunction of mitochondria is believed to play a role in the etiology of the various adverse symptoms that occur in patients treated with antiviral nucleoside/nucleotides. For this reason, evaluation of compounds for their potential to inhibit mitochondrial function is useful. To assess the potential for nucleotide/nucleoside analogs to interfere with normal mitochondrial functions and exhibit mitochondrial toxicity, the following were measured: (1) the ability of nucleotides to be incorporated by human mitochondrial RNA polymerase in vitro and (2) the cellular inhibition of the synthesis of the mitochondrial DNA (mtDNA)-encoded protein, cytochrome c oxidase (COX-I), relative to the nuclear DNA (nDNA)-encoded mitochondrial protein succinate dehydrogenase subunit A (SDH-A) in HepG2 cells. Control compounds and compounds of Formula (I) were studied in these assays.

Biochemical Assay

Arnold et al. "Sensitivity of Mitochondrial Transcription and Resistance of RNA Polymerase II Dependent Nuclear Transcription to Antiviral Ribonucleosides" PLoS Pathog (2012) 8(11): e1003030. doi:10.1371/journal.ppat.1003030, which is hereby incorporated by reference in its entirety.

Assessment of Incorporation of Nucleotides by Human Mitochondrial RNA Polymerase (HMRP)

DdRp Assay with Human Mitochondrial RNA Polymerase

The DdRp assay with human mitochondrial RNA polymerase was performed under single turnover conditions where enzyme concentration is in excess of the primer/template. The $^{33}$P-RNA/DNA primer/template was used at a concentration of 100 nM, together with 320 nM enzyme. The standard 10-µL reactions were carried out at 30° C. for 1 minute with 100 µM of each nucleotide 5'-triphosphate (NTP), 10 mM $MgCl_2$, 50 mM NaCl, 40 mM Tris, pH 7.5, and 1 mM DTT. The reaction was stopped by adding 20 µL of formamide loading dye containing 50 mM EDTA. RNA products were resolved by electrophoresis on 22.5% TBE Urea polyacrylamide sequencing gels that were scanned using a TYPHOON PhosphorImager.

The template strand shown in FIG. 10 was designed to measure the incorporation of GTP analogs. Primer/Template: (SEQ ID NO: 1) UUUUGCCGCGCC and (SEQ ID NO: 2) GGGAATGCACGGCGCGGC. In the control water lanes, no incorporation was observed as indicated by the lack of product band. GTP and 3'-deoxy-GTP were found to be efficient substrates for incorporation as demonstrated by the significant product bands. The potential for misincorporation was assessed using the control nucleotide ATP. As shown by the lack of product band in FIG. 10, control ATP was a poor substrate for incorporation. Nucleotide analog 2'-Me-GTP (the nucleotide metabolite of monophosphate prodrug INX-0189/BMS-986094) was tested and found to be a good substrate for incorporation by HMRP as indicated by the product band. Nucleotide analog 2'-Me-2'-F-GTP (nucleotide metabolite of monophosphate prodrug GS-938) was tested and also found to be incorporated by HMRP. In contrast, compounds of Formula (I) were not efficient substrates for incorporation into the template strand by HMRP as indicated by the lack of product bands in FIG. 10.

Assessment of Inhibition of Mitochondrial Protein Synthesis—Cell Based Assay Assay Principle MitoBiogenesis™ In Cell ELISA kits (Cat. #MS643) were obtained from Mitosciences, OR, USA. The MitoBiogenesis™ In Cell ELISA kit is a duplexing 96 well assay that ratios both an mtDNA and an nDNA encoded mitochondrial protein. Cells were seeded in 96 microplates and after exposure to compounds for several cell doublings, the levels of the two mitochondrial proteins were measured simultaneously in each well. The two proteins assayed were each subunits of different oxidative phosphorylation enzyme complexes, one protein being subunit I of Complex IV (cytochrome c oxidase; COX I) that is mtDNA encoded and the other being the 70 kDa subunit of Complex II (succinate dehydrogenase subunit A; SDH A) that is nDNA encoded. Complex IV includes several proteins that are encoded by the mtDNA while the proteins of Complex II are entirely encoded by nDNA. To control for the density of cells present at the end of the culture period, the number of cells were assessed by staining with Janus Green and the levels of COX I/SDH A normalized to the final cell density.

96 Well Plate Assay Format for HepG2 Cells

On the first day, 1000 HepG2 cells per well were plated in a 96 well plate. On the following day, compounds to be tested were solubilized in 100% DMSO to 100× the desired final testing concentration. Each compound was serially diluted (1:3) up to 9 distinct concentrations. Compounds in 100% DMSO were reduced to 10% (v/v) DMSO by diluting 1:10 in cell culture media. A 10 µL aliquot of the compounds diluted to 10% (v/v) DMSO with cell culture media was used to dose the cells in duplicate. The final DMSO concentration was 1% (v/v). Untreated cells and wells containing no cells were included on the plate to serve as controls. Cells were then incubated with compounds and observed for 8 days at 37° C. and 5% $CO_2$. Plates were processed as described below in the assay procedure.

Batch Assay Format for HepG2 Cells

An alternate cell culture procedure was employed to test the potential to mediate mitochondrial toxicity at higher concentrations than achievable in the 96 well plate format. HepG2 cells were grown either in media/DMSO alone or in a series of compound concentrations in 15 $cm^2$ dishes or 6 well plates at an initial cell seeding density of $5 \times 10^6$ and $5 \times 10^4$ cells/mL, respectively. Cells were then incubated and observed for 8 days at 37° C. and 5% $CO_2$. After 8 days, the cells were harvested by trypsinization, counted, and seeded in 96 well plates at a density of 25,000 cells/well in 16 replicate wells. Cells were allowed to adhere overnight and then the plates were processed as described below in the assay procedure.

Assay Procedure

The assay was performed according to the manufacturer's instructions. Briefly, after the end of the culture period the cell culture media was gently aspirated from the wells of the plate and replaced with 100 μL of 4% (v/v) paraformaldehyde solution in phosphate buffered saline (PBS, Electron Microscopy Sciences Cat. #15713). After a 20 mins incubation at R.T., the solution was removed and the wells washed 3× with 300 μL of PBS. After the final wash, the PBS was removed and the wells overlayed with 100 μL PBS. The plates were then sealed and stored at 4° C. until used. To perform the assay, the PBS overlay was removed by blotting on a paper towel and 100 μL of 0.5% (v/v) acetic acid added to each well to block endogenous alkaline phosphatase activity. After a 5 mins incubation at R.T., the acetic acid solution was removed and the cells washed once with 200 μL PBS. Then, 100 μL of permeabilization buffer (0.1% (v/v) Triton X 100) was added to each well. After 30 mins incubation at R.T., the permeabilization buffer was removed and each well was blocked with 200 μL of 2× blocking solution for 2 h at R.T. The 2× blocking solution was then removed and 100 μL of primary antibody solution containing anti COX I and anti SDH A antibodies in 1× blocking solution was added to each well. Plates were then sealed and incubated overnight at 4° C. The primary antibody/blocking solution was removed and the plate washed 3× with 250 μL 0.05% (v/v) Tween 20 in PBS. Then, 100 μL of secondary antibody solution containing alkaline phosphatase (AP) labeled anti SDH A antibody and horseradish peroxidase (HRP) labeled anti COX I antibody was added and incubated for 1 h at R.T. The plate was then washed 4× with 250 μL 0.05% (v/v) Tween 20 in PBS. After blotting the plate dry 100 μL of AP detection reagent was added to each well, and the plate incubated in the dark for 30 mins at R.T. The optical density of each well was then measured at 405 nm. The AP detection reagent was then removed and replaced with 100 μL of HRP detection reagent, and the plate incubated in the dark for a further 30 mins at R.T. The optical density of each well was then measured at 600 nm. The HRP detection reagent was then removed and each well was then stained with 50 μL of 1× Janus Green Stain for 5 mins at R.T. After removal of the dye, the plates were washed 5× in ultrapure water to remove any remaining dye. The Janus Green stain was then solubilized by the addition of 100 μL of 0.5 M HCl and incubated for 10 mins. The optical density of each well was then measured at 595 nm.

Data Analysis

The average of all replicate background measurements from each experimental condition was calculated and subtracted from the experimental values of the same condition. The SDH A and COX I signals were then plotted as a ratio (COX I/SDH A) and normalized to the Janus Green staining intensity to correct for differences in cell density.

Results

Control compound d4T was tested and found not to inhibit mitochondrial protein synthesis at concentrations as shown in FIGS. 11A-B. Control compound ddC was tested and found to strongly inhibit mitochondrial protein synthesis. See FIGS. 11A-B. As demonstrated in FIG. 11B, nucleoside monophosphate prodrug INX-08189/BMS-986094 (which delivers 2'-Me-GTP) was tested in the assay and found to strongly inhibit mitochondrial protein synthesis. In contrast, compounds of Formula (I) were tested and found to not inhibit mitochondrial protein synthesis as shown in FIG. 11A.

Example 18

Combination of Compounds

Combination Testing

Two or more test compounds are tested in combination with each other using an HCV genotype 1b HCV replicon harbored in Huh7 cells with a stable luciferase (LUC) reporter. Cells are cultured under standard conditions in Dulbecco's modified Eagle's medium (DMEM; Mediatech Inc, Herndon, Va.) containing 10% heat-inactivated fetal bovine serum (FBS; Mediatech Inc, Herndon, Va.) 2 mM L-glutamine, and nonessential amino acids (JRH Biosciences). HCV replicon cells are plated in a 96-well plate at a density of $10^4$ cells per well in DMEM with 10% FBS. On the following day, the culture medium is replaced with DMEM containing either no compound as a control, the test compounds serially diluted in the presence of 2% FBS and 0.5% DMSO, or a combination of a compound of Formula (I) with one or more test compounds serially diluted in the presence of 2% FBS and 0.5% DMSO. The cells are incubated with no compound as a control, with the test compounds, or the combination of compounds for 72 h. The direct effects of the combination of the test compounds are examined using a luciferase (LUC) based reporter as determined by the Bright-Glo Luciferase Assay (Promega, Madison, Wis.). Dose-response curves are determined for individual compounds and fixed ratio combinations of two or more test compounds.

The method utilized for evaluating combination effects used a program called MacSynergy II. MacSynergy II software was kindly provided by Dr. M. Prichard (University of Michigan). The Prichard Model allows for a three-dimensional examination of drug interactions and a calculation of the synergy volume (units: $\mu M^2 \%$) generated from running the replicon assay using a checkerboard combination of two or more inhibitors. The volumes of synergy (positive volumes) or antagonism (negative volumes) represent the relative quantity of synergism or antagonism per change in the concentrations of the two drugs. Synergy and antagonism volumes are defined based on the Bliss independence model. In this model, synergy volumes of less than −25 indicate antagonistic interactions, volumes in the −25-25 range indicate additive behavior, volumes in the 25-100 range indicate synergistic behavior and volumes >100 indicate strong synergistic behavior. Determination of in vitro additive, synergistic and strongly synergistic behavior for combinations of compounds can be of utility in predicting therapeutic benefits for administering the combinations of compounds in vivo to infected patients.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming within the true scope and spirit of the invention.

an optionally substituted

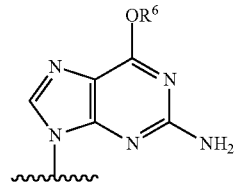

What is claimed is:

1. A compound of Formula (I), or a pharmaceutically acceptable salt thereof, having the structure:

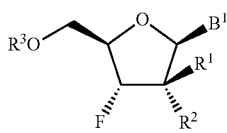

(I)

wherein:

B$^1$ is an optionally substituted

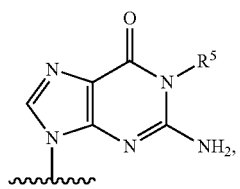

or an

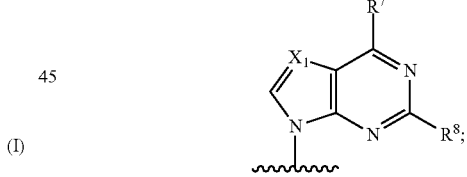

R$^1$ is selected from the group consisting of an unsubstituted C$_{1-6}$ alkyl, an unsubstituted C$_{2-6}$ alkenyl, an unsubstituted C$_{2-6}$ alkynyl, an unsubstituted C$_{3-6}$ cycloalkyl and an unsubstituted C$_{1-6}$ haloalkyl;

R$^2$ is halo, —OR$^{9A}$ or —N(R$^{9B}$R$^{9C}$);

R$^3$ is

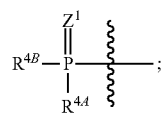

R$^{4A}$ is selected from the group consisting of O$^-$, OH, an optionally substituted N-linked amino acid and an optionally substituted N-linked amino acid ester derivative;

$R^{4B}$ is selected from the group consisting of O⁻, OH, an —O-optionally substituted phenyl, an —O-optionally substituted heteroaryl and an —O-optionally substituted heterocyclyl;

$R^5$ and $R^6$ are independently selected from the group consisting of hydrogen, an unsubstituted $C_{1-6}$ alkyl, an unsubstituted $C_{3-6}$ alkenyl, an unsubstituted $C_{3-6}$ alkynyl and an unsubstituted $C_{3-6}$ cycloalkyl;

$R^7$ is $NHR^{13}$;

$R^8$ is $NHR^{14}$;

$R^{9A}$ is hydrogen or —C(=O)$R^{15}$;

$R^{9B}$ and $R^{9C}$ are independently hydrogen or an optionally substituted $C_{1-6}$ alkyl;

$R^{13}$ is selected from the group consisting of hydrogen, an optionally substituted $C_{1-6}$ alkyl, an optionally substituted $C_{3-6}$ alkenyl, an optionally substituted $C_{3-6}$ cycloalkyl, —C(=O)$R^{41}$ and —C(=O)O$R^{42}$;

$R^{14}$ is selected from the group consisting of hydrogen, an optionally substituted $C_{1-6}$ alkyl, an optionally substituted $C_{3-6}$ alkenyl, an optionally substituted $C_{3-6}$ cycloalkyl, —C(=O)$R^{43}$ and —C(=O)O$R^{44}$;

$R^{15}$ is an optionally substituted $C_{1-6}$ alkyl or an optionally substituted $C_{3-6}$ cycloalkyl;

$X^1$ is N or —C$R^{16}$, $R^{16}$ is selected from the group consisting of hydrogen, halogen, an optionally substituted $C_{1-6}$ alkyl, an optionally substituted $C_{2-6}$ alkenyl and an optionally substituted $C_{2-6}$ alkynyl;

$R^{41}$, $R^{42}$, $R^{43}$ and $R^{44}$ are independently selected from the group consisting of $C_{1-6}$ alkyl, $C_{2-6}$ alkenyl, $C_{2-6}$ alkynyl, $C_{3-6}$ cycloalkyl, $C_{3-6}$ cycloalkenyl, $C_{6-10}$ aryl, heteroaryl, heteroalicyclyl, aryl($C_{1-6}$ alkyl), heteroaryl($C_{1-6}$ alkyl) and heteroalicyclyl($C_{1-6}$ alkyl);

$Z^1$ is O or S; and provided that when $R^3$ is

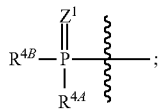

and $R^{4A}$ is O⁻ or OH, then $R^{4B}$ is O⁻ or OH; and when a group is substituted, the group is substituted with one or more substituents selected from the group consisting of alkyl, alkenyl, alkynyl, cycloalkyl, cycloalkenyl, aryl, heteroaryl, heteroalicyclyl, aralkyl, heteroaralkyl, (heteroalicyclyl)alkyl, hydroxy, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

2. The compound of claim 1, wherein $R^{4A}$ is an optionally substituted N-linked amino acid or an optionally substituted N-linked amino acid ester derivative; and $R^{4B}$ is an —O-optionally substituted phenyl.

3. The compound of claim 2, wherein $R^{4B}$ is an —O-unsubstituted phenyl.

4. The compound of claim 2, wherein $R^{4B}$ is an —O-substituted phenyl.

5. The compound of claim 2, wherein $R^{4A}$ is an optionally substituted N-linked amino acid ester derivative.

6. The compound of claim 5, wherein $R^{4A}$ is an optionally substituted $C_{1-5}$ alkyl ester, an optionally substituted $C_{3-6}$ cycloalkyl ester, an optionally substituted phenyl ester or an optionally substituted benzyl ester of an N-linked amino acid selected from the group consisting of N-linked alanine, N-linked glycine, N-linked leucine or N-linked valine.

7. The compound of claim 5, wherein $R^{4A}$ is an optionally substituted $C_{1-5}$ alkyl ester, an optionally substituted $C_{3-6}$ cycloalkyl ester, an optionally substituted phenyl ester or an optionally substituted benzyl ester of N-linked alanine.

8. The compound of claim 5, wherein $R^{4A}$ is an optionally substituted $C_{1-5}$ alkyl ester or an optionally substituted $C_{3-6}$ cycloalkyl ester of N-linked alanine.

9. The compound of claim 1, wherein $R^{4B}$ is O⁻ or OH; and $R^{4A}$ is O⁻ or OH.

10. The compound of claim 1, wherein $B^1$ is

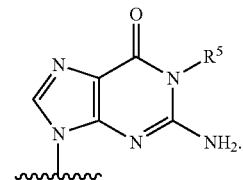

11. The compound of claim 1, wherein $B^1$ is

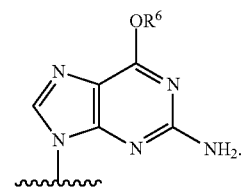

12. The compound of claim 11, wherein $R^6$ is an unsubstituted $C_{1-6}$ alkyl.

13. The compound of claim 12, wherein the unsubstituted $C_{1-6}$ alkyl is ethyl.

14. The compound of claim 11, wherein $R^6$ is an unsubstituted $C_{3-6}$ cycloalkyl.

15. The compound of claim 1, wherein $R^2$ is —OH.

16. The compound of claim 1, wherein $R^1$ is an unsubstituted $C_{1-6}$ alkyl.

17. The compound of claim 16, wherein $R^1$ is methyl.

18. The compound of claim 1, wherein $Z^1$ is O.

19. The compound of claim 1, wherein $Z^1$ is S.

20. The compound of claim 1, selected from the group consisting of:

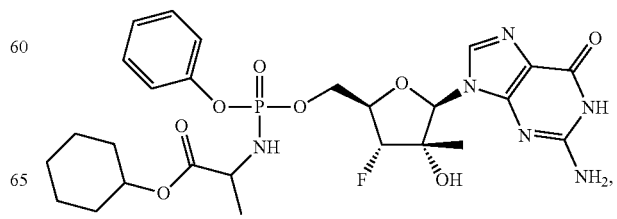

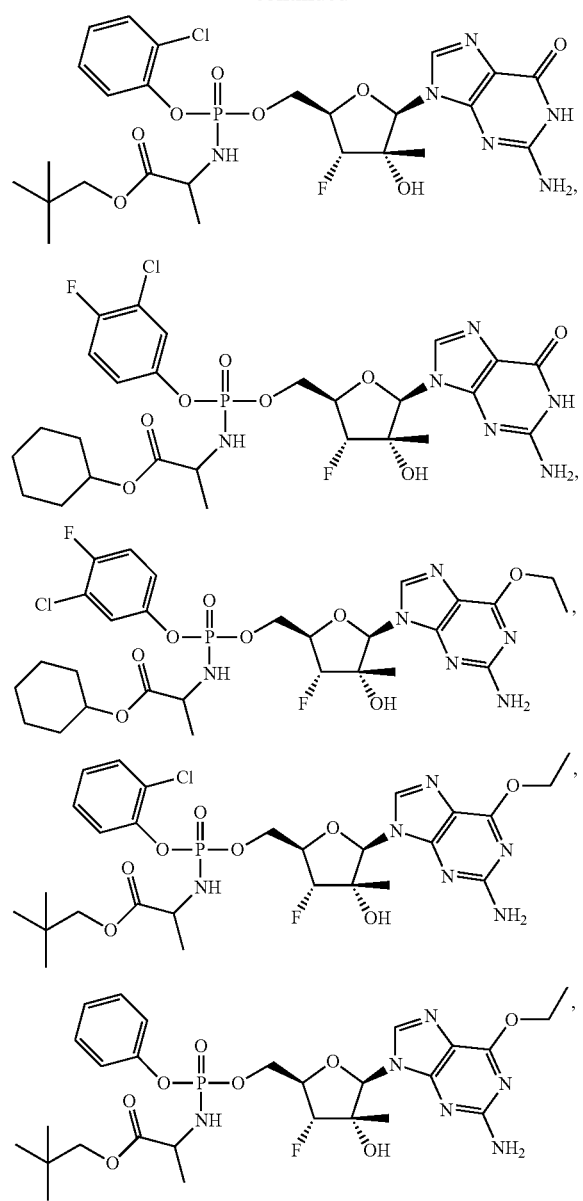
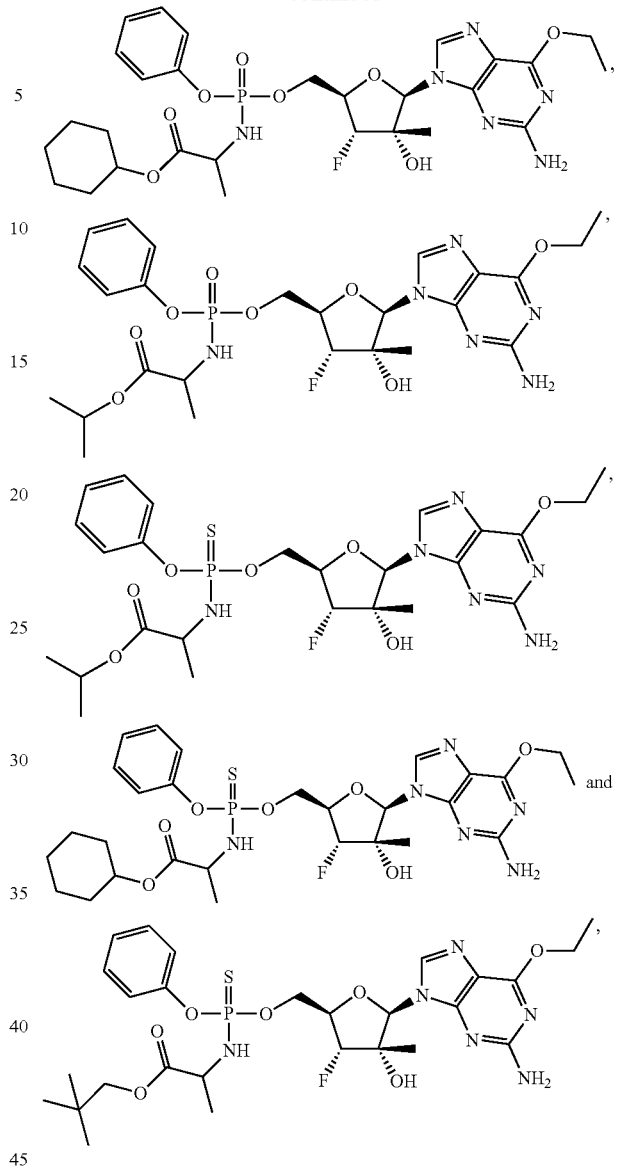
or a pharmaceutically acceptable salt of the foregoing.
* * * * *

SEQUENCE LISTING

```
<160> NUMBER OF SEQ ID NOS: 2

<210> SEQ ID NO 1
<211> LENGTH: 12
<212> TYPE: RNA
<213> ORGANISM: Artificial Sequence
<220> FEATURE:
<223> OTHER INFORMATION: synthetic polynucleotides

<400> SEQUENCE: 1
uuuugccgcg cc                                                      12

<210> SEQ ID NO 2
<211> LENGTH: 18
<212> TYPE: DNA
<213> ORGANISM: Artificial Sequence
<220> FEATURE:
<223> OTHER INFORMATION: synthetic polynucleotides

<400> SEQUENCE: 2
gggaatgcac ggcgcggc                                                18
```